US006992076B2

(12) United States Patent
Cundy et al.

(10) Patent No.: US 6,992,076 B2
(45) Date of Patent: Jan. 31, 2006

(54) BILE-ACID DERIVED COMPOUNDS FOR PROVIDING SUSTAINED SYSTEMIC CONCENTRATIONS OF DRUGS AFTER ORAL ADMINISTRATION

(75) Inventors: Kenneth C. Cundy, Redwood City, CA (US); Mark A. Gallop, Los Altos, CA (US); Cindy X. Zhou, Palo Alto, CA (US)

(73) Assignee: XenoPort, Inc., Santa Clara, CA (US)

( * ) Notice: Subject to any disclaimer, the term of this patent is extended or adjusted under 35 U.S.C. 154(b) by 388 days.

(21) Appl. No.: 09/972,425

(22) Filed: Oct. 5, 2001

(65) Prior Publication Data

US 2002/0151529 A1 Oct. 17, 2002

Related U.S. Application Data

(60) Provisional application No. 60/238,758, filed on Oct. 6, 2000, provisional application No. 60/249,804, filed on Nov. 17, 2000, and provisional application No. 60/297,594, filed on Jun. 11, 2001.

(51) Int. Cl.
*A61K 31/56* (2006.01)
*C07J 5/00* (2006.01)
*C07J 7/00* (2006.01)
*C07J 9/00* (2006.01)
*C07J 41/00* (2006.01)

(52) U.S. Cl. .................. 514/182; 552/553; 552/554; 552/557; 552/559

(58) Field of Classification Search .............. 552/553, 552/557, 559, 554; 514/182
See application file for complete search history.

(56) References Cited

U.S. PATENT DOCUMENTS

| 3,326,758 | A | 6/1967 | Irmscher et al. |
| 4,024,175 | A | 5/1977 | Satzinger |
| 4,508,728 | A | 4/1985 | Nagai et al. |
| 4,560,512 | A | 12/1985 | Firestone |
| 4,908,353 | A | 3/1990 | Yamamoto et al. |
| 5,094,848 | A | 3/1992 | Brixner |
| 5,110,797 | A | 5/1992 | Ienaga et al. |
| 5,462,933 | A | 10/1995 | Kramer et al. |
| 5,541,348 | A | 7/1996 | Araya et al. |
| 5,563,175 | A | 10/1996 | Silverman |
| 5,646,272 | A | 7/1997 | Kramer et al. |
| 5,668,126 | A | 9/1997 | Kramer et al. |
| 5,684,018 | A | 11/1997 | Alexander |
| 6,020,370 | A | 2/2000 | Horwell |
| 6,028,214 | A | 2/2000 | Silverman |
| 6,051,683 | A | 4/2000 | Deigin et al. |
| 6,103,932 | A | 8/2000 | Horwell |
| 6,117,906 | A | 9/2000 | Silverman |
| 6,143,738 | A | 11/2000 | Zasloff |

FOREIGN PATENT DOCUMENTS

| EP | 0 272 462 B1 | 6/1998 |
| WO | WO92/09560 | 6/1992 |
| WO | WO93/23383 | 11/1993 |
| WO | WO97/29101 | 8/1997 |
| WO | WO97/33858 | 9/1997 |
| WO | WO97/33859 | 9/1997 |
| WO | WO98/17627 | 4/1998 |
| WO | WO99/08671 | 2/1999 |
| WO | WO99/21824 | 5/1999 |
| WO | WO99/31057 | 6/1999 |
| WO | WO99/31074 | 6/1999 |
| WO | WO99/31075 | 6/1999 |
| WO | WO99/61424 | 12/1999 |
| WO | WO00/15611 | 3/2000 |
| WO | WO00/23067 | 4/2000 |
| WO | WO00/31020 | 6/2000 |
| WO | WO00/50027 | 8/2000 |

OTHER PUBLICATIONS

Baringhaus, K.–H.; Matter, H.; Stengelin, S.; Kramer, W. Substrate specificity of the ileal and the hepatic $Na^+$ / bile acid cotransporters of the rabbit. II. A reliable 3D QSAR pharmacophore model for the ileal $Na^+$ bile acid cotransporter. *J. Lipid Res.* 1999, 40, pp. 2158–2168.

Batta, et al., *J. Lipid Res.,* 1991, 32, pp. 977–983.

Bryans, J. S.; Wustrow, D. J. 3–Substituted GABA analogs with central nervous system activity: a review. *Med. Res. Rev.* 1999, 19, pp. 149–177.

Bundgaard, H. in *Design of Prodrugs* (Bundgaard, H. Ed.), Elsevier Science B.V., 1985, pp. 1–92.

Ho, N. F. H. Utilizing bile acid carrier mechanisms to enhance liver and small intestine absorption. *Ann: N. Y. Acad. Sci.* 1987, 507, pp. 315–329.

Jezyk, N.; Li, C.; Stewart, B. H.; Wu, X.; Bockbrader, H. N.; Fleisher, D. Transport of pregabalin in rat intestine and Caco–2 monolayers. *Pharm. Res.* 1999, 16, pp. 519–526.

Kagedahl, M.; Swaan, P. W.; Redemann, C. T.; Tang, M.; Craik, C. S.; Szoka, F. C.; Oie, S. Use of the intestinal bile acid transporter for the uptake of cholic acid conjugates with HIV–1 protease inhibitory activity. *Pharm. Res.* 1997, 14, pp. 176–180.

Kim, D.C., et al., Evaluation of bile acid transporter in enhancing intestinal permeability of renin–inhibitory peptides, *J. Drug Targeting*, 1993, 1, pp. 347–359.

Kramer, W.; Wess, G.; Schubert, G.; Bickel, M.; Girbig, F.; Gutjahr, U.; Kowalewski, S.; Baringhaus, K.–H.; Enhsen, A.; Glombik, H.; Mullner, S.; Neckermann, G.; Schulz, S.; Petzinger, E. Liver–specific drug targeting by coupling to bile acids. *J. Biol. Chem.* 1992, 267, pp. 18598–18604.

Kramer, W.; Wess, G.; Neckermann, G.; Schubert, G.; Fink, J.; Girbig, F.; Gutjahr, U.; Kowalewski, S.; Baringhaus, K.–H.; Boger, G.; Enhsen, A.; Falk, E.; Friedrich, M.; Glombik, H.; Hoffmann, A.; Pittius, C.; Urmann, M. Intestinal absorption of peptides by coupling to bile acids. *J. Biol. Chem.* 1994a, 269, pp. 10621–10627.

Kramer, W.; Wess, G.; Enhsen, A.; Bock, K.; Falk, E.; Hoffmann, A.; Neckermann, G.; Gantz, D.; Schulz, S.; Nickau, L.; Petzinger, E.; Turley, S.; Dietschy, J. M. Bile acid derived HMG–CoA reductase inhibitors. *Biochim. Biophys. Acta* 1994b, 1227, pp. 137–154.

Kramer, W.; Stengelin, S.; Baringhaus, K.-H.; Enhsen, A.; Heuer, H.; Becker, W.; Corsiero, D.; Girbig, F.; Noll, R.; Weyland, C. Substrate specificity of the ileal and hepatic $Na^+$ bile acid cotransporters of the rabbit. I. Transport studies with membrane vesicles and cell lines expressing the cloned transporters. *J. Lipid Res.* 1999, 40, pp. 1604–1617.

Kullak–Ublick, G. A.; Beuers, U.; Paumgartner, G. Hepatobiliary transport. *J. Hepatology* 2000, 32 (*Suppl. 1*), pp. 3–18.

Navia, M. A.; Chaturvedi, P. R. Design principles for orally bioavailable drugs. *Drug Discovery Today* 1996, 1, pp. 179–189.

Petzinger, E.; Nichau, L.; Horz, J. A.; Schulz, S.; Wess, G.; Enhsen, A.; Falk, E.; Baringhaus, H.; K. Glombik, H.; Hoffmann, A.; Mullner, S.; Neckermann, G.; Kramer, W. Hepatobiliary transport of hepatic 3–hydroxy–3– methylglutaryl coenzyme A reductase inhibitors conjugated with bile acids., *Hepatology* 1995, 22, pp. 1801–1811.

Swaan, P. W.; Szoka, F. C.; Oie, S. Use of the intestinal and hepatic bile acid transporters for drug delivery. *Adv. Drug Delivery Rev.* 1996, 20 pp. 59–82.

Tsjui, A.; Tamai, I. Carrier–mediated intestinal transport of drugs. *Pharm. Res.* 1996, 13, pp. 963–977.

*Primary Examiner*—Barbara P. Badio
(74) *Attorney, Agent, or Firm*—Burns, Doane, Swecker & Mathis, L.L.P.

(57) ABSTRACT

This invention is directed to methods for providing sustained systemic concentrations of therapeutic or prophylactic agents such as GABA analogs following oral administration to animals. This invention is also directed to compounds and pharmaceutical compositions that are used in such methods.

9 Claims, 33 Drawing Sheets

The Enterohepatic Circulation with Key Transporter Proteins Mediating Bile Acid Circulation

Figure 3
Bile Acid Conjugates of HMG-CoA Reductase Inhibitor
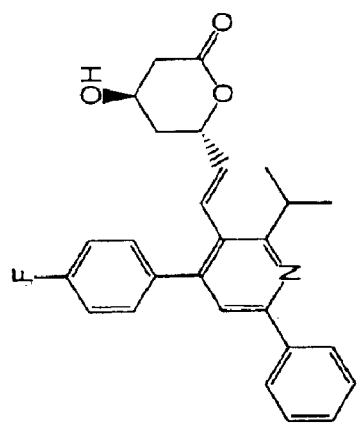
HR 780
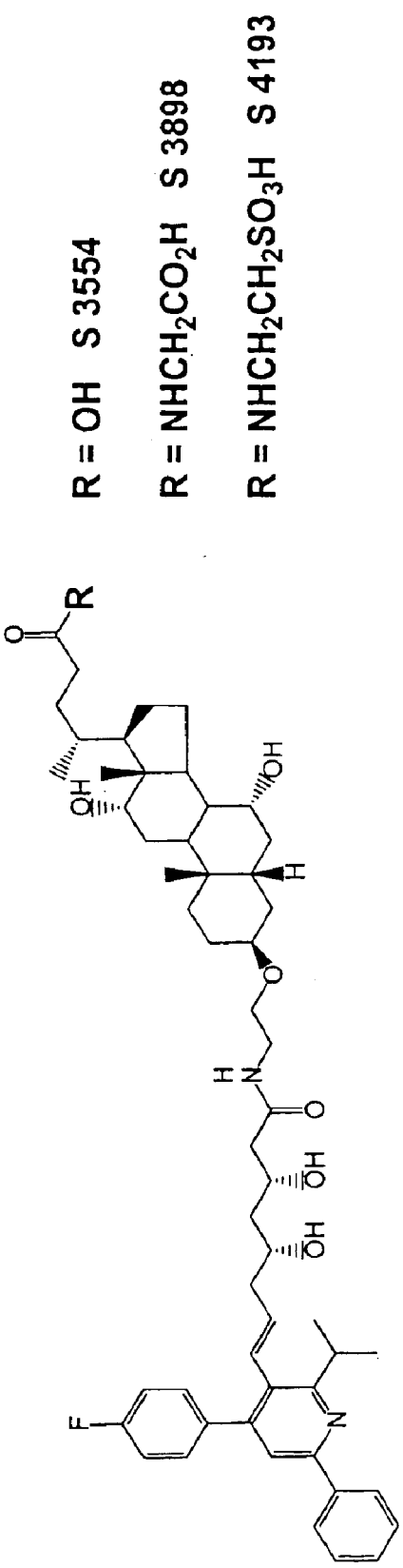
R = OH    S 3554
R = NHCH$_2$CO$_2$H    S 3898
R = NHCH$_2$CH$_2$SO$_3$H    S 4193

Figure 6
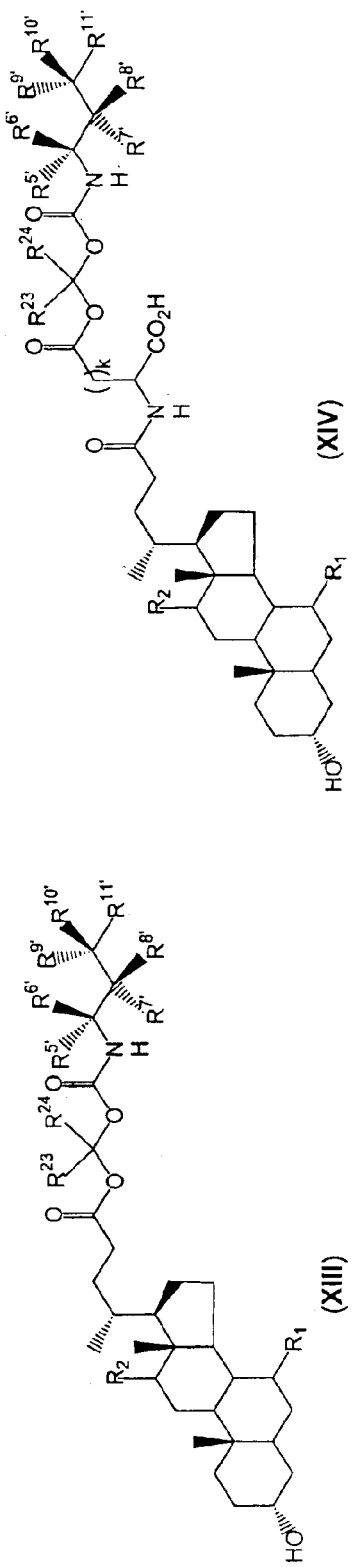
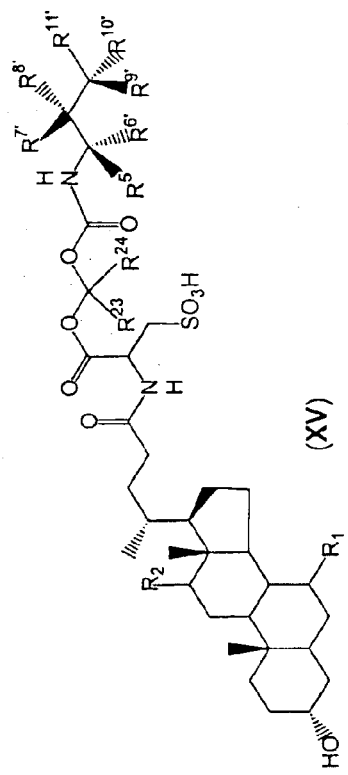
R1 = α-OH ; R2 = α-OH (Cholate)
R1 = β-OH ; R2 = H (Ursodeoxycholate)
R1 = α-OH ; R2 = H (Chenodeoxycholate)
R1 = H ; R2 = α-OH (Deoxycholate)
R1 = β-OH ; R2 = α-OH (Ursocholate)
R1 = H ; R2 = H (Lithocholate)

Figure 9: Uptake of (8) (XP10569) or Glycochocholate by IBAT-Transfected CHO Cells Compounds (92) - (103) prepared following methods described in co-pending application "Bile Acid-Derived Compounds for Enhancing Oral Absorption and Systemic Bioavailability of Drugs" assigned to XenoPort, Inc.

BILE-ACID DERIVED COMPOUNDS FOR PROVIDING SUSTAINED SYSTEMIC CONCENTRATIONS OF DRUGS AFTER ORAL ADMINISTRATION

CROSS-REFERENCE TO RELATED APPLICATIONS

This application claims the benefit of U.S. Provisional Application Ser. No. 60/238,758, which was filed on Oct. 6, 2000; U.S. Provisional Application Ser. No. 60/249,804, which was filed on Nov. 17, 2000; and U.S. Provisional Application Ser. No. 60/297,594 which was filed on Jun. 11, 2001, the disclosures of which are incorporated by reference in their entirety.

BACKGROUND OF THE INVENTION

1. Field of the Invention

This invention is directed to methods for providing sustained systemic concentrations of therapeutic or prophylactic agents such as GABA analogs following oral administration to animals. This invention is also directed to compounds and pharmaceutical compositions that are used in such methods.

2. References

The following publications, patents and patent applications are cited in this application as superscript numbers:

1. Arya, P.; Burton, G. W. Bile acids for biological and chemical applications and processes for the production thereof. U.S. Pat. No. 5,541,348, 1996.
2. Baringhaus, K.-H.; Matter, H.; Stengelin, S.; Kramer, W. Substrate specificity of the ileal and hepatic Na$^+$/bile acid cotransporters of the rabbit. II. A reliable 3D QSAR pharmacophore model for the ileal Na$^+$/bile acid cotransporter. *J. Lipid Res.* 1999, 40, 2158–2168.
3. Batta et al., *J. Lipid Res.* 1991, 32, 977–983.
4. Bryans, J. S.; Wustrow, D. J. 3-Substituted GABA analogs with central nervous system activity: a review. Med. Res. Rev. 1999, 19,149–177.
5. Bundgaard, H. in *Design of Prodrugs* (Bundgaard, H. Ed.), Elsevier Science B. V., 1985, pp. 1–92.
6. Fieser and Fieser's Reagents for Organic Synthesis, Volumes 1–15 (John Wiley and Sons, 1991);
7. Ho, N. F. H. Utilizing bile acid carrier mechanisms to enhance liver and small intestine absorption. *Ann. N. Y. Acad. Sci.* 1987, 507, 315–329.
8. Jezyk, N.; Li, C.; Stewart, B. H.; Wu, X.; Bockbrader, H. N.; Fleisher, D. Transport of pregabalin in rat intestine and Caco-2 monolayers. *Pharm. Res.* 1999, 16, 519–526.
9. Kagedahl, M.; Swaan, P. W.; Redemann, C. T.; Tang, M.; Craik, C. S.; Szoka, F. C.; Oie, S. Use of the intestinal bile acid transporter for the uptake of cholic acid conjugates with HIV-1 protease inhibitory activity. *Pharm. Res.* 1997, 14, 176–180.
10. Kim, D.-C.; Harrison, A. W.; Ruwart, M. J.; Wilkinson, K. F.; Fisher, J. F.; Hidalgo, I. J.; Borchardt, R. T. Evaluation of bile acid transporter in enhancing intestinal permeability of renin-inhibitory peptides. *J. Drug Targeting* 1993, 1, 347–359.
11. Kramer, W.; Wess, G.; Schubert, G.; Bickel, M.; Girbig, F.; Gutjahr, U.; Kowalewski, S.; Baringhaus, K.-H.; Enhsen, A.; Glombik, H.; Mullner, S.; Neckermann, G.; Schulz, S.; Petzinger, E. Liver-specific drug targeting by coupling to bile acids. *J. Biol. Chem.* 1992, 267, 18598–18604.
12. Kramer, W.; Wess, G.; Neckermann, G.; Schubert, G.; Fink, J.; Girbig, F.; Gutjahr, U.; Kowalewski, S.; Baringhaus, K.-H.; Boger, G.; Enhsen, A.; Falk, E.; Friedrich, M.; Glombik, H.; Hoffmann, A.; Pittius, C.; Urmann, M. Intestinal absorption of peptides by coupling to bile acids. *J. Biol. Chem.* 1994a, 269, 10621–10627.
13. Kramer, W.; Wess, G.; Enhsen, A.; Bock, K.; Falk, E.; Hoffmann, A.; Neckerman, G.; Gantz, D.; Schulz, S.; Nickau, L.; Petzinger, E.; Turley, S.; Dietschy, J. M. Bile acid derived HMG-CoA reductase inhibitors. *Biochim. Biophys. Acta* 1994b, 1227, 137–154.
14. Kramer, W.; Wess, G. Modified bile acid conjugates, and their use as pharmaceuticals. U.S. Pat. No. 5,462,933, 1995.
15. Kramer, W.; Wess, G. Bile acid conjugates of proline hydroxylase inhibitors. U.S. Pat. No. 5,646,272, 1997a.
16. Kramer, W.; Wess, G. Bile acid derivatives, processes for their preparation, and use as pharmaceuticals. U.S. Pat. No. 5,668,126, 1997b.
17. Kramer, W.; Stengelin, S.; Baringhaus, K.-H.; Enhsen, A.; Heuer, H.; Becker, W.; Corsiero, D.; Girbig, F.; Noll, R.; Weyland, C. Substrate specificity of the ileal and hepatic Na$^+$/bile acid cotransporters of the rabbit. I. Transport studies with membrane vesicles and cell lines expressing the cloned transporters. *J. Lipid Res.* 1999, 40, 1604–1617.
18. Kullak-Ublick, G. A.; Beuers, U.; Paumgartner, G. Hepatobiliary transport. *J. Hepatology* 2000, 32 (*Suppl.* 1), 3–18.
19. Larock's Comprehensive Organic Transformations (VCH Publishers Inc., 1989.
20. March's Advanced Organic Chemistry, (John Wiley and Sons, 4th Edition),
21. Navia, M. A.; Chaturvedi, P. R. Design principles for orally bioavailable drugs. *Drug Discovery Today* 1996, 1, 179–189.
22. Opsenica et al, 2000
23. Organic Reactions, Volumes 1–40 (John Wiley and Sons, 1991),
24. Petzinger, E.; Nickau, L.; Horz, J. A.; Schulz, S.; Wess, G.; Enhsen, A.; Falk, E.; Baringhaus, K.-H.; Glombik, H.; Hoffmann, A.; Mullner, S.; Neckermann, G.; Kramer, W. Hepatobiliary transport of hepatic 3-hydroxy-3-methylglutaryl coenzyme A reductase inhibitors conjugated with bile acids. *Hepatology* 1995, 22, 1801–1811.
25. Reiner, A. Process for preparing ursodeoxycholic acid derivatives and their inorganic and organic salts having therapeutic activity. Eur. Patent 0 272 462 B1, 1992.
26. Rodd's Chemistry of Carbon Compounds, Volumes 1–5 and Supplementals (Elsevier Science Publishers, 1989),
27. Swaan, P. W.; Szoka, F. C.; Oie, S. Use of the intestinal and hepatic bile acid transporters for drug delivery. *Adv. Drug Delivery Rev.* 1996, 20, 59–82.
28. Tsuji, A.; Tamai, I. Carrier-mediated intestinal transport of drugs. *Pharm. Res.* 1996, 13, 963–977.
29. U.S. Provisional Patent Application Ser. No. 60/238,758 of Gallop and Cundy, filed on Oct. 6, 2000
30. Satzinger, et al., "Cyclic Amino Acid" U.S. Pat. No. 4,024,175, May 17, 1977.
31. Silverman, et al., "GABA and L-glutamic Acid Analogs for Antiseizure Treatment", U.S. Pat. No. 5,563,175, Oct. 8, 1996.
32. Alexander, et al., "Acyloxyisopropyl Carbamates as Prodrugs for Amine Drug"s U.S. Pat. No. 5,684,018, Nov. 4, 1997.
33. Horwell, et al., "Bridged Cyclic Amino Acids as Pharmaceutical Agents", U.S. Pat. No. 6,020,370, Feb. 1, 2000.
34. Silverman, et al., "GABA and L-glutamine Acid Analogs for Antiseizure Treatment", U.S. Pat. No. 6,028,214, Feb. 22, 2000.

35. Horwell, et al., "Substituted Cyclic Amino Acids as Pharmaceutical Agents", U.S. Pat. No. 6,103,932, Aug. 15, 2000.
36. Silverman, et al., "GABA and L-glutamine Acid Analogs for Antiseizure Treatment", U.S. Pat. No. 6,117,906 Sep. 12, 2000.
37. WO 92/09560 Published: Jun. 11, 1992 GABA and L-glutamic Acid Analogs for Antiseizure Treatment
38. WO 93/23383 Published: Nov. 25, 1993 GABA and L-Glutamic Acid Analogs for Antiseizure Treatment
39. WO 97129101 Published: Aug. 14, 1997 Novel Cyclic Amino Acids as Pharmaceutical Agents
40. WO 97/33858 Published: Sep. 18, 1997 Novel Substituted Cyclic Amino Acids as Pharmaceutical Agents
41. WO 97/33859 Published: Sep. 18, 1997 Novel Bridged Cyclic Amino Acids As Pharmaceutical Agents
42. WO 98/17627 Published: Apr. 30, 1998 Substituted Gamma Aminobutyric Acids as Pharmaceutical Agents
43. WO 99108671 Published: Feb. 25, 1999 GABA analogs to prevent and treat gastrointestinal damage
44. WO 99/21824 Published: May 6, 1999 Cyclic Amino Acids and Derivatives Thereof Useful as Pharmaceutical Agents
45. WO 99/31057 Published: Jun. 24, 1999 4(3)Substituted-4(3)-Aminomethyl-(Thio)Pyran or Piperidine Derivatives (=Gabapentin Analogues), Their Preparation and Their Use in the Treatment of Neurological Disorders
46. WO 99/31074 Published: Jun. 24, 1999 Novel Amines as Pharmaceutical Agents
47. WO 99/31075 Published: Jun. 24, 1999 1-Substituted-1-Aminomethyl-Cycloalkane Derivatives (=Gabapentin Analogues), Their Preparation and Their Use in the Treatment of Neurological Disorders
48. WO 99/61424 Published: Dec. 2, 1999 Conformationally Constrained Amino Acid CompoundsHaving Affinity for the Alpha2Delta Subunit of a Calcium Channel
49. WO 00/15611 Published: Mar. 23, 2000 Branched Alkyl Pyrrolidine-3-Carboxylic Acids
50. WO 00/23067 Published: Apr. 27, 2000 Method for the Treatment of Mania
51. WO 00/31020 Published: Jun. 2, 2000 Improved Gamma Amino Butyric Acid Analogs
52. WO 00/50027 Published: Aug. 31, 2000 Gabapentin Derivative for Preventing and Treating Visceral Pain All of the above publications, patents and patent applications are herein incorporated by reference in their entirety to the same extent as if each individual publication, patent or patent application was specifically and individually indicated to be incorporated by reference in its entirety.

State of the Art

Rapid clearance of drugs from the systemic circulation represents a major impediment to effective clinical use of therapeutic and/or prophylactic compounds. Although multiple factors can influence the systemic concentrations of drugs achieved following oral administration (including drug solubility, dissolution rate, first-pass metabolism, p-glycoprotein and related efflux mechanisms, hepatic/renal elimination, etc), rapid systemic clearance is a particularly significant reason for suboptimal systemic exposure to many compounds. Rapid systemic clearance may require that large doses of drug be administered to achieve a therapeutic or prophylatic effect. Such larger doses of the drug, however, may result in greater variability in drug exposure, more frequent occurrence of side effects, or decrease in patient compliance. Frequent drug administration may also be required to maintain systemic drug levels above a minimum effective concentration. This problem is particularly significant for drugs that must be maintained in a well-defined concentration window to provide continuous therapeutic or prophylactic benefit while minimizing adverse effects (including for example, antibacterial agents, antiviral agents, anticancer agents, anticonvulsants, anticoagulants, etc.).

Conventional approaches to extend the systemic exposure of drugs with rapid clearance involve the use of formulation or device approaches that provide a slow or sustained release of drug within the intestinal lumen. These approaches are well known in the art and normally require that the drug be well absorbed from the large intestine, where such formulations are most likely to reside while releasing the drug. Drugs that are amenable to conventional sustained release approaches must be orally absorbed in the intestine and traverse this epithelial barrier by passive diffusion across the apical and basolateral membranes of the intestinal epithelial cells. The physicochemical features of a molecule that favor its passive uptake from the intestinal lumen into the systemic circulation include low molecular weight (e.g. <500 Da), adequate solubility, and a balance of hydrophobic and hydrophilic character (logP generally 1.5–4.0).[21]

Polar or hydrophilic compounds are typically poorly absorbed through an animal's intestine as there is a substantial energetic penalty for passage of such compounds across the lipid bilayers that constitute cellular membranes. Many nutrients that result from the digestion of ingested foodstuffs in animals, such as amino acids, di- and tripeptides, monosaccharides, nucleosides and water-soluble vitamins, are polar compounds whose uptake is essential to the viability of the animal. For these substances there exist specific mechanisms for active transport of the solute molecules across the apical membrane of the intestinal epithelia. This transport is frequently energized by co-transport of ions down a concentration gradient. Solute transporter proteins are generally single sub-unit, multi-transmembrane spanning polypeptides, and upon binding of their substrates are believed to undergo conformational changes which result in movement of the substrate(s) across the membrane.

Over the past 10–15 years, it has been found that a number of orally administered drugs are recognized as substrates by some of these transporter proteins, and that this active transport may largely account for the oral absorption of these molecules.[28] While in most instances the transporter substrate properties of these drugs were unanticipated discoveries made through retrospective analysis, it has been appreciated that, in principle, one might achieve good intestinal permeability for a drug by designing in recognition and uptake by a nutrient transport system. Drugs subject to active absorption in the small intestine are often unable to passively diffuse across epithelial cell membranes and are too large to pass through the tight junctions that exist between the intestinal cells. These drugs include many compounds structurally related to amino acids, dipeptides, sugars, nucleosides, etc. (for example, many cephalosporins, ACE inhibitors, AZT, gabapentin, pregabalin, baclofen, etc.)

Numerous structural analogs of γ-aminobutyric acid (GABA) (1) and L-glutamic acid have been described in the art as pharmaceutical agents.[30,32,34-53] Examples include gabapentin (2), pregabalin (3), vigabatrin (4), and baclofen (5) (see FIG. 1). Gabapentin was designed as a lipophilic GABA analog and was launched in 1994 as an anticonvulsant therapy for the treatment of epilepsy. During human trials and while in clinical use, it became apparent that gabapentin induced some other potentially useful therapeutic effects in chronic pain states and behavioral disorders. Gabapentin currently finds significant off-label use in clinical management of neuropathic pain. Pregabalin has been shown to have a similar pharmacological profile to gabapentin with greater potency in preclinical models of pain and epilepsy and is presently in Phase III clinical trials. It has been demonstrated that gabapentin, pregabalin, and related structural analogs are absorbed specifically in the small intestine by the large neutral amino acid transporter (LNAA).[8] Rapid systemic clearance of these compounds requires that they be dosed frequently to maintain a therapeutic or prophylactic concentration in the systemic circulation.[4] Conventional sustained release approaches have not been successfully applied to these drugs as they are not absorbed from the large intestine. Thus there is a significant need for effective sustained release versions of these drugs, particularly for the pediatric patient population, since drug must be administered during school hours, raising the issues of compliance, liability, and social acceptance.

One attractive pathway that might be exploitable for sustained oral delivery of drugs with rapid systemic clearance is the entero-hepatic circulation of bile acids.[27] Bile acids are hydroxylated steroids that play a key role in digestion and absorption of fat and lipophilic vitamins. After synthesis in the liver, they are secreted into bile and excreted by the gall bladder into the intestinal lumen where they emulsify and help solubilize lipophilic substances. Bile acids are conserved in the body by active uptake from the terminal ileum via the sodium-dependent transporter IBAT (or ASBT) and subsequent hepatic extraction by the transporter NTCP (or LBAT) located in the sinusoidal membrane of hepatocytes. This efficient mechanism to preserve the bile acid pool is termed the enterohepatic circulation (see FIG. 2). In man, the total bile acid pool (3–5 g) recirculates 6–10 times per day giving rise to a daily uptake of approximately 20–30 g of bile acids.

The high transport capacity of the bile acid pathway has been a key reason for interest in this system for drug delivery purposes. Several papers have postulated that chemical conjugates of bile acids with drugs could be used to provide liver site-directed delivery of a drug to bring about high therapeutic concentrations in the diseased liver with minimization of general toxic reactions elsewhere in the body; and gallbladder-site delivery systems of cholecystographic agents and cholesterol gallstone dissolution accelerators.[7] Several groups have explored these concepts in some detail, using the C-24 carboxylic acid, C-3, C-7, and C-12 hydroxyl groups of cholic acid (and other bile acids) as handles for chemically conjugating drugs or drug surrogates.[10,11]

The most rigorous drug targeting studies using the bile acid transport pathway to date relate to work with bile acid conjugates of HMG-CoA reductase inhibitors.[13,14,16,24] Coupling of the HMG-CoA reductase inhibitor HR 780 via an amide linkage to the C-3 position of cholate, taurocholate and glycocholate afforded substrates for both the ileal and liver bile acid transporter proteins (FIG. 3). Upon oral dosing of rats, the cholate conjugate S 3554 led to specific inhibition of HMG-CoA reductase in the liver, and in contrast to the parent compound HR 780, gave significantly reduced inhibition of the enzyme in extra-hepatic organs. Companion studies that looked at the tissue distribution of radiolabeled drugs two hours after i.v., administration through the mesenteric vein of rats also showed dramatically lower systemic levels for the bile acid conjugate relative to the parent. Because inhibition of HMG-CoA reductase requires the presence of the free carboxylic acid moiety in HR 780 this data was taken to indicate that S 3554 served as a prodrug of HR 780, undergoing hydrolysis (and other uncharacterized metabolism) in the rat liver. Interestingly, uptake of S 3554 by liver did not appear to depend on the liver bile acid transporter NTCP (which prefers taurocholate conjugates), but may instead have involved another multi-specific organic anion transport system on the sinusoidal hepatocyte membrane.

In summary, while the concept of harnessing the intestinal bile acid uptake pathway to enhance the absorption of poorly absorbed drugs is well appreciated, the existing art has merely demonstrated that bile acid-drug conjugates may be effectively trafficked to the liver and generally excreted into the bile, either unchanged or as some type of metabolite. The art gives no guidance as to how one prepares a composition that exploits the bile acid transport pathway and simultaneously provides therapeutically meaningful levels of a drug substance outside of the enterohepatic circulation. Furthermore, the art does not describe the potential use of the bile acid transport pathway to achieve a circulating reservoir of conjugated drug that is slowly released into the systemic circulation to provide sustained concentrations.

SUMMARY OF THE INVENTION

This invention is directed to the surprising discovery that the bile acid transport system can be utilized to provide sustained systemic concentrations of orally delivered drugs to an animal. This invention, therefore, permits sustained therapeutic or prophylactic systemic blood concentrations of orally delivered drugs such as GABA analogs which heretofore could not be achieved by oral administration.

Accordingly, in one of its method aspects, this invention is directed to a method for achieving sustained therapeutic or prophylactic blood concentrations of a GABA analog or an active metabolite thereof in the systemic circulation of an animal which method comprises orally administering to said animal a compound of formula (I):

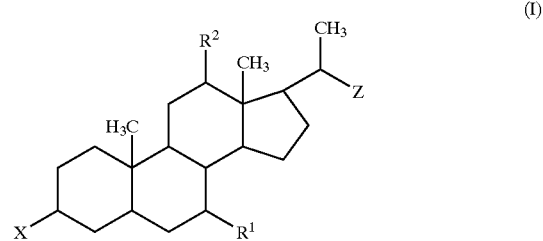

wherein:
$R^1$ and $R^2$ are independently hydrogen or hydroxy;
X is selected from the group consisting of hydroxy and D—$Q^a$—(T)— wherein:
T is —O— or —NH—;
$Q^a$ is a covalent bond or a linking group that cleaves under physiological conditions to release a GABA analog or active metabolite thereof into the systemic blood circulation of said animal, wherein said linker is not a linear oligopeptide consisting of 1, 2 or 3 α-amino acids and/or β-amino acids; and
D is a GABA analog moiety preferably of the formula:

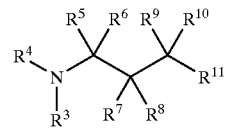

wherein:
$R^3$ is selected from the group consisting of hydrogen, an amino-protecting group, or a covalent bond linking the GABA analog moiety to $Q^a$;

$R^4$ is hydrogen, or $R^4$ and $R^9$ together with the atoms to which they are attached form a heterocyclic ring;

$R^5$ and $R^6$ are independently selected from the group consisting of hydrogen, alkyl, substituted alkyl, alkenyl, substituted alkenyl, alkynyl, aryl, substituted aryl, heteroaryl and substituted heteroaryl;

$R^7$ and $R^8$ are independently selected from the group consisting of hydrogen, alkyl, substituted alkyl, alkenyl, alkynyl, aryl, substituted aryl, heteroaryl and substituted heteroaryl, or $R^7$ and $R^8$ together with the atoms to which they are attached form a cycloalkyl, substituted cycloalkyl, heterocyclic or substituted heterocyclic ring;

$R^9$ is selected from the group consisting of hydrogen, alkyl, substituted alkyl, alkenyl, alkynyl, aryl, substituted aryl, heteroaryl and substituted heteroaryl;

$R^{10}$ is selected from the group consisting of hydrogen, alkyl, substituted alkyl, alkenyl, alkynyl, aryl, substituted aryl, heteroaryl and substituted heteroaryl;

$R^{11}$ is selected from the group consisting of carboxyl, amide, ester, sulfonamide, phosphonic acid, acidic heterocycle, sulfonic acid, hydroxamic acid and $C(O)R^{12}$;

$R^{12}$ is a covalent bond linking the GABA analog moiety to $Q^a$, provided only one of $R^3$ and $R^{12}$ links D to $Q^a$;

Z is selected from the group consisting of (a) a substituted alkyl group containing a moiety which is negatively charged at physiological pH which moiety is selected from the group consisting of —COOH, —SO$_3$H, —SO$_2$H, —P(O)(OR$^9$)(OH), —OP(O)(OR$^{19}$)(OH), —OSO$_3$H, wherein $R^9$ is selected from the group consisting of alkyl, substituted alkyl, aryl and substituted aryl; and (b) a group of the formula:

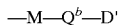

wherein:

M is selected from the group consisting of —CH$_2$OC(O)— and —CH$_2$CH$_2$C(O)—;

$Q^b$ is a covalent bond or a linking group which cleaves under physiological conditions to release a GABA analog or active metabolite thereof into the systemic blood circulation of said animal, wherein said linker is not a linear oligopeptide consisting of 1, 2 or 3 α-amino acids and/or β-amino acids; and D' is a GABA analog moiety preferably of the formula:

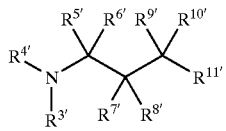

wherein:

$R^{3'}$ is selected from the group consisting of hydrogen, an amino-protecting group, or a covalent bond linking the moiety to $Q^b$;

$R^{4'}$ is hydrogen, or $R^{4'}$ and $R^{9'}$ together with the atoms to which they are attached form a heterocyclic ring;

$R^{5'}$ and $R^{6'}$ are independently selected from the group consisting of hydrogen, alkyl, substituted alkyl, alkenyl, substituted alkenyl, alkynyl, aryl, substituted aryl, heteroaryl and substituted heteroaryl;

$R^{7'}$ and $R^{8'}$ are independently selected from the group consisting of hydrogen, alkyl, substituted alkyl, alkenyl, alkynyl, aryl, substituted aryl, heteroaryl and substituted heteroaryl, or $R^{7'}$ and $R^{8'}$ together with the atoms to which they are attached form a cycloalkyl, substituted cycloalkyl, heterocyclic or substituted heterocyclic ring;

$R^{9'}$ is selected from the group consisting of hydrogen, alkyl, substituted alkyl, alkenyl, alkynyl, aryl, substituted aryl, heteroaryl and substituted heteroaryl;

$R^{10'}$ is selected from the group consisting of hydrogen, alkyl, substituted alkyl, alkenyl, alkynyl, aryl, substituted aryl, heteroaryl and substituted heteroaryl;

$R^{11'}$ is selected from the group consisting of carboxylic acid, carboxylic amide, carboxylic ester, sulfonamide, phosphonic acid, acidic heterocycle, sulfonic acid, hydroxamic acid and $C(O)R^{12'}$;

$R^{12'}$ is a covalent bond linking the GABA analog moiety to $Q^b$, provided only one of $R^{3'}$ and $R^{12'}$ links D to $Q^b$; or a pharmaceutically acceptable salt thereof;

provided that when X is hydroxy, then Z is a group of the formula —M—$Q^b$—D'.

Preferably $R^1$ and $R^2$ are both α-OH; or $R^1$ is β-OH and $R^2$ is hydrogen; or $R^1$ is α-OH and $R^2$ is hydrogen; or $R^1$ is hydrogen and $R^2$ is α-OH; or $R^1$ is β-OH and $R^2$ is α-OH; or $R^1$ and $R^2$ are both hydrogen.

X has either alpha or beta substitution relative to the A ring of the sterol.

Preferably, D—$Q^a$—(T)— and/or —M—$Q^b$—D' are selected to cleave under physiological conditions at a rate to provide a therapeutic and/or prophylactic blood concentration of the GABA analog or active metabolite thereof in the animal for a period of at least about 10% longer (more preferably at least 50% longer and still more preferably at least 100% longer) than when the GABA analog is orally delivered by itself at an equivalent dose.

The selection of D—$Q^a$—(T)— and/or —M—$Q^b$—D' are preferably made relative to the activity, specificity and localization of enzymatic activity within tissues that comprise the enterohepatic circulation such that the drug is released at a site from where it is made available to the systemic circulation. For example, in one preferred embodiment, D—$Q^a$—(T)— and/or —M—$Q^b$—D' are selected to contain one or more ester groups that permit cleavage of such groups by endogenous esterases within such tissues. In another preferred embodiment, D—$Q^a$—(T)— and/or —M—$Q^b$—D' are selected to contain one or more amide groups which amide groups permit cleavage of such groups by endogenous proteases. It will be appreciated by one skilled in the art that when M or T is linked to a GABA analog (D) above via an amido group compounds of formula I are provided wherein $Q^a$ or $Q^b$ is a covalent bond and hydrolysis of this bond in vivo provides for release of the GABA analog or active metabolite thereof.

Alternatively, $Q^a$ and/or $Q^b$ can be derived from a linker compound having complementary reactive groups which covalently link the GABA analog to the bile acid. FIGS. 4 through 8 illustrate examples of suitable linking groups $Q^a$ and $Q^b$, where the linker is not a linear oligopeptide consisting of 1, 2 or 3 α-amino acids and/or β-amino acids. Particularly preferred examples of suitable cleavable linkers for use in this invention include structures of formulae (i) through (v) as shown below;

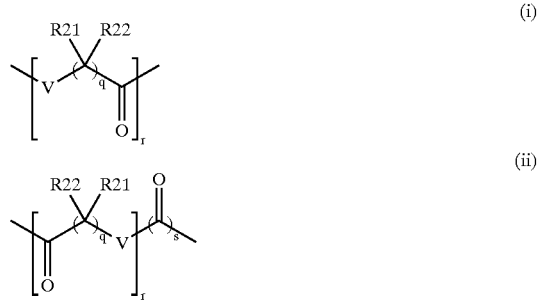

-continued

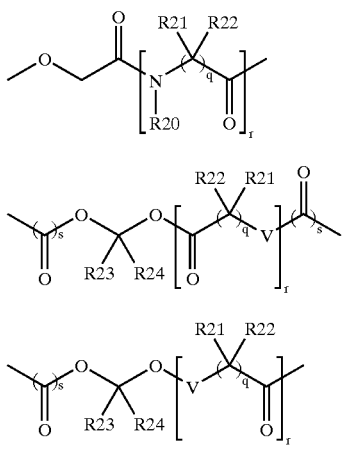
(iii)

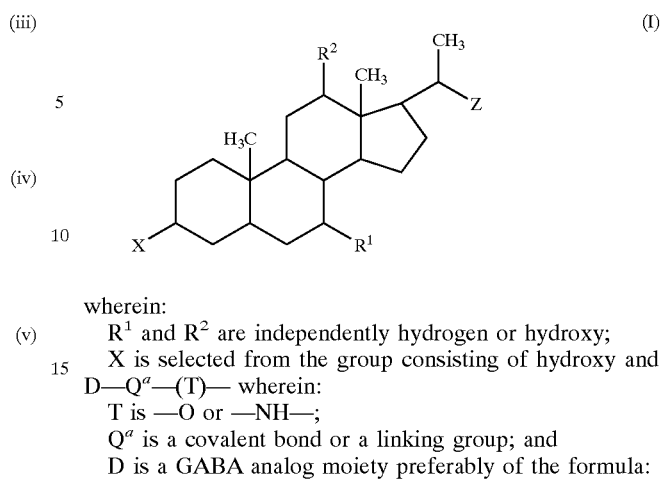
(iv)

(v)

wherein:
V is selected from the group consisting of $NR^{20}$, O, S and $CR^{21}R^{22}$;
each s is independently 0 or 1;
r is 0, 1, 2, 3 or 4;
q is 1, 2, 3, 4, 5 or 6;
each $R^{20}$ is independently hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl;
each $R^{21}$ and $R^{22}$ is independently hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{21}$ and $R^{22}$ together with the atoms to which they are attached form a cycloalkyl, substituted cycloalkyl, heterocyclyl or substituted heterocyclyl ring, or, when $R^{20}$ and $R^{22}$ are present and are on adjacent atoms, then together with the atoms to which they are attached form a heterocyclyl or substituted heterocyclyl ring;
each $R^{23}$ and $R^{24}$ are independently hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{23}$ and $R^{24}$ together with the atoms to which they are attached form a cycloalkyl, substituted cycloalkyl, heterocyclyl or substituted heterocyclyl ring;
provided that when $Q^a$ and/or $Q^b$ is of formulae (i) or (ii), then when each V is $NR^{20}$ and each q is 1 or 2 then r is not 1, 2 or 3.

Preferred release rates of the GABA analog in each cycle are from 5% to 95% and, more preferably, 10% to 95%.

When low release rates of the GABA analog or active metabolite are employed, the continuous circulation of the compound of formula (I) allows for sustained release of the GABA analog or an active metabolite thereof by oral administration regardless of whether the GABA analog is completely or incompletely absorbed into the systemic blood circulation.

The methods of this invention are preferably achieved by use of compounds of formula (I). Accordingly, in one of its composition aspects, this invention is directed to compounds of formula (I):

(I)

wherein:
$R^1$ and $R^2$ are independently hydrogen or hydroxy;
X is selected from the group consisting of hydroxy and D—$Q^a$—(T)— wherein:
T is —O or —NH—;
$Q^a$ is a covalent bond or a linking group; and
D is a GABA analog moiety preferably of the formula:

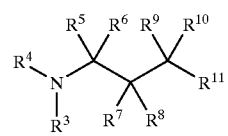

wherein:
$R^3$ is selected from the group consisting of hydrogen, an amino-protecting group, or a covalent bond linking the moiety to $Q^a$;
$R^4$ is hydrogen, or $R^4$ and $R^9$ together with the atoms to which they are attached form a heterocyclic ring;
$R^5$ and $R^6$ are independently selected from the group consisting of hydrogen, alkyl, substituted alkyl, alkenyl, substituted alkenyl, alkynyl, aryl, substituted aryl, heteroaryl and substituted heteroaryl;
$R^7$ and $R^8$ are independently selected from the group consisting of hydrogen, alkyl, substituted alkyl, alkenyl, alkynyl, aryl, substituted aryl, heteroaryl and substituted heteroaryl, or $R^7$ and $R^8$ together with the atoms to which they are attached form a cycloalkyl, substituted cycloalkyl, heterocyclic or substituted heterocyclic ring;
$R^9$ is selected from the group consisting of hydrogen, alkyl, substituted alkyl, alkenyl, alkynyl, aryl, substituted aryl, heteroaryl and substituted heteroaryl;
$R^{10}$ is selected from the group consisting of hydrogen, alkyl, substituted alkyl, alkenyl, alkynyl, aryl, substituted aryl, heteroaryl and substituted heteroaryl;
$R^{11}$ is selected from the group consisting of carboxylic acid, carboxylic amide, carboxylic ester, sulfonamide, phosphonic acid, acidic heterocycle, sulfonic acid, hydroxamic acid and $C(O)R^{12}$;
$R^{12}$ is a covalent bond linking the GABA analog moiety to $Q^a$, provided only one of $R^3$ and $R^{12}$ links D to $Q^a$;
Z is selected from the group consisting of (a) a substituted alkyl group containing a moiety which is negatively charged at physiological pH which moiety is selected from the group consisting of —COOH, —SO$_3$H, —SO$_2$H, P(O)(OR$^{19}$)(OH), OP(O)(OR$^{19}$)(OH), —OSO$_3$H, wherein $R^{19}$ is selected from the group consisting of alkyl, substituted alkyl, aryl and substituted aryl; and (b) a group of the formula:

—M—$Q^b$—D' wherein:
M is selected from the group consisting of —CH$_2$OC(O)— and —CH$_2$CH$_2$C(O)—;

$Q^b$ is a covalent bond or a linking group which may cleave under physiological conditions to release a GABA analog or active metabolite thereof into the systemic blood circulation of said animal; and D' is a GABA analog moiety preferably of the formula:

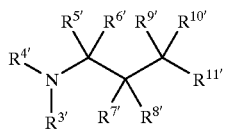

wherein:

$R^{3'}$ is selected from the group consisting of hydrogen, an amino-protecting group, or a covalent bond linking the GABA analog to $Q^b$;

$R^{4'}$ is hydrogen or $R^{4'}$ and $R^{9'}$ together with the atoms to which they are attached form a heterocyclic ring;

$R^{5'}$ and $R^{6'}$ are independently selected from the group consisting of hydrogen, alkyl, substituted alkyl, alkenyl, substituted alkenyl, alkynyl, aryl, substituted aryl, heteroaryl and substituted heteroaryl;

$R^{7'}$ and $R^{8'}$ are independently selected from the group consisting of hydrogen, alkyl, substituted alkyl, alkenyl, alkynyl, aryl, substituted aryl, heteroaryl and substituted heteroaryl, or $R^{7'}$ and $R^{8'}$ together with the atoms to which they are attached form a cycloalkyl, substituted cycloalkyl, heterocyclic or substituted heterocyclic ring;

$R^{9'}$ is selected from the group consisting of hydrogen, alkyl, substituted alkyl, alkenyl, alkynyl, aryl, substituted aryl, heteroaryl and substituted heteroaryl;

$R^{10'}$ is selected from the group consisting of hydrogen, alkyl, substituted alkyl, alkenyl, alkynyl, aryl, substituted aryl, heteroaryl and substituted heteroaryl;

$R^{11'}$ is selected from the group consisting of carboxylic acid, carboxylic amide, carboxylic ester, sulfonamide, phosphonic acid, acidic heterocycle, sulfonic acid, hydroxamic acid and $C(O)R^{12'}$;

$R^{12'}$ is a covalent bond linking the GABA analog moiety to $Q^b$, provided only one of $R^{3'}$ and $R^{12'}$ links D to $Q^b$; or a pharmaceutically acceptable salt thereof;

provided that when X is hydroxy, then Z is a group of the formula —M—$Q^b$—D'; and further provided that when X is hydroxy, M is —CH$_2$CH$_2$C(O)—, $Q^b$ is a covalent bond and $R^{11'}$ is carboxylic acid, then at least one of $R^{5'}$, $R^{6'}$, $R^{7'}$, $R^{8'}$, $R^{9'}$ and $R^{10'}$ is other than hydrogen.; and yet further provided that neither $Q^a$ nor $Q^b$ is a linear oligopeptide comprised exclusively of 1, 2 or 3 α-amino acids and/or β-amino acids.

While the above compounds include those wherein X is D—$Q^a$—(T)— and Z is —M—$Q^b$—D', it is preferred that for compounds where Z is —M—$Q^b$—D' then X is hydroxy. Similarly, it is preferred that for compounds where X is D—$Q^a$—(T)— then Z is selected from the group consisting of —CH$_2$CH$_2$—COOH; —CH$_2$CH$_2$C(O)NHCH$_2$COOH and —CH$_2$CH$_2$C(O)NHCH$_2$CH$_2$SO$_3$H.

A particularly preferred group of compounds of Formula (I) is represented by Formula (II) shown below:

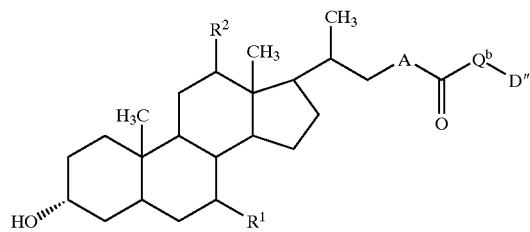

(II)

wherein:
$R^1$ and $R^2$ are both α-OH;
$R^1$ is β-OH and $R^2$ is hydrogen;
$R^1$ is α-OH and $R^2$ is hydrogen;
$R^1$ is hydrogen and $R^2$ is α-OH;
$R^1$ is β-OH and $R^2$ is α-OH; or
$R^1$ and $R^2$ are both hydrogen;
A is —O— or —CH$_2$—;
D'' is a GABA analog moiety preferably selected from the group consisting of:

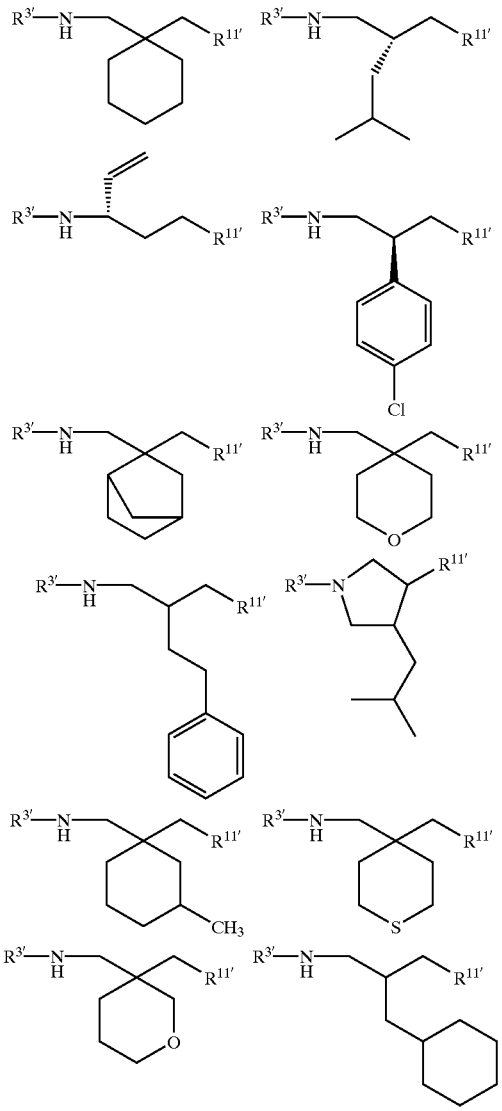

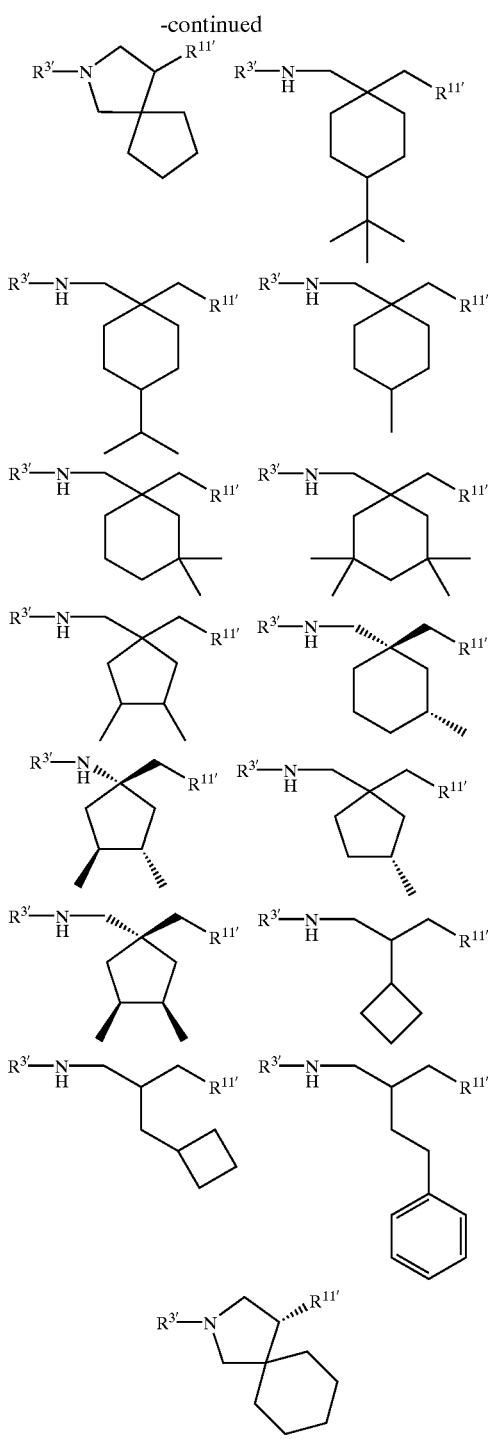

wherein:
R[3'] and R[11'] are defined above; and
Q[b] is a covalent bond or a linker which may cleave under physiological conditions to release said GABA analog or an active metabolite thereof thereby providing a therapeutic or prophylactic systemic blood concentration of said GABA analog or an active metabolite thereof in said animal, wherein said linker is not a linear oligopeptide consisting of 1, 2 or 3 α-amino acids and/or β-amino acids; or
a pharmaceutically acceptable salt thereof.
Preferably, R[11'] is CO$_2$H, CO$_2$Na or other pharmaceutically acceptable carboxylate salt.

Preferably, Q[b] is selected to provide a therapeutic and/or prophylactic blood concentration in said animal for a period of at least about 10% longer (more preferably at least 50% longer and still more preferably at least 100% longer) than when the GABA analog is orally delivered by itself at an equivalent dose.

Preferably, Q[b] is a covalent bond and D'' is linked via the amine to form an amido bond which cleaves under physiological conditions to release the GABA analog.

When Q[b] is a linker, it is preferably from 1–11 atoms in length. More preferably, Q[b] is a group of formula:

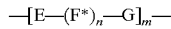

wherein:
m is an integer of from 1 to 4;
n is 0 or 1;
E is —NH— or —O—;
F* is selected from a group consisting of alkylene, substituted alkylene, alkenylene, substituted alkenylene, alkynylene, substituted alkynylene, cycloalkylene, substituted cycloalkylene, cycloalkenylene, substituted cycloalkenylene, arylene, substituted arylene, heteroarylene, substituted heteroarylene, heterocyclene and substituted heterocyclene; and G is —OC(O)—, —C(O)— or —NH—.

Preferably, F* is selected from a group consisting of alkylene, alkenylene, alkynylene and alkylene substituted with a group selected from the group consisting of —COOH, —SO$_3$H, —SO$_2$H, P(O)(OR$^{19}$)(OH), OP(O)(OR$^{19}$)(OH), —OSO$_3$H, wherein R$^{19}$ is selected from the group consisting of alkyl, substituted alkyl, aryl and substituted aryl; and where one, two or three methylene groups are optionally replaced by a carboxy (—C(O)O—) group.

More preferably, Q[b] is a covalent bond or a cleavable group selected from the group consisting of structures of formulae (vi) to (x):

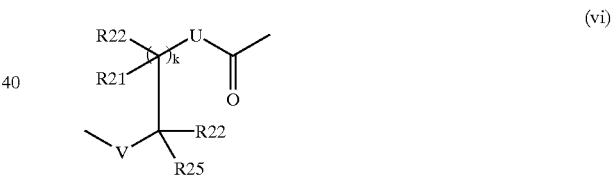

(vi)

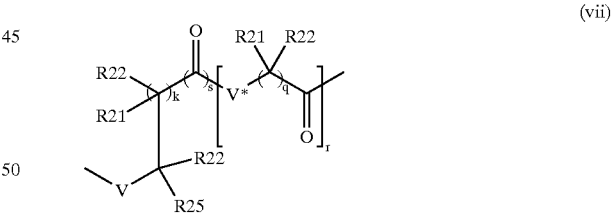

(vii)

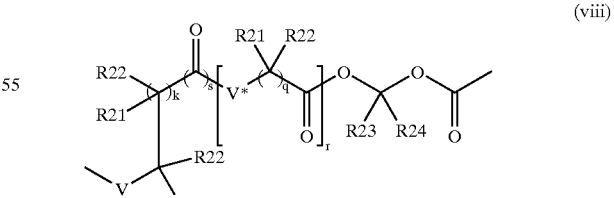

(viii)

(ix)

-continued (x)

wherein:
V and V* are independently $NR^{20}$, O, S or $CR^2R^{22}$;
U is $NR^{20}$, O, S; $R^{25}$ is $R^{21}$ or $(CR^{21}R^{22})_1Z$;
Z is selected from the group consisting of $CO_2H$, $SO_3H$, $OSO_3H$, $SO_2H$, $P(O)(OR^{19})(OH)$, $OP(O)(OR^{19})(OH)$;
s is 0 or 1;
r is 0, or 2;
k is 0, 1, 2, 3 or 4;
each q is 1, 2, 3, 4, 5 or 6;
l is 0 or 1;
$R^{19}$ is selected from the group consisting of alkyl, substituted alkyl, substituted aryl and substituted aryl;
$R^{20}$, $R^{21}$ and $R^{22}$ are independently hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{21}$ and $R^{22}$ together with the atoms to which they are attached form a cycloalkyl, substituted cycloalkyl, heterocyclyl or substituted heterocyclyl ring, or, when $R^{20}$ and $R^{22}$ are present and are on adjacent atoms, then together with the atoms to which they are attached form a heterocyclyl or substituted heterocyclyl ring;
$R^{23}$ and $R^{24}$ are independently hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{23}$ and $R^{24}$ together with the atoms to which they are attached form a cycloalkyl, substituted cycloalkyl, heterocyclyl or substituted heterocyclyl ring;
provided that when $Q^b$ is of formula (vii), V and V* are $NR^{20}$, s is 1, k is 0 or 1, each q is either 1 or 2, and r is 0, 1 or 2 then $R^{25}$ is Z.

Preferably, A is —$CH_2$—.

In another embodiment, a preferred group of compounds of Formula (I) are represented by Formula (IIIa) which is shown below:

(IIIa)

wherein:
$R^1$ and $R^2$ are both α-OH; $R^1$ is β-OH and $R^2$ is hydrogen; $R^1$ is α-OH and $R^2$ is hydrogen; $R^1$ is hydrogen and $R^2$ is α-OH; $R^1$ is β-OH and $R^2$ is α-OH; or $R^1$ and $R^2$ are both hydrogen;
T is —O— or —NH— and is either α- or β-;
D is a GABA analog moiety preferably selected from the group consisting of:

-continued

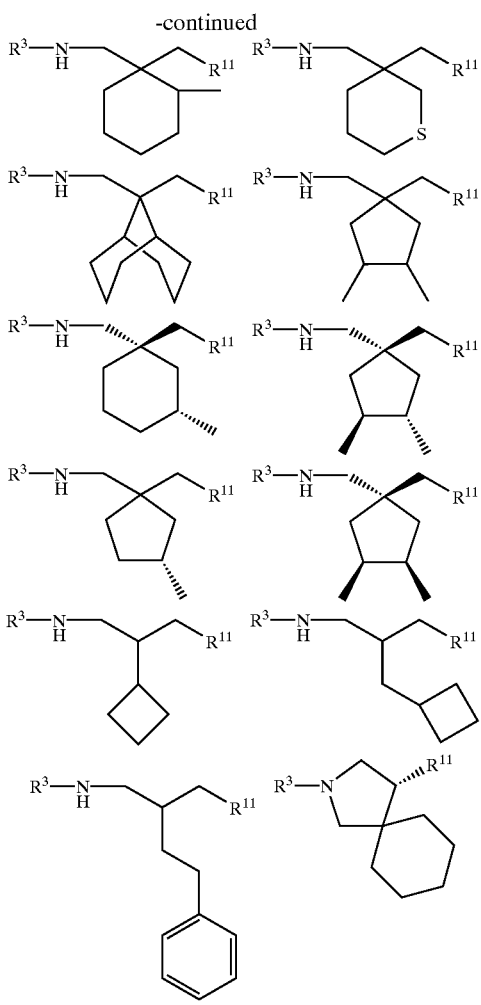

wherein R[3] is defined above and R[11] is carboxylate or C(O)R[12], wherein R[12] is a covalent bond linking D to Q', provided that only one of R[3] and R[12] is a covalent bond linking D to Q'; and Q' is a covalent bond or a linker which may cleave under physiological conditions to release said GABA analog or an active metabolite thereof thereby providing a therapeutic or prophylactic systemic blood concentration of said GABA analog or an active metabolite thereof in said animal, wherein said linker is not a linear oligopeptide consisting of 1, 2 or 3 α-amino acids and/or β-amino acids;

R[13] is a substituted alkyl group containing a moiety which is negatively charged at physiological pH which moiety is selected from a group consisting of —COOH, —SO$_3$H, —SO$_2$H, P(O)(OR[19])(OH), OP(O)(OR[19])(OH), —OSO$_3$H, wherein R[19] is selected from the group consisting of alkyl, substituted alkyl, aryl and substituted aryl; or a pharmaceutically acceptable salt thereof.

Preferably, R[13] is —CH$_2$CH$_2$CO$_2$H, —CH$_2$CH$_2$C(O)NHCH$_2$COOH or —CH$_2$CH$_2$C(O)NH(CH$_2$)$_2$SO$_3$H or a sodium salt of the acid groups.

Preferably, Q' is selected to provide a therapeutic and/or prophylactic blood concentration in said animal for a period of at least about 10% longer (more preferably at least 50% longer and still more preferably at least 100% longer) than when the GABA analog is orally delivered by itself at an equivalent dose.

More preferably, Q' is a covalent bond that cleaves to release the GABA analog.

Still more preferably, Q' is 1–20 atoms in length. More preferably, Q' is a group of the formula:

$$—E'—(F')_{n1}—G'—$$

wherein:
n1 is 0 or 1;
G' is —C(O)—, alkylene, —O—C(O)—, —NRC(O)— where R is hydrogen, alkyl or substituted alkyl;
F' is selected from a group consisting of a covalent bond, alkylene, substituted alkylene, alkenylene, substituted alkenylene, alkynylene, substituted alkynylene, cycloalkylene, substituted cycloalkylene, cycloalkenylene, substituted cycloalkenylene, arylene, substituted arylene, heteroarylene, substituted heteroarylene, heterocyclene and substituted heterocyclene; and
E' is a covalent bond, —C(O)O— or —C(O)—.

More preferably, Q' is a cleavable covalent bond or a group selected from the group consisting of —C(O)— and the structures of formulae (i) through (v) as shown below;

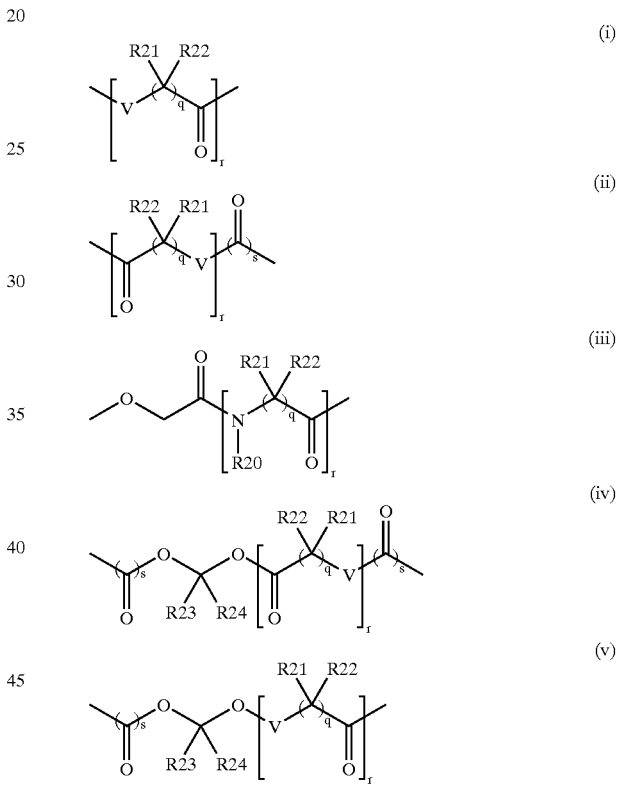

wherein:
V is selected from the group consisting of NR[20], O, S and CR[21]R[22];
each s is independently 0 or 1;
r is 0, 1, 2, 3 or 4;
each q is 1, 2, 3, 4, 5 or 6;
each R[20] is independently hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl;
each R[21] and R[22] is independently hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R[21] and R[22] together with the atoms to which they are attached form a cycloalkyl, substituted cycloalkyl, heterocyclyl or substituted heterocyclyl ring, or, when $R^{20}$ and $R^{22}$ are present and are on adjacent atoms, then together with the atoms to which they are attached form a heterocyclyl or substituted heterocyclyl ring;

each $R^{23}$ and $R^{24}$ are independently hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{23}$ and $R^{24}$ together with the atoms to which they are attached form a cycloalkyl, substituted cycloalkyl, heterocyclyl or substituted heterocyclyl ring;

provided that when Q' is of formulae (i) or (ii), then when each V is $NR^{20}$ and each q is 1 or 2 then r is not 1, 2 or 3.

In yet another embodiment, a preferred group of compounds of Formula (I) are represented by Formula (IIIb) shown below:

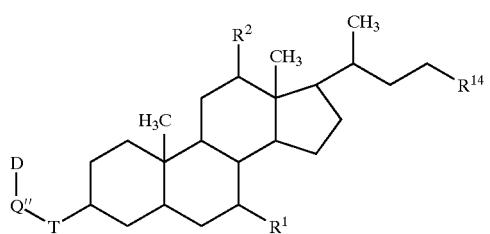

(IIIb)

wherein:

$R^1$ and $R^2$ are both α-OH; $R^1$ is β-OH and $R^2$ is hydrogen; $R^1$ is α-OH and $R^2$ is hydrogen; $R^1$ is hydrogen and $R^2$ is α-OH; $R^1$ is β-OH and $R^2$ is α-OH; or $R^1$ and $R^2$ are both hydrogen;

T is —O— or —NH— and is either alpha or beta;

D is a GABA analog moiety preferably selected from the group consisting of:

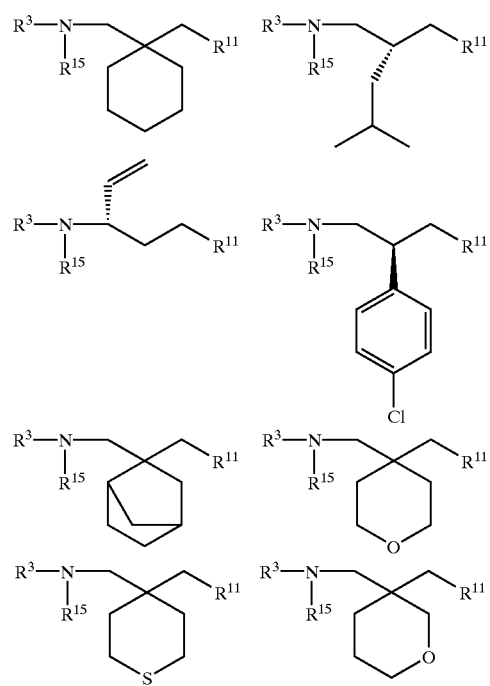

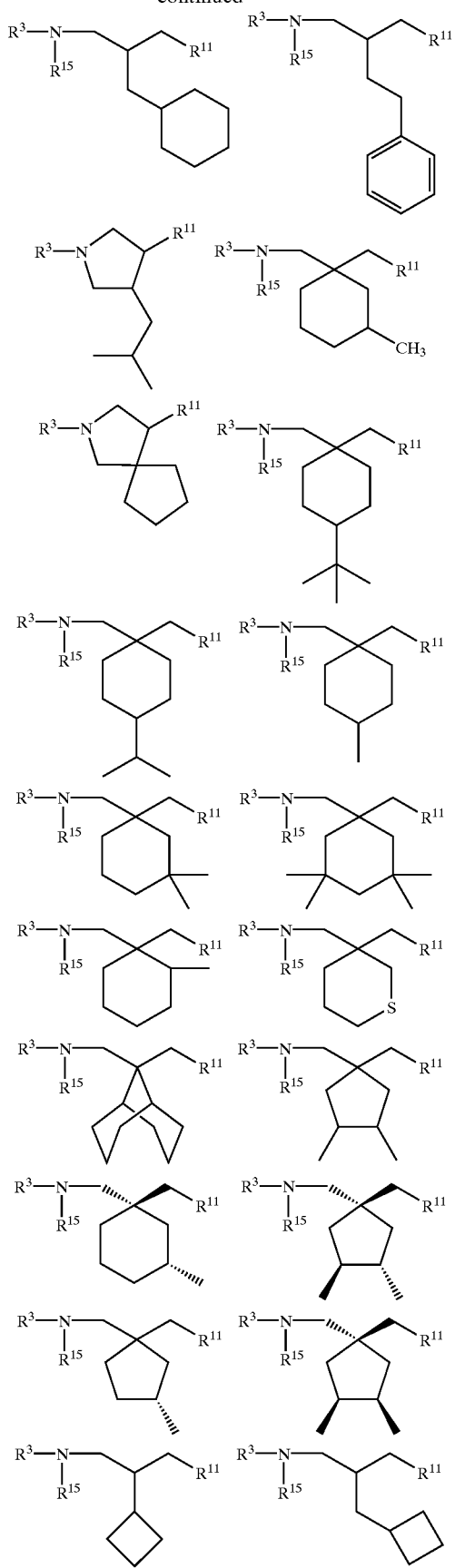

-continued

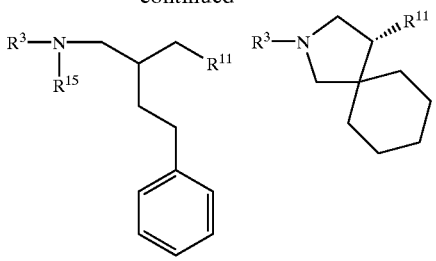

wherein:

$R^3$ and $R^{11}$ are defined above;

$R^{15}$ is hydrogen or an amino protecting group which is hydrolysable in vivo; and Q" is a covalent bond or a linker which may cleave under physiological conditions to release said GABA analog or an active metabolite thereof thereby providing a therapeutic or prophylactic systemic blood concentration of said GABA analog or an active metabolite thereof in said anima, wherein said linker is not a linear oligopeptide consisting of 1, 2 or 3 α-amino acids and/or β-amino acids 1;

$R^{14}$ is carboxyl or alkylamido substituted with a substituent selected from the group consisting of —COOH, —SO$_3$H, —SO$_2$H, P(O)(OR$^{19}$)(OH), OP(O)(OR$^{19}$)(OH), —OSO$_3$H, wherein $R^{19}$ is selected from the group consisting of alkyl, substituted alkyl, aryl and substituted aryl; or a pharmaceutically acceptable salt thereof.

Preferably, $R^{14}$ is carboxyl, —C(O)NHCH$_2$CO$_2$H, or —C(O)NH(CH$_2$)$_2$SO$_3$H or a sodium salt of the acid groups.

Preferably, $R^{15}$ is hydrogen, —C(O)—O-R$^{16}$ where $R^{16}$ is alkyl, more preferably methyl, ethyl, or —C(O)(CR$^{21}$R$^{22}$)NHR$^{20}$ where $R^{20}$, $R^{21}$ and $R^{22}$ are defined as above.

Preferably, Q" is selected to provide a therapeutic and/or prophylactic blood concentration in said animal for a period of at least about 10% longer (more preferably at least 50% longer and still more preferably at least 100% longer) than when the GABA analog is orally delivered by itself.

Preferably, Q" is a covalent bond that cleaves to release the GABA analog.

Preferably, Q" is a cleavable covalent bond or a group selected from —C(O)— and the structures of formulae (i) through (v) as shown below;

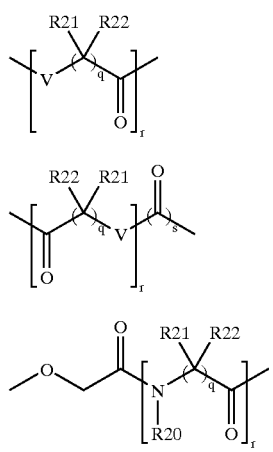

(i)

(ii)

(iii)

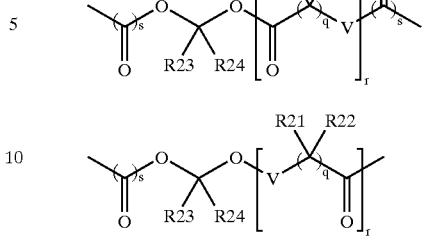

(iv)

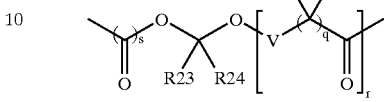

(v)

wherein:

V is selected from the group consisting of NR$^{20}$, O, S and CR$^{21}$R$^{22}$;

each s is independently 0 or 1;

r is 0, 1, 2, 3 or 4;

q is 1, 2, 3, 4, 5 or 6;

each $R^{20}$ is independently hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl;

each $R^{21}$ and $R^{22}$ is independently hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{21}$ and $R^{22}$ together with the atoms to which they are attached form a cycloalkyl, substituted cycloalkyl, heterocyclyl or substituted heterocyclyl ring, or, when $R^{20}$ and $R^{22}$ are present and are on adjacent atoms, then together with the atoms to which they are attached form a heterocyclyl or substituted heterocyclyl ring;

each $R^{23}$ and $R^{24}$ are independently hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{23}$ and $R^{24}$ together with the atoms to which they are attached form a cycloalkyl, substituted cycloalkyl, heterocyclyl or substituted heterocyclyl ring;

provided that when Q" is of formulae (i) or (ii), then when each V is NR$^{20}$ and each q is 1 or 2 then r is not 1, 2 or 3.

Particularly preferred compounds of Formula IIIa and Formula IIIb are those selected from the group consisting of:

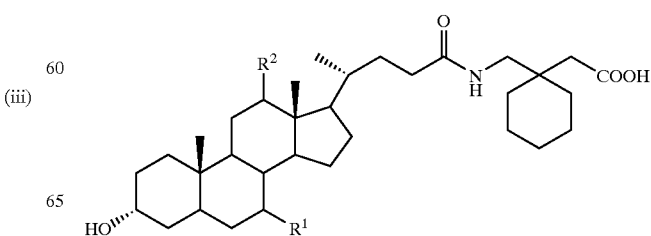

-continued
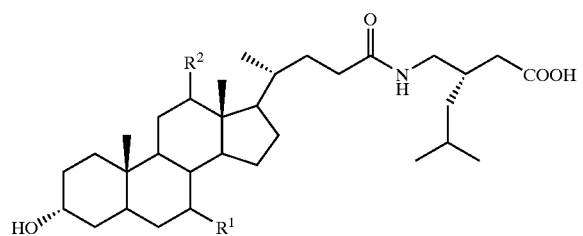
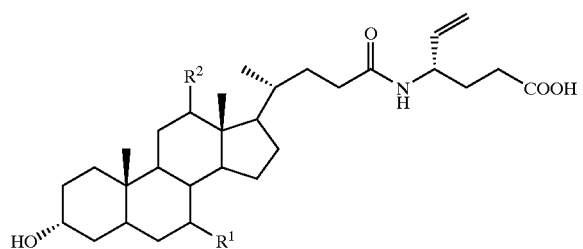
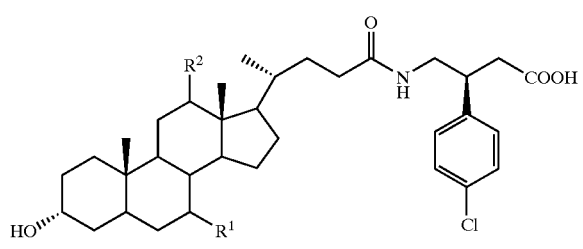
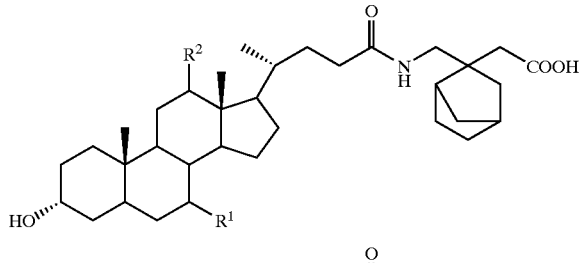
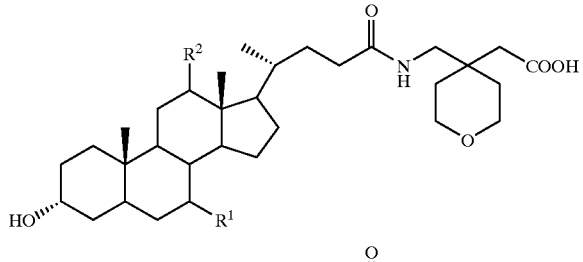
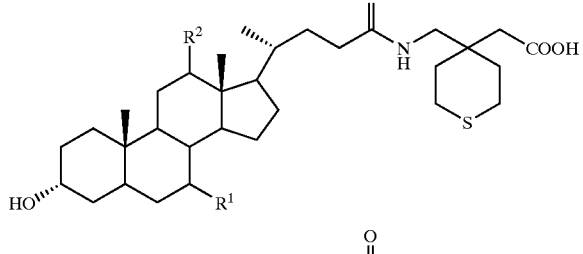
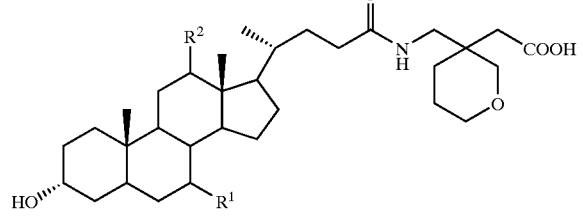
-continued
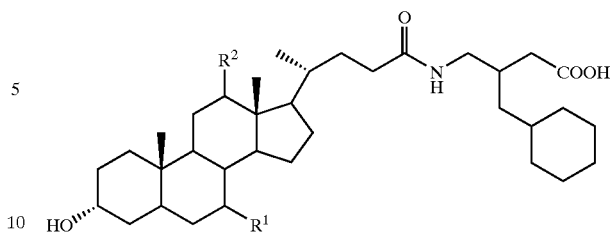
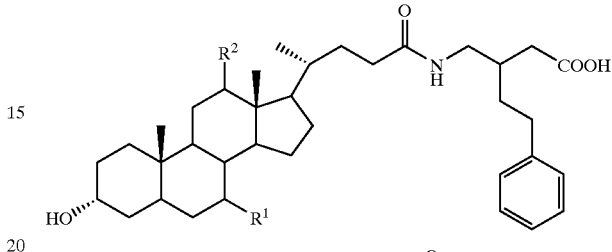
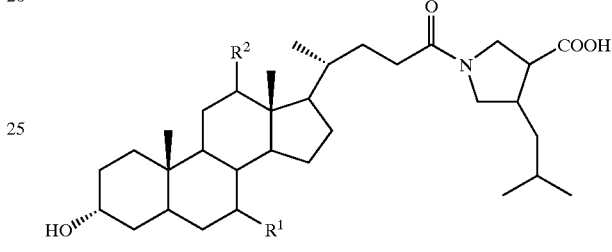
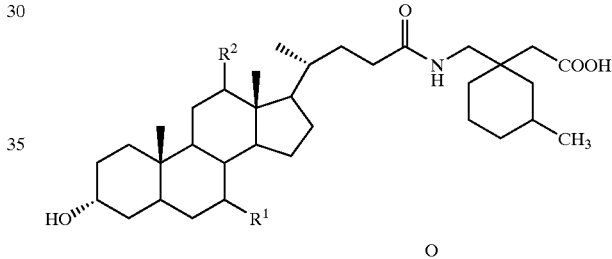
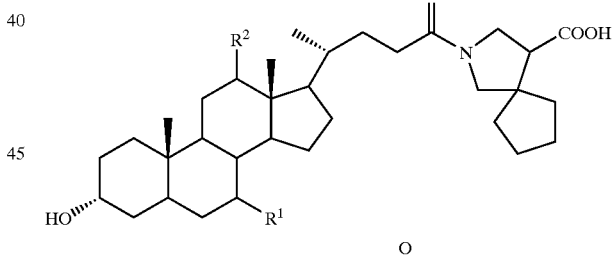
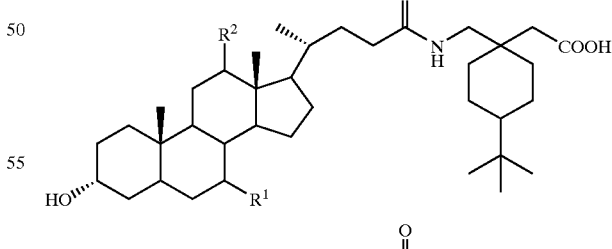
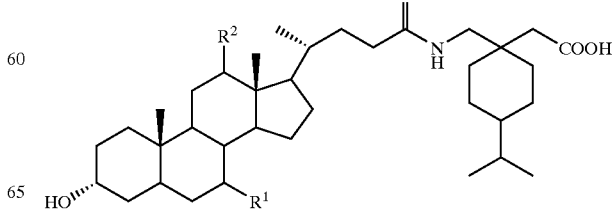

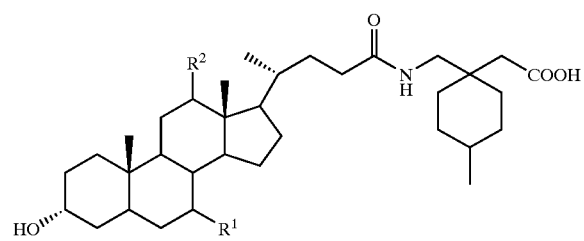
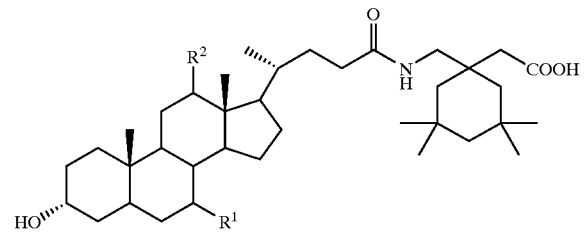
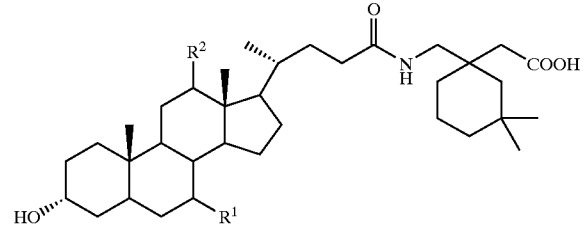
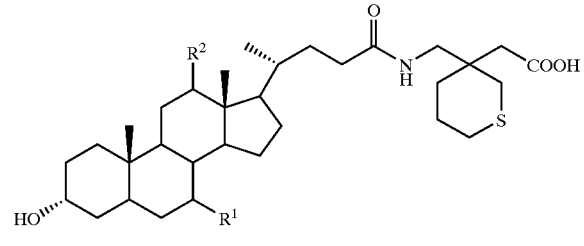
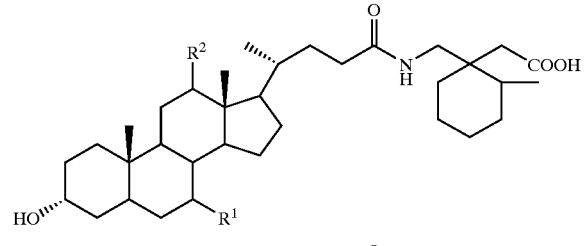
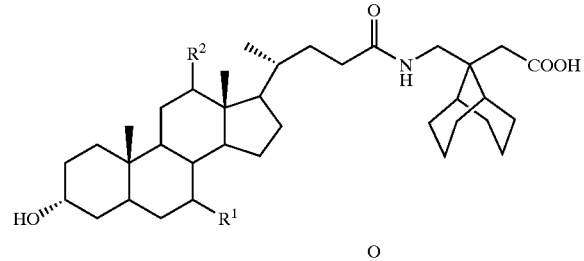
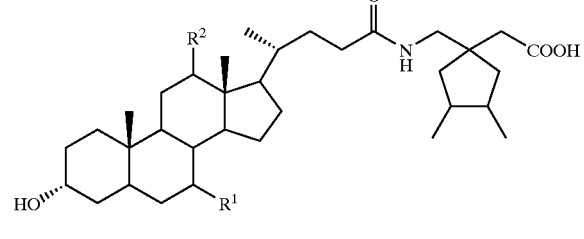
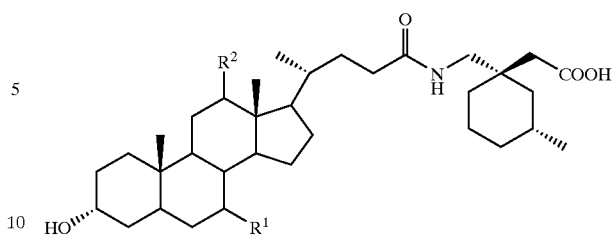
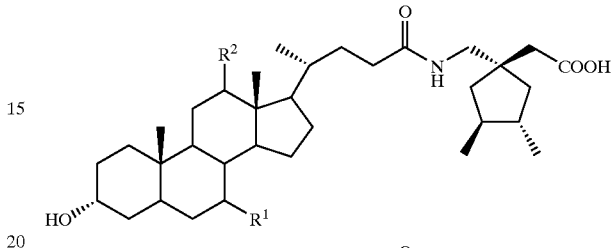
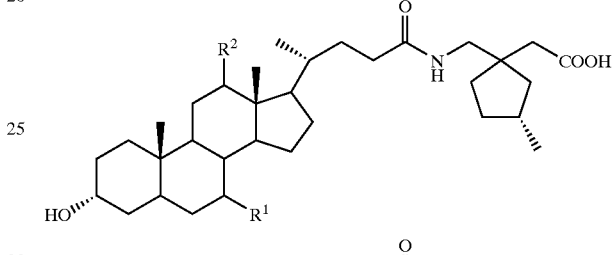
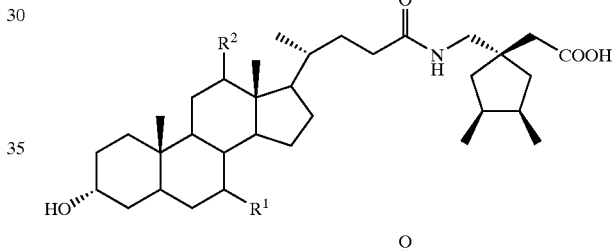
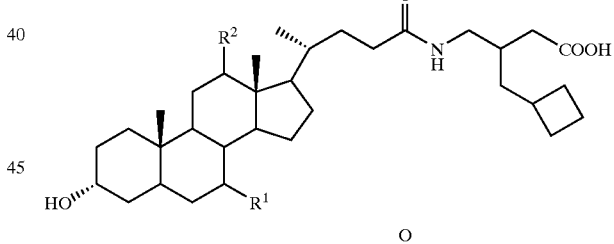
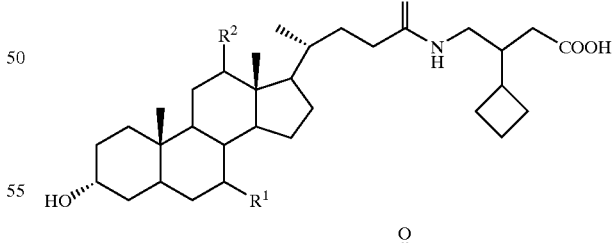
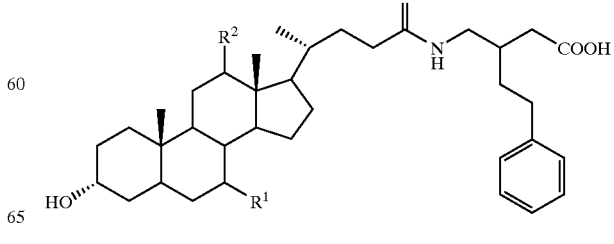

-continued

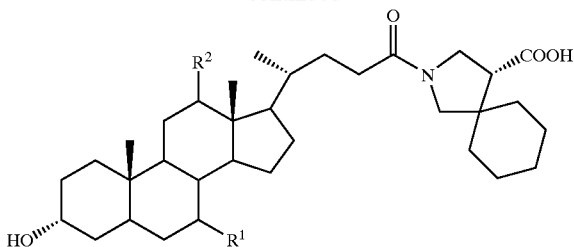

wherein:
$R^1$ and $R^2$ are as defined above; or
pharmaceutically acceptable salts thereof.

The compounds described above are preferably administered as pharmaceutical compositions comprising the drug/cleavable linker/transporter compounds described above and a pharmaceutically acceptable excipient.

For compounds of Formula I where X is hydroxyl and compounds of Formula II, the moiety —$Q^b$—D' or —$Q^b$—D" when taken together most preferably contains a moiety which is negatively charged at physiological pH, located from 5 to 15 atoms from C-22 of the bile acid nucleus, which moiety is selected from the group consisting Of $CO_2H$, $SO_3H$, $OSO_3H$, $SO_2H$, $P(O)(OR^{19})(OH)$, $OP(O)(OR^{19})(OH)$ and pharmaceutically acceptable salts thereof, wherein $R^{19}$ is defined above.

Particularly preferred compounds can be further represented as structures of Formulae (V)–(XV) illustrated in FIGS. 4–6, where each of $R^1$, $R^2$, $R^{5'}$, $R^{6'}$, $R^{7'}$, $R^{8'}$, $R^{9'}$, $R^{10'}$ and $R^{11'}$ are as defined in the Summary of the Invention.

Particularly preferred compounds can be further represented as structures of Formulae (XVI)–(XXVI) illustrated in FIGS. 7 and 8, where each of $R^1$, $R^2$, $R^4$, $R^5$, $R^6$, $R^7$, $R^8$, $R^9$, $R^{10}$, $R^{11}$, $R^{5'}$, $R^{6'}$, $R^{7'}$, $R^{8'}$, $R^{9'}$ and $R^{10'}$ are as defined in the Summary of the Invention.

Compounds of the formulae (V)–(XXVI) contain a variety of cleavable linker functionalities (attached to GABA analogs including amide linkages [compounds (V)–(IX), (XX), (XXII), (XXIV) and (XXVI); carbamate linkages [compounds (X)–(XII), (XVII) and (XXIII)]; acyloxyalkyl carbamate linkages [compounds (XIII)–(XV), (XXI) and (XXV)] as well as compounds that have two different linkages that must be cleaved to release the drug [compounds (XVI)–(XVII)].

The compounds described above are preferably administered as pharmaceutical compositions comprising the drug/cleavable linker/transporter compounds described above and a pharmaceutically acceptable excipient.

BRIEF DESCRIPTION OF THE DRAWINGS

FIG. 3 illustrates the prior art HMG-CoA reductase inhibitor HR 780 as well as prior art conjugates employing the lactone-Opened ring of HR 780 coupled to a bile acid.

FIGS. 4–6 illustrate bile acids with modified C-17 side chains that are especially preferred compounds of formula (I–II).

DETAILED DESCRIPTION OF THE INVENTION

Figure 1:
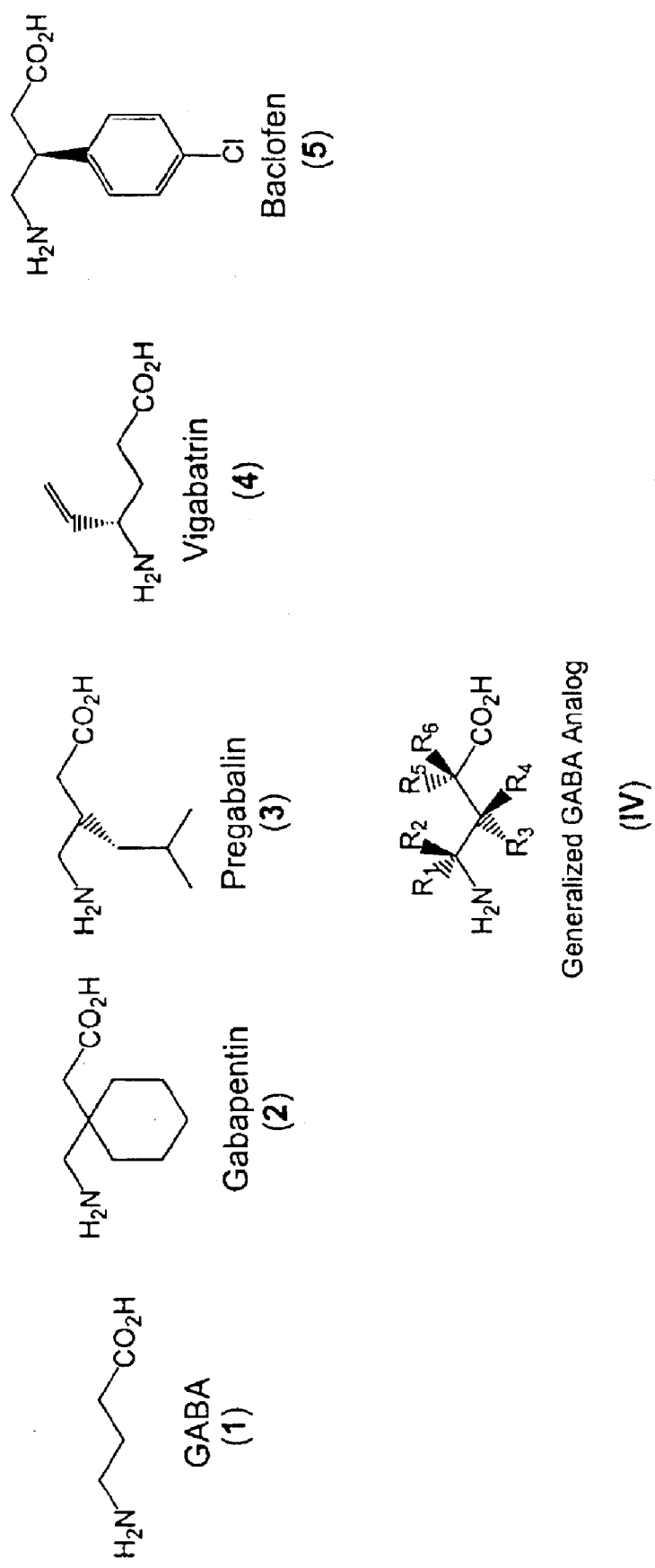
FIG. 1 illustrates structural analogs of γ-aminobutyric acid (GABA).
Figure 2:
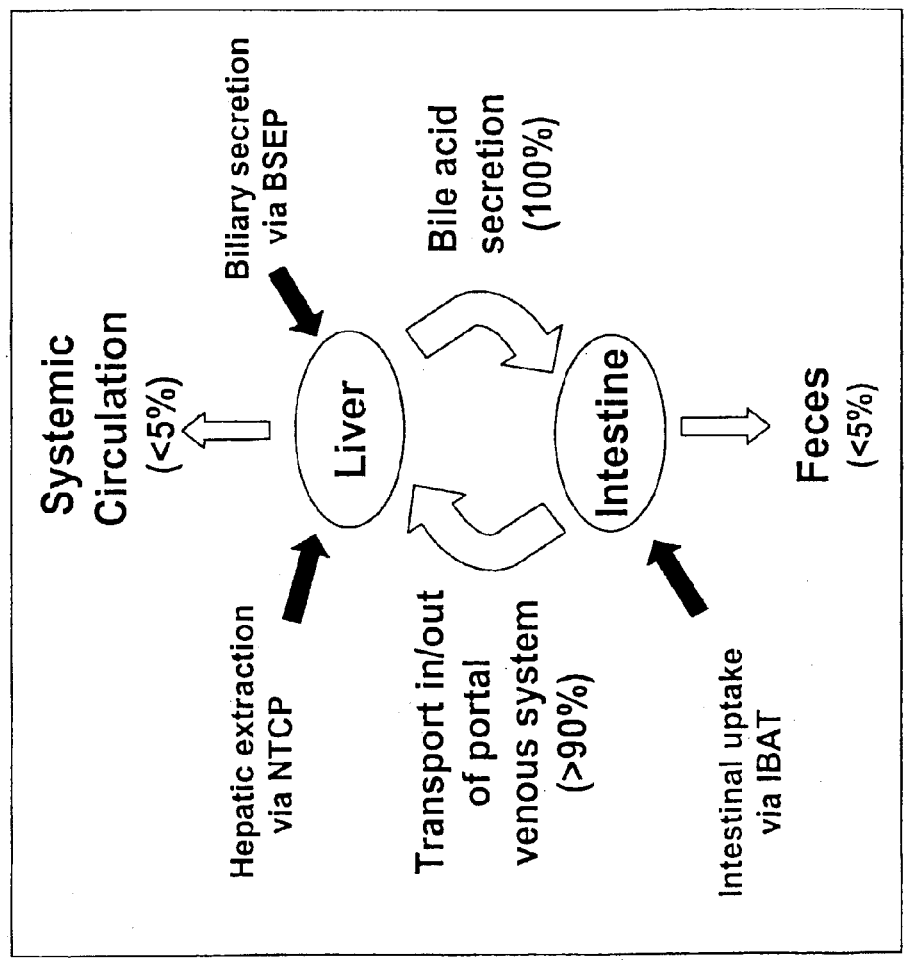
FIG. 2 illustrates the enterohepatic circulation with key transporter proteins identified which mediate bile acid circulation.
Figure 4:
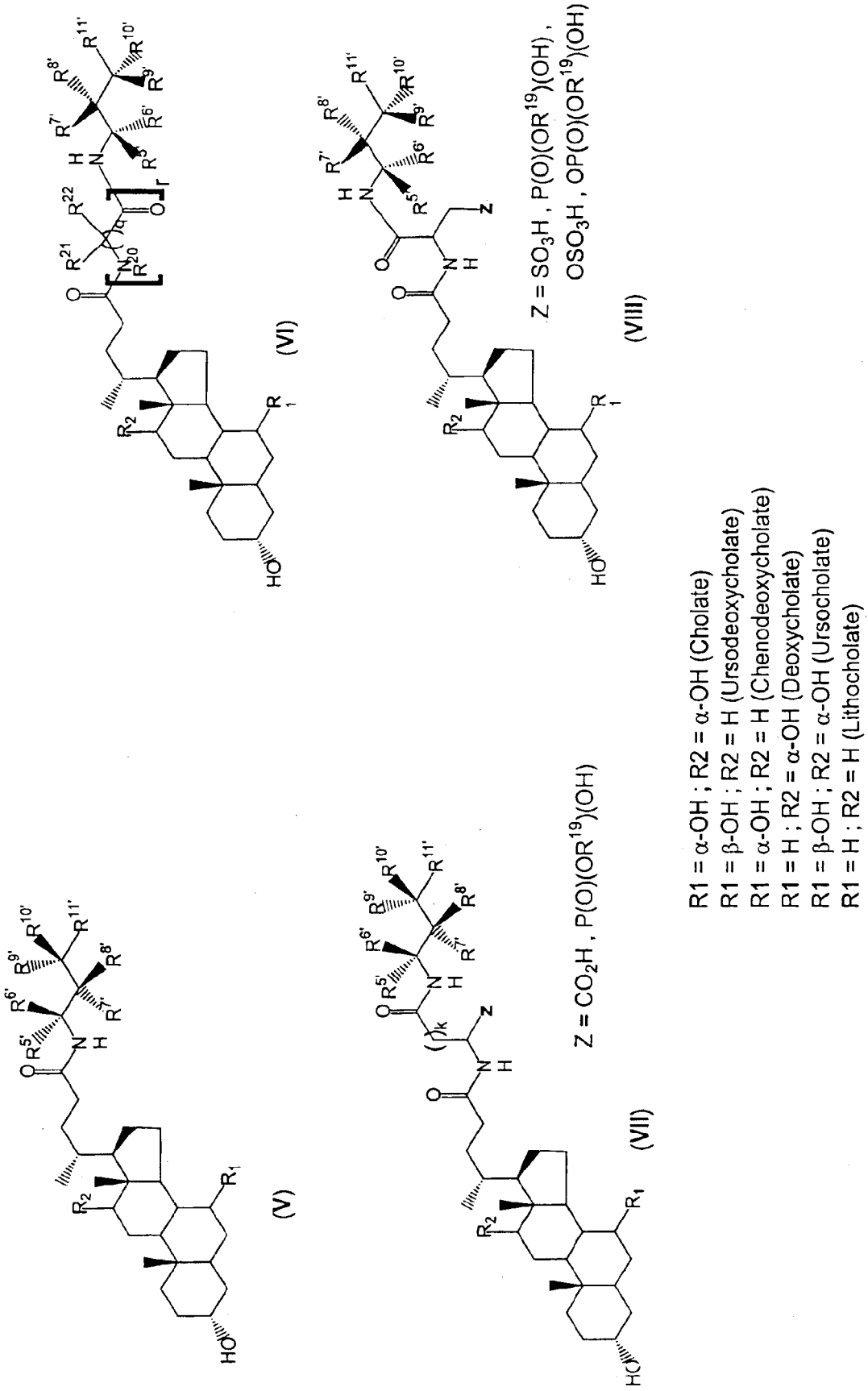
Figure 5:
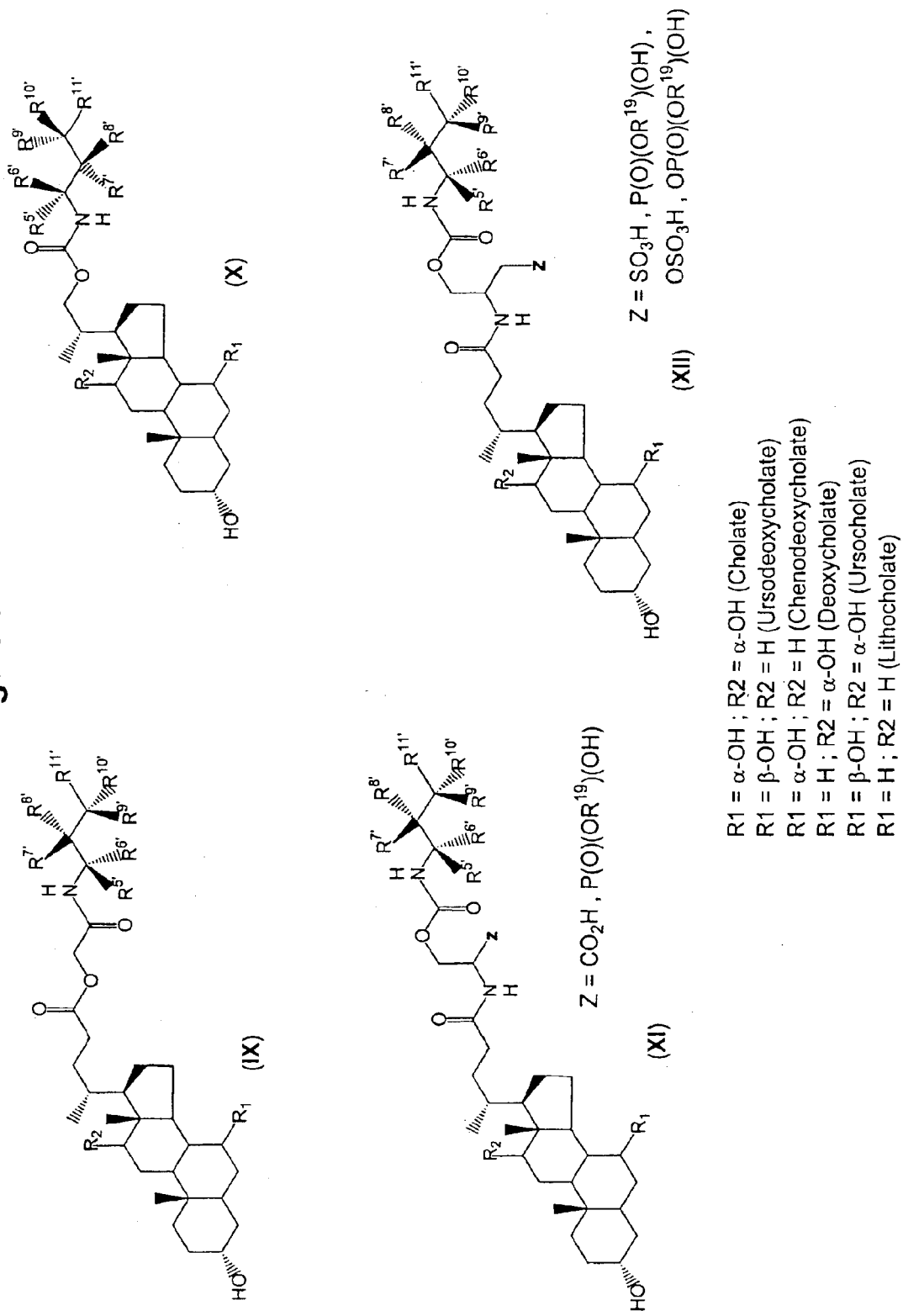
Figure 7:
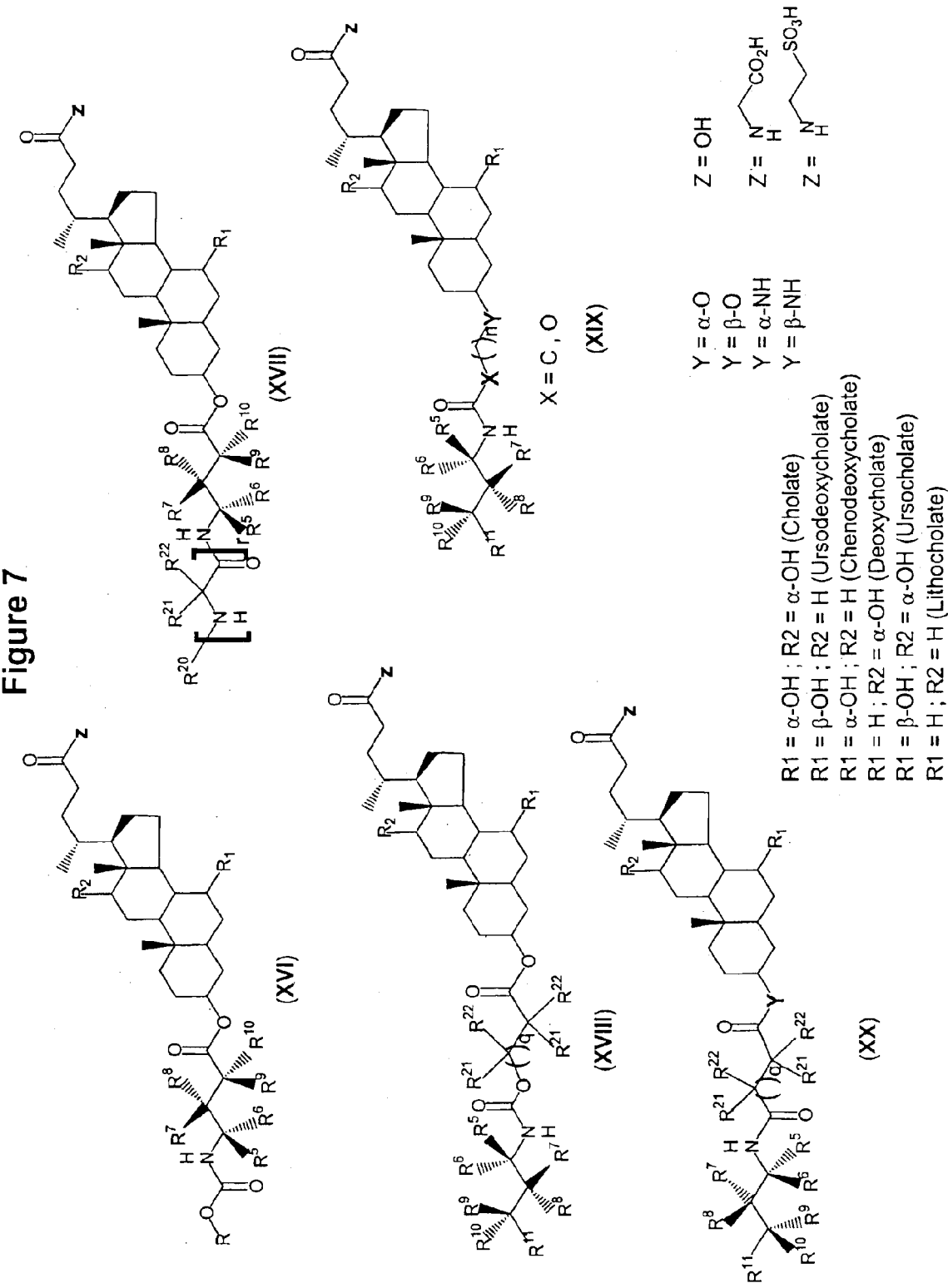
FIGS. 7 and 8 illustrate 3-substituted bile acids that are especially preferred compounds of formula (I–III).
Figure 8:
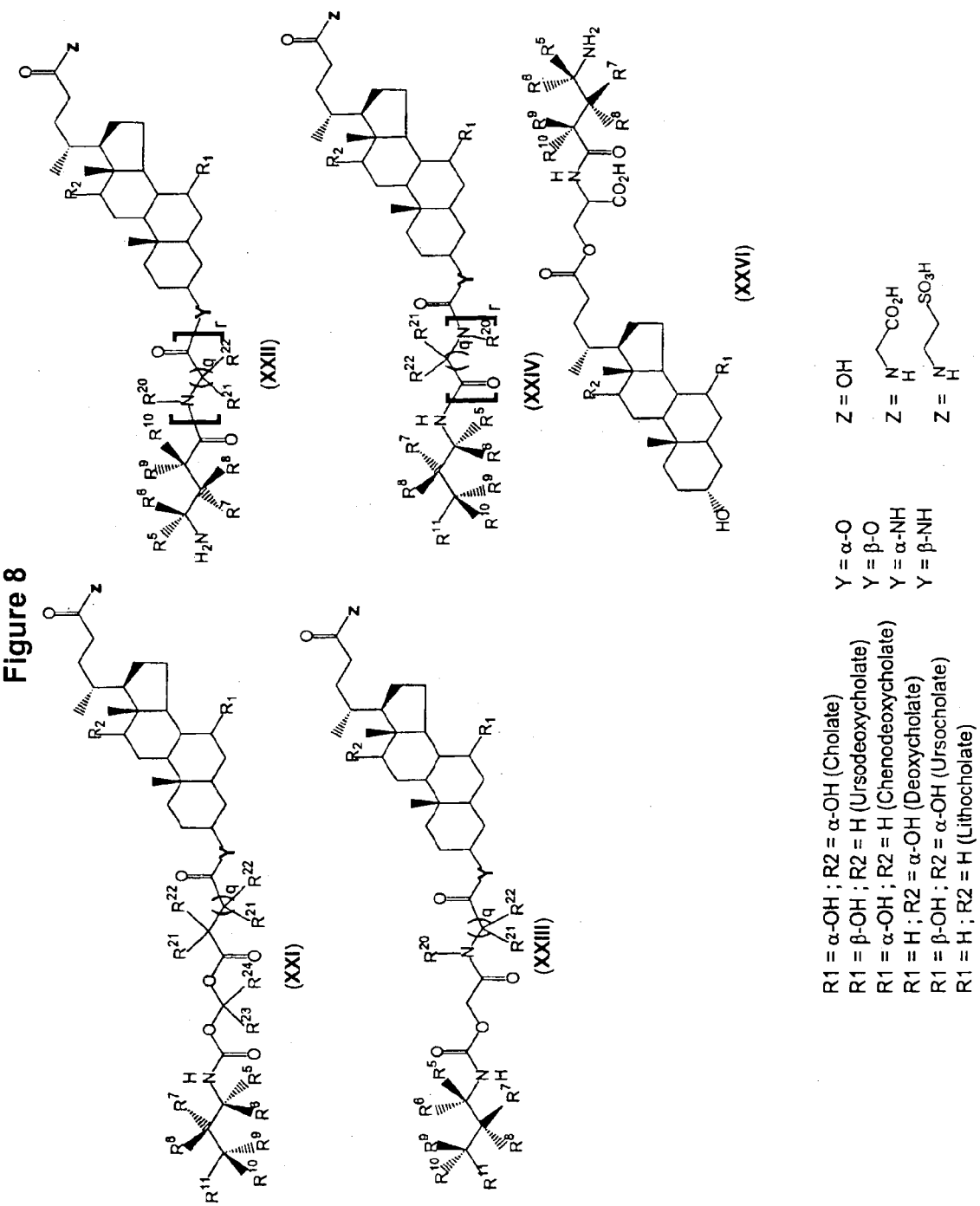

This invention is directed to methods for providing sustained systemic concentrations of therapeutic or prophylactic agents following oral administration to animals. This invention is also directed to compounds and pharmaceutical compositions that are used in such methods. However, prior to describing this invention in further detail, the following terms will first be defined:

Definitions

As used herein, the term "animal" refers to various species such as mammalian and avian species including, by way of example, humans, cattle, sheep, horses, dogs, cats, turkeys, chicken, and the like. Preferably, the animal is a mammal and even more preferably is a human.

"GABA analog" preferably refers to a compound of one of the following formulae:

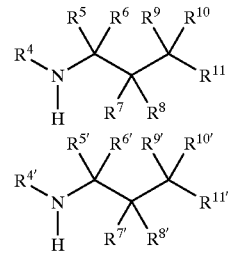

wherein
$R^4$ is hydrogen, or $R^4$ and $R^9$ together with the atoms to which they are attached form a heterocyclic ring;
$R^5$ and $R^6$ are independently selected from the group consisting of hydrogen, alkyl, substituted alkyl, alkenyl, substituted alkenyl, alkynyl, aryl, substituted aryl, heteroaryl and substituted heteroaryl;
$R^7$ and $R^8$ are independently selected from the group consisting of hydrogen, alkyl, substituted alkyl, alkenyl, alkynyl, aryl, substituted aryl, heteroaryl and substituted heteroaryl, or $R^7$ and $R^8$ together with the atoms to which they are attached form a cycloalkyl, substituted cycloalkyl, heterocyclic or substituted heterocyclic ring;
$R^9$ is selected from the group consisting of hydrogen, alkyl, substituted alkyl, alkenyl, alkynyl, aryl, substituted aryl, heteroaryl and substituted heteroaryl;
$R^{10}$ is selected from the group consisting of hydrogen, alkyl, substituted alkyl, alkenyl, alkynyl, aryl, substituted aryl, heteroaryl and substituted heteroaryl;
$R^{11}$ is selected from the group consisting of carboxyl, amide, ester, sulfonamide, phosphonic acid, acidic heterocycle, sulfonic acid, hydroxamic acid and $C(O)R^{12}$;
$R^{12}$ is a covalent bond linking the GABA analog moiety to $Q^a$, provided only one of $R^3$ and $R^{12}$ links D to $Q^a$
$R^{4'}$ is hydrogen, or $R^{4'}$ and $R^{9'}$ together with the atoms to which they are attached form a heterocyclic ring;
$R^{5'}$ and $R^{6'}$ are independently selected from the group consisting of hydrogen, alkyl, substituted alkyl, alkenyl, substituted alkenyl, alkynyl, aryl, substituted aryl, heteroaryl and substituted heteroaryl;

R[7'] and R[8'] are independently selected from the group consisting of hydrogen, alkyl, substituted alkyl, alkenyl, alkynyl, aryl, substituted aryl, heteroaryl and substituted heteroaryl, or R[7'] and R[8'] together with the atoms to which they are attached form a cycloalkyl, substituted cycloalkyl, heterocyclic or substituted heterocyclic ring;

R[9'] is selected from the group consisting of hydrogen, alkyl, substituted alkyl, alkenyl, alkynyl, aryl, substituted aryl, heteroaryl and substituted heteroaryl;

R[10'] is selected from the group consisting of hydrogen, alkyl, substituted alkyl, alkenyl, alkynyl, aryl, substituted aryl, heteroaryl and substituted heteroaryl;

R[11'] is selected from the group consisting of carboxylic acid, carboxylic amide, carboxylic ester, sulfonamide, phosphonic acid, acidic heterocycle, sulfonic acid, hydroxamic acid and C(O)R[12];

R[12'] is a covalent bond linking the GABA analog moiety to $Q^b$, provided only one of R[3'] and R[12'] links D to $Q^b$.

"Orally delivered drugs" refer to drugs which are administered to an animal in an oral form, preferably, in a pharmaceutically acceptable diluent. Oral delivery includes ingestion of the drug as well as oral gavage of the drug.

"Systemic bioavailability" refers to the rate and extent of systemic exposure to a drug or a metabolite thereof as reflected by the area under the systemic blood concentration versus time curve.

"Translocation across the intestinal wall" refers to movement of a drug or drug conjugate by a passive or active mechanism, or both, across an epithelial cell membrane of any region of the gastrointestinal tract.

"Active metabolite of a drug" refers to products of in vivo modification of the compound of formula (I–IIIa and b) which have therapeutic or prophylactic effect.

"Therapeutic or prophylactic blood concentrations" refers to systemic exposure to a sufficient concentration of a drug or an active metabolite thereof over a sufficient period of time to effect disease therapy or to prevent the onset or reduce the severity of a disease in the treated animal.

"Treating" a particular disease or disorder means reducing the number of symptoms and/or severity of symptoms of the disease, and/or reducing or limiting the further progression of the disease.

"Preventing" a disease or disorder means preventing or inhibiting the onset or occurrence of the disease or disorder.

"Sustained release" refers to release of a drug or an active metabolite thereof into the systemic circulation over a prolonged period of time relative to that achieved by oral administration of a conventional formulation of the drug.

"Tissue of the enterohepatic circulation" refers to the blood, plasma, intestinal contents, intestinal cells, liver cells, biliary tract or any fraction, suspension, homogenate, extract or preparation thereof.

"Conjugating" refers to the formation of a covalent bond.

"Bile acid transport system" refers to any membrane transporter protein capable of causing a bile acid or a derivative thereof to be translocated across a membrane of a cell of the gastrointestinal tract or liver.

"Active transport or active transport mechanism" refers to the movement of molecules across cellular membranes that:

a) is directly or indirectly dependent on an energy mediated process (i.e. driven by ATP hydrolysis, ion gradient, etc); or b) occurs by facilitated diffusion mediated by interaction with specific transporter proteins; or c) occurs through a modulated solute channel.

"A moiety selected to permit a compound of formula (I), (II) or (III) to be translocated across the intestinal wall of an animal via the bile acid transport system" refers to compounds which, when conjugated to the drug/cleavable linker moiety, are translocated across the intestinal wall via the bile acid transport system. Evaluation of which candidate compounds can be so translocated across the intestinal wall can be conducted by the in vitro assay set forth in Example 42 below.

"Practical dosage regimen" refers to a schedule of drug administration that is practical for a patient to comply with. For human patients, a practical dosage regimen for an orally administered drug is likely to be an aggregate dose of less than 10 g/day.

"Acidic heterocycle" refers to a reprotonatable heterocycle having a pKa less than 7.0. Examples of such heterocycles include the following:

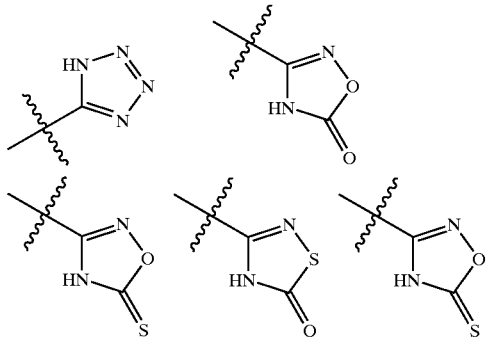

"Cleavable linker" refers to linkers that contain one or more functional groups which permit cleavage of such groups in vivo by, for example, endogenous enzymes. Preferably, the functional group subject to cleavage in the cleavable linker is attached adjacent the drug moiety, D, such that upon cleavage, the free drug is released. The cleavable linker preferably comprises one or more functional groups such as ester groups, amide groups, glycolamide ester groups, amidomethyl esters, acyloxyalkyl esters, alkoxycarbonyloxyalkyl esters, and the like. With the proviso that the cleavable linker is not an oligo peptide of one to three amino acids in length.

The term "drug/cleavable linker/transporter compound" (which sometimes is referred to as the "drug-transporter compound", "drug/linker/transporter compound" and "drug/cleavable linker/transporter conjugate" refers to compounds of formulae (I), (II) and/or (III).

"Linear oligopeptide" refers to an amide oligomer comprising either a terminal amino group or a terminal carboxylic acid group or (preferably) both a terminal amino group and a terminal carboxylic acid group, which oligomer is formed by condensation of the terminal amino residue of at least one amino acid (or GABA analog) with the terminal carboxylic acid residue of at least a second amino acid (or GABA analog). In addition to the GABA analog, the amino acids comprising the oligopeptide are optionally either α-amino acids, β-amino acids, or a mixture of α-amino acids and β-amino acids. Note that when an α-amino acid additionally contains either a β-amino group or a β-carboxylic acid group (e.g. as in aspartic acid) a linear oligopeptide formed from such an amino acid is intended to imply that it is the α-amine or α-carboxylic acid moiety (or both) of such residue that is involved in amide formation.

"α-Amino acids" are molecules of the formula:

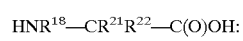

wherein:

R$^{18}$ is hydrogen or R$^{18}$ and R$^{21}$ together with the atoms to which they are attached form a heterocyclyl ring;

R$^{21}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{21}$ and R$^{22}$ together with the atoms to which they are attached form a cycloalkyl, substituted cycloalkyl, heterocyclyl or substituted heterocyclyl ring.

"β-Amino acids" are molecules of formula

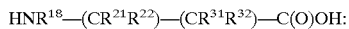
HNR$^{18}$—(CR$^{21}$R$^{22}$)—(CR$^{31}$R$^{32}$)—C(O)OH:

wherein:

R$^{18}$ is hydrogen or R$^{18}$ and R$^{21}$ together with the atoms to which they are attached form a heterocyclyl ring;

R$^{21}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{21}$ and R$^{22}$ together with the atoms to which they are attached form a cycloalkyl, substituted cycloalkyl, heterocyclyl or substituted heterocyclyl ring, or R$^{21}$ and R$^{31}$ together with the atoms to which they are attached form a cycloalkyl, substituted cycloalkyl, heterocyclyl or substituted heterocyclyl ring;

R$^{22}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R$^{31}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{31}$ and R$^{32}$ together with the atoms to which they are attached form a cycloalkyl, substituted cycloalkyl, heterocyclyl or substituted heterocyclyl ring;

R$^{32}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl.

"Derived from a compound" refers to a moiety that is structurally related to such a compound. The structure of the moiety is identical to the compound except at 1 or 2 positions. At these positions either a hydrogen atom attached to a heteroatom, or a hydroxyl moiety of a carboxylic, phosphonic, phosphoric or sulfonic acid group has been replaced with a covalent bond that serves as a point of attachment to another moiety.

"Amino-protecting group" or "amino-blocking group" refers to any group which when bound to one or more amino groups prevents reactions from occurring at these amino groups and which protecting groups can be removed by conventional chemical steps to reestablish the amino group. The particular removable blocking group is not critical and preferred amino blocking groups include, by way of example only, t-butyoxycarbonyl (t-BOC), benzyloxycarbonyl (CBZ), and the like.

"Carboxyl-protecting group" or "carboxyl-blocking group" refers to any group which when bound to one or more carboxyl groups prevents reactions from occurring at these groups and which protecting groups can be removed by conventional chemical steps to reestablish the carboxyl group. The particular removable blocking group is not critical and preferred carboxyl blocking groups include, by way of example only, esters of the formula —COOR" where R" is selected from the group consisting of alkyl, substituted alkyl, alkenyl, substituted alkenyl, aryl, substituted aryl, alkaryl, substituted alkaryl, cycloalkyl, substituted cycloalkyl, heteroaryl, substituted heteroaryl, heterocyclic, and substituted heterocyclic.

"Alkyl" refers to alkyl groups preferably having from 1 to 20 carbon atoms and more preferably 1 to 6 carbon atoms. This term is exemplified by groups such as methyl, t-butyl, n-heptyl, octyl, dodecyl and the like.

"Substituted alkyl" refers to an alkyl group, preferably of from 1 to 20 carbon atoms, having from 1 to 5 substituents selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxylaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted aryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)— cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiocarbonylamino" refers to the group —C(S)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form, together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 20 carbon atoms and more preferably 2 to 6 carbon atoms and having at least 1 and preferably from 1–2 sites of alkenyl unsaturation.

"Substituted alkenyl" refers to alkenyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(Q)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkenyloxy" refers to the group —O-alkenyl.

"Substituted alkenyloxy" refers to the group —O-substituted alkenyloxy.

"Alkynyl" refers to alkynyl group preferably having from 2 to 20 carbon atoms and more preferably 3 to 6 carbon atoms and having at least 1 and preferably from 1–2 sites of alkynyl unsaturation.

"Substituted alkynyl" refers to alkynyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkylene" refers to a divalent alkylene group preferably having from 1 to 20 carbon atoms and more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" refers to alkylene groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkenylene" refers to a divalent alkenylene group preferably having from 2 to 20 carbon atoms and more preferably 1 to 6 carbon atoms and having from 1 to 2 sites of alkenyl unsaturation. This term is exemplified by groups such as ethenylene (—CH═CH—), propenylene (—CH$_2$CH═CH—), and the like.

"Substituted alkenylene" refers to alkenylene groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkynylene" refers to a divalent alkynylene group preferably having from 2 to 20 carbon atoms and more preferably 1 to 6 carbon atoms and having from 1 to 2 sites of alkynyl unsaturation. This term is exemplified by groups such as ethynylene, propynylene and the like.

"Substituted alkynylene" refers to alkynylene groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Amidino" refers to the group H$_2$NC(=NH)— and the term "alkylamidino" refers to compounds having 1 to 3 alkyl groups (e.g., alkylHNC(=NH)—).

"Thioamidino" refers to the group RSC(=NH)— where R is hydrogen or alkyl.

"Aminoacyl" refers to the groups —NRC(O)alkyl, —NRC(O)substituted alkyl, —NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O) substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the groups —NRC(O)O-alkyl, —NRC(O)O-substituted alkyl, —NRC(O)O-alkenyl, —NRC(O)O-substituted alkenyl, —NRC(O)O-alkynyl, —NRC(O)O-substituted alkynyl, —NRC(O)O-cycloalkyl, —NRC(O)O-substituted cycloalkyl, —NRC(O)O-aryl, —NRC(O)O-substituted aryl, —NRC(O)O-heteroaryl, —NRC(O)O-substituted heteroaryl, —NRC(O)O-heterocyclic, and —NRC(O)O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxycarbonylamino" refers to the groups —OC(O)NH$_2$, —OC(O)NRR, —OC(O)NR-alkyl, —OC(O)NR-substituted alkyl, —OC(O)NR-alkenyl, —OC(O)NR-substituted alkenyl, —OC(O)NR-alkynyl, —OC(O)NR-substituted alkynyl, —OC(O)NR-cycloalkyl, —OC(O)NR-substituted cycloalkyl, —OC(O)NR-aryl, —OC(O)NR-substituted aryl, —OC(O)NR-heteroaryl, —OC(O)NR-substituted heteroaryl, —OC(O)NR-heterocyclic, and —OC(O)NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)NH$_2$, —OC(S)NRR, —OC(S)NR-alkyl, —OC(S)NR-substituted alkyl, —OC(S)NR-alkenyl, —OC(S)NR-substituted alkenyl, —OC(S)NR-alkynyl, —OC(S)NR-substituted alkynyl, —OC(S)NR-cycloalkyl, —OC(S)NR-substituted cycloalkyl, —OC(S)NR-aryl, —OC(S)NR-substituted aryl, —OC(S)NR-heteroaryl, —OC(S)NR-substituted heteroaryl, —OC(S)NR-heterocyclic, and —OC(S)NR-substituted heterocyclic where R is hydrogen, alkyl or where each R is joined to form together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the groups —NRC(O)NRR, —NRC(O)NR-alkyl, —NRC(O)NR-substituted alkyl, —NRC(O)NR-alkenyl, —NRC(O)NR-substituted alkenyl, —NRC(O)NR-alkynyl, —NRC(O)NR-substituted alkynyl, —NRC(O)NR-aryl, —NRC(O)NR-substituted aryl, —NRC(O)NR-cycloalkyl, —NRC(O)NR-substituted cycloalkyl, —NRC(O)NR-heteroaryl, and —NRC(O)NR-substituted heteroaryl, —NRC(O)NR-heterocyclic, and —NRC(O)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the groups —NRC(S)NRR, —NRC(S)NR-alkyl, —NRC(S)NR-substituted alkyl, —NRC(S)NR-alkenyl, —NRC(S)NR-substituted alkenyl, —NRC(S)NR-alkynyl, —NRC(S)NR-substituted alkynyl, —NRC(S)NR-aryl, —NRC(S)NR-substituted aryl, —NRC(S)NR-cycloalkyl, —NRC(S)NR-substituted cycloalkyl, —NRC(S)NR-heteroaryl, and —NRC(S)NR-substituted heteroaryl, —NRC(S)NR-heterocyclic, and —NRC(S)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to a monovalent unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7yl, and the like). Preferred aryls include phenyl and naphthyl.

"Substituted aryl" refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Arylene" refers to a divalent unsaturated aromatic carbocyclic group of from 6 to 14 carbon atoms having a single ring (e.g., phenylene) or multiple condensed rings (e.g., naphthylene or anthrylene) which condensed rings may or may not be aromatic. Preferred arylenes include phenylene and naphthylene.

"Substituted arylene" refers to arylene groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Aryloxy" refers to the group aryl-O— which includes, by way of example, phenoxy, naphthoxy, and the like.

"Substituted aryloxy" refers to substituted aryl-O— groups.

"Aryloxyaryl" refers to the group -aryl-O-aryl.

"Substituted aryloxyaryl" refers to aryloxyaryl groups substituted with from 1 to 3 substituents on either or both aryl rings selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxyamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Cycloalkyl" refers to cyclic alkyl groups of from 3 to 10 carbon atoms having a single cyclic ring including, by way of example, cyclopropyl, cyclobutyl, cyclopentyl, cyclooctyl and the like. This definition includes bridged groups such as bicyclo[2.2.1]heptane and bicyclo[3.3.1]nonane.

"Cycloalkyloxy" refers to —O-cycloalkyl.

"Cycloalkenyl" refers to cyclic alkenyl groups of from 3 to 8 carbon atoms having a single cyclic ring.

"Cycloalkenyloxy" refers to —O-cycloalkenyl.

"Substituted cycloalkyl" and "substituted cycloalkenyl" refers to an cycloalkyl or cycloalkenyl group, preferably of from 3 to 10 carbon atoms, having from 1 to 5 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Substituted cycloalkyloxy" and "substituted cycloalkenyloxy" refers to —O-substituted cycloalkyl and —O-substituted cycloalkenyloxy respectively.

"Cycloalkylene" refers to divalent cyclic alkylene groups of from 3 to 8 carbon atoms having a single cyclic ring including, by way of example, cyclopropylene, cyclobutylene, cyclopentylene, cyclooctylene and the like.

"Cycloalkenylene" refers to a divalent cyclic alkenylene groups of from 3 to 8 carbon atoms having a single cyclic ring.

"Substituted cycloalkylene" and "substituted cycloalkenylene" refers to a cycloalkylene or cycloalkenylene group, preferably of from 3 to 8 carbon atoms, having from 1 to 5 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Cycloalkoxy" refers to —O-cycloalkyl groups.

"Substituted cycloalkoxy" refers to —O-substituted cycloalkyl groups.

"Guanidino" refers to the groups —NRC(=NR)NRR, —NRC(=NR)NR-alkyl, —NRC(=NR)NR-substituted alkyl, —NRC(=NR)NR-alkenyl, —NRC(=NR)NR-substituted alkenyl, —NRC(=NR)NR-alkynyl, —NRC(=NR)NR-substituted alkynyl, —NRC(=NR)NR-aryl, —NRC(=NR)NR-substituted aryl, —NRC(=NR)NR-cycloalkyl, —NRC(=NR)NR-heteroaryl, —NRC(=NR)NR-substituted heteroaryl, —NRC(=NR)NR-heterocyclic, and —NRC(=NR)NR-substituted heterocyclic where each R is independently hydrogen and alkyl as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"N,N-Dimethylcarbamyloxy" refers to the group —OC(O)N(CH$_3$)$_2$.

"Guanidinosulfone" refers to the groups —NRC(=NR)NRSO$_2$-alkyl, —NRC(=NR)NRSO$_2$-substituted alkyl, —NRC(=NR)NRSO$_2$-alkenyl, —NRC(=NR)NRSO$_2$-substituted alkenyl, —NRC(=NR)NRSO$_2$-alkynyl, —NRC(=NR)NRSO$_2$-substituted alkynyl, —NRC(=NR)NRSO$_2$-aryl, —NRC(=NR)NRSO$_2$-substituted aryl, —NRC(=NR)NRSO$_2$-cycloalkyl, —NRC(=NR)NRSO$_2$-substituted cycloalkyl, —NRC(=NR)NRSO$_2$-heteroaryl, and —NRC(=NR)NRSO$_2$-substituted heteroaryl, —NRC(=NR)NRSO$_2$-heterocyclic, and —NRC(=NR)NRSO$_2$-substituted heterocyclic where each R is independently hydrogen and alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Halo" or "halogen" refers to fluoro, chloro, bromo and iodo and preferably is either chloro or bromo.

"Heteroaryl" refers to an aromatic carbocyclic group of from 2 to 10 carbon atoms and 1 to 4 heteroatoms selected from the group consisting of oxygen, nitrogen and sulfur within the ring. Such heteroaryl groups can have a single ring (e.g., pyridyl or furyl) or multiple condensed rings (e.g., indolizinyl or benzothienyl). Preferred heteroaryls include pyridyl, pyrrolyl, indolyl and furyl.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Heteroarylene" refers to a divalent aromatic carbocyclic group of from 2 to 10 carbon atoms and 1 to 4 heteroatoms selected from the group consisting of oxygen, nitrogen and sulfur within the ring. Such heteroarylene groups can have a single ring (e.g., pyridylene or furylene) or multiple condensed rings (e.g., indolizinylene or benzothienylene). Preferred heteroarylenes include pyridylene, pyrrolylene, indolylene and furylene.

"Substituted heteroarylene" refers to heteroarylene groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Heteroaryloxy" refers to the group —O-heteroaryl and "substituted heteroaryloxy" refers to the group —O-substituted heteroaryl. "Heterocycle" or "heterocyclic" refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl.

"Substituted heterocyclic" refers to heterocycle groups which are substituted with from 1 to 3 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, —C(O)O-aryl, —C(O)O-substituted aryl, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclene" refers to a divalent saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl.

"Substituted heterocyclene" refers to heterocyclene groups which are substituted with from 1 to 3 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, —C(O)O-aryl, —C(O)O-substituted aryl, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Heterocyclyloxy" refers to the group —O-heterocyclic and "substituted heterocyclyloxy" refers to the group —O-substituted heterocyclic.

"Thiol" refers to the group —SH.

"Thioalkyl" refers to the groups —S-alkyl.

"Substituted thioalkyl" refers to the group —S-substituted alkyl.

"Thiocycloalkyl" refers to the groups —S-cycloalkyl.

"Substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

"Amino" refers to the —$NH_2$ group.

"Substituted amino" refers to the —NR'R" group wherein R' and R" are independently hydrogen, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocyclic, substituted heterocyclic or where R' and R", together with the nitrogen atom pendent thereto, form a heterocyclic ring.

"Pharmaceutically acceptable salt" refers to pharmaceutically acceptable salts of a compound of Formulae (I), (II) or (III) which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Utility

The compounds and methods described herein permit the drug/cleavable linker/transporter compounds to provide sustained release of the GABA analog or active metabolite thereof relative to oral dosing with the parent drug itself In this regard, enterohepatic recycling of the bile acid conjugates creates a reservoir for the active agent.

GABA analogs are useful in treating epilepsy, faintness attacks, hypokinesia, cranial disorders, neurodegenerative disorders, depression, anxiety, panic, pain, neuropatholgical disorders, gastrointestinal damage, inflammation and irritable bowel disease. See, for example, WO 99/31075 which is incorporated herein by reference in its entirety.

Compounds of this invention which employ a non-cleavable linker can be used for diagnostic purposes to evaluate the relative transport of such compounds across the intestinal wall thereby providing clinical information regarding transport efficacy and the like.

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Mo., USA) or are prepared by methods known to those skilled in the art following procedures set forth in references such as Fieser and Fieser's Reagents for Organic Synthesis, Volumes 1–15 (John Wiley and Sons, 1991); Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 4th Edition), and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Preparation of Compounds of Formula (I)

Schemes A–C describe alternative methods to prepare the compounds of Formula (I). where X, $R^1$ and $R^2$ are hydroxy, Z is a group of formula —M—$Q^b$—D' where M is —$CH_2CH_2$—C(O)—, $Q^b$ is a cleavable bond, and D' is a GABA analog moiety related to formula (a) that is attached to M through its terminal amino group can be prepared as illustrated and described in Scheme A below.

Scheme A

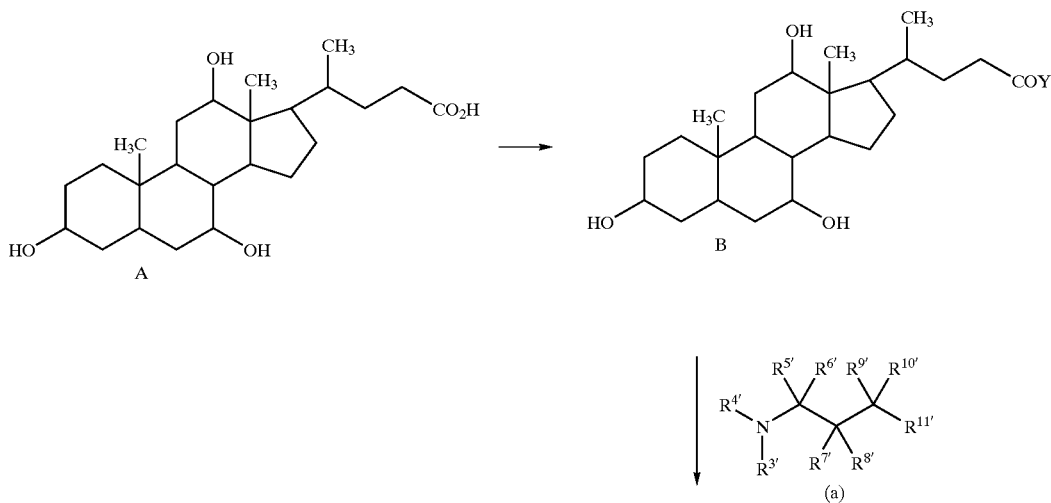

(a)

-continued

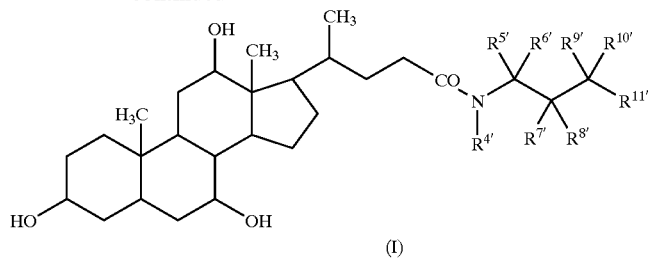

(I)

A compound of Formula (I) where $X^1$, $R^1$ and $R^2$ are hydroxy, Z is a group of formula —M—$Q^b$—D' where M is —$CH_2CH_2$—C(O)—, $Q^b$ is a cleavable bond, and D' is a GABA analog moiety related to formula (a) that is attached to M through its terminal amino group can be prepared by first converting commercially available cholic acid A to an activated acid derivative B where Y is a suitable leaving group, followed by treatment with an amine of formula (a) (where $R^{3'}$ is hydrogen) to provide a compound of Formula (I). Compound B where Y is a leaving group such as —$OCO_2Et$ can be prepared by treating A with ethyl chloroformate in the presence of a tertiary organic amine such as triethylamine, tributylamine, diisopropylethylamine and the like. The reaction is typically carried out in a suitable organic solvent such as tetrahydrofuran and at low temperatures e.g., between –15 to 0° C. It will be recognized by a person skilled in the art that compound A can also be converted to an activated acid B in the presence of other acid activating agents such as dicyclohexylcarbodiimide, and the like. The displacement of leaving group Y with an amine of formula (a) is carried out by adding (a) to the activated acid B, in the presence of an aqueous inorganic base such as sodium hydroxide, sodium bicarbonate, potassium hydroxide and the like.

Amines of formula (a) are either commercially available or they can be prepared by methods well known in the art of organic chemistry. For example, 1-aminomethyl-1-cyclohexane acetic acid is commercially available. 2-Aminomethyl-4-methylpentanoic acid can be prepared by the methods described in U.S. Pat. No. 5,563,175.

Compounds of Formula (II) where $R^1$, and $R^2$ are hydroxy, A is —O—, $Q^b$ is a cleavable bond, and D' is a GABA analog moiety related to formula (a) can be prepared as illustrated and described in Scheme B below.

Scheme B

A compound of Formula (II) where $R^1$ and $R^2$ are hydroxy, A is —O—, $Q^b$ is a cleavable bond, and D" is a GABA analog moiety related to formula (a) can be prepared by converting 23-nor-5β2-cholanic acid D (prepared according to the method described in U.S. Pat. No. 5,541,348) to a corresponding hydroxy derivative of formula E. Treatment of E with an isocyanate of formula F then provides a compound of Formula (I). Typically, $R^{11'}$ is —COOR (i.e., an ester) where the R group is a suitable protecting group.

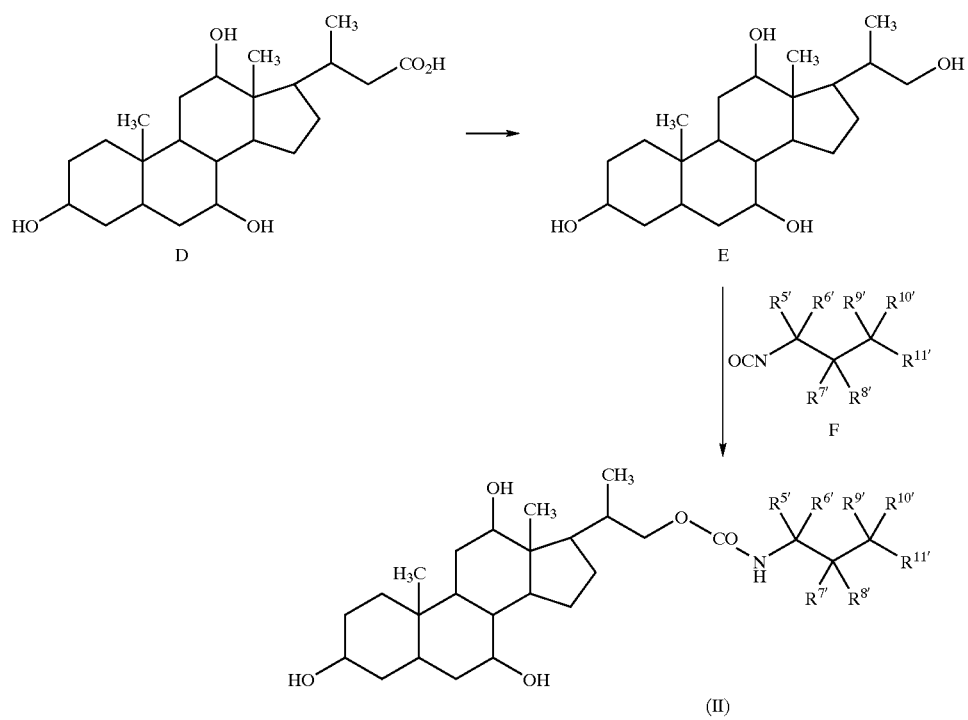

Compounds E and F can be prepared from D as described in detail in Example 10 below.

Where $R^{11'}$ is an ester containing a protecting group, the reaction conditions for removal of the protecting group will depend on the type of the protecting group. For example, if the group is a 2-cyanoethyloxy group, it is removed by treatment with piperidine or DBU in a halogenated organic solvent such as methylene chloride, followed by treatment with an acid such as acetic acid to provide a compound of formula (I) where $R^{11'}$ is carboxylic acid.

Compounds of Formula (I) where $R^1$ and $R^2$ are hydroxy, Z is a group of formula —M—$Q^b$—D' where M is —$CH_2CH_2$—C(O)—, $Q^b$ is a linking group, and D' is a GABA analog moiety related to formula (a) that is attached to $Q^b$ through its terminal amino group can be prepared by methods well known in the art. Some such methods are illustrated and described below.

A compound of formula (I) wherein $Q^b$ is a linking group of formula —O(CH($R^a$))$_n$CO— where n=1–6 and $R^a$ is selected from the group consisting of hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl and substituted heteroaryl can be prepared as shown below.

formula (a) then provides a compound of Formula (I). The coupling reactions are carried out under conditions well known in the art. A detailed description of the synthesis of compounds of formula (I) utilizing the procedure described above is given in Working Examples 38–40 below. Hydroxy acids of formula G include the a-hydroxy acids glycolic acid and lactic acid, the β-hydroxy acid 3-hydroxyisobutyric acid, and are commercially available in free and/or protected forms. Others can be prepared by methods well known in the art. It will be appreciated by a person skilled in the art that amino acids such as serine, glutamic acid, aspartic acid can be used to 2prepare compounds of formula (I) wherein the linking group carries an acid moiety. Examples of such linking groups are —NH—CH($CO_2R^b$)—($CH_2$)$_2$CO—, —NH—CH($CH_2OSO_3R^b$)—CO—, and the like wherein $R^b$ is hydrogen or alkyl or an alkali cation. Detailed description of synthesis of compounds of formula (I) utilizing these linking groups is provided in Examples 5 and 7.

Compounds of Formula (I) where $R^1$ and $R^2$ are hydroxy, X is a group of formula D—$Q^a$—(T)— where T is —O—, $Q^a$ is a cleavable bond, and D is a GABA analog moiety related to formula (a) that is attached to T through its carboxyl terminus can be prepared as illustrated and described in Scheme C below.

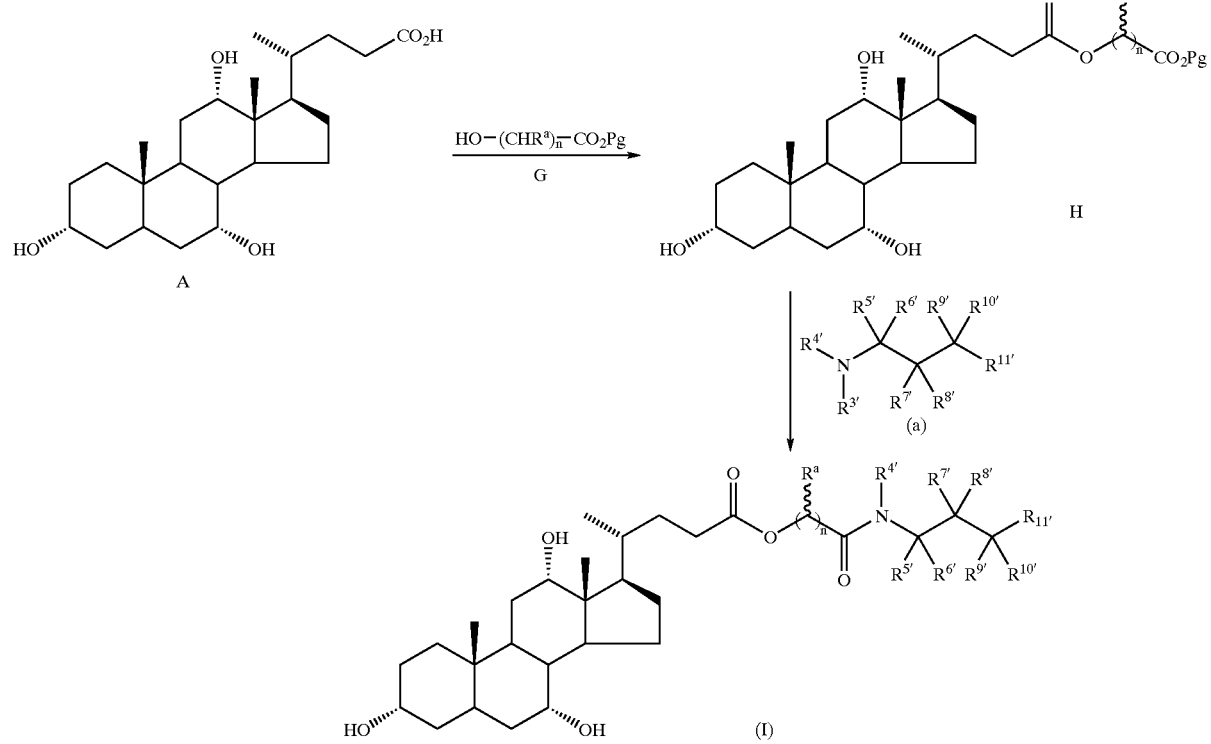

A compound of formula (I) wherein $Q^b$ is a linking group of formula —O(CH($R^a$))$_n$CO— where n=1–6 and $R^a$ is selected from the group consisting of hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl and substituted heteroaryl can be prepared by first reacting a protected hydroxy acid of formula G (where Pg is a protecting group) with compound A to provide a compound of formula H, which upon coupling with an amine of

Scheme C

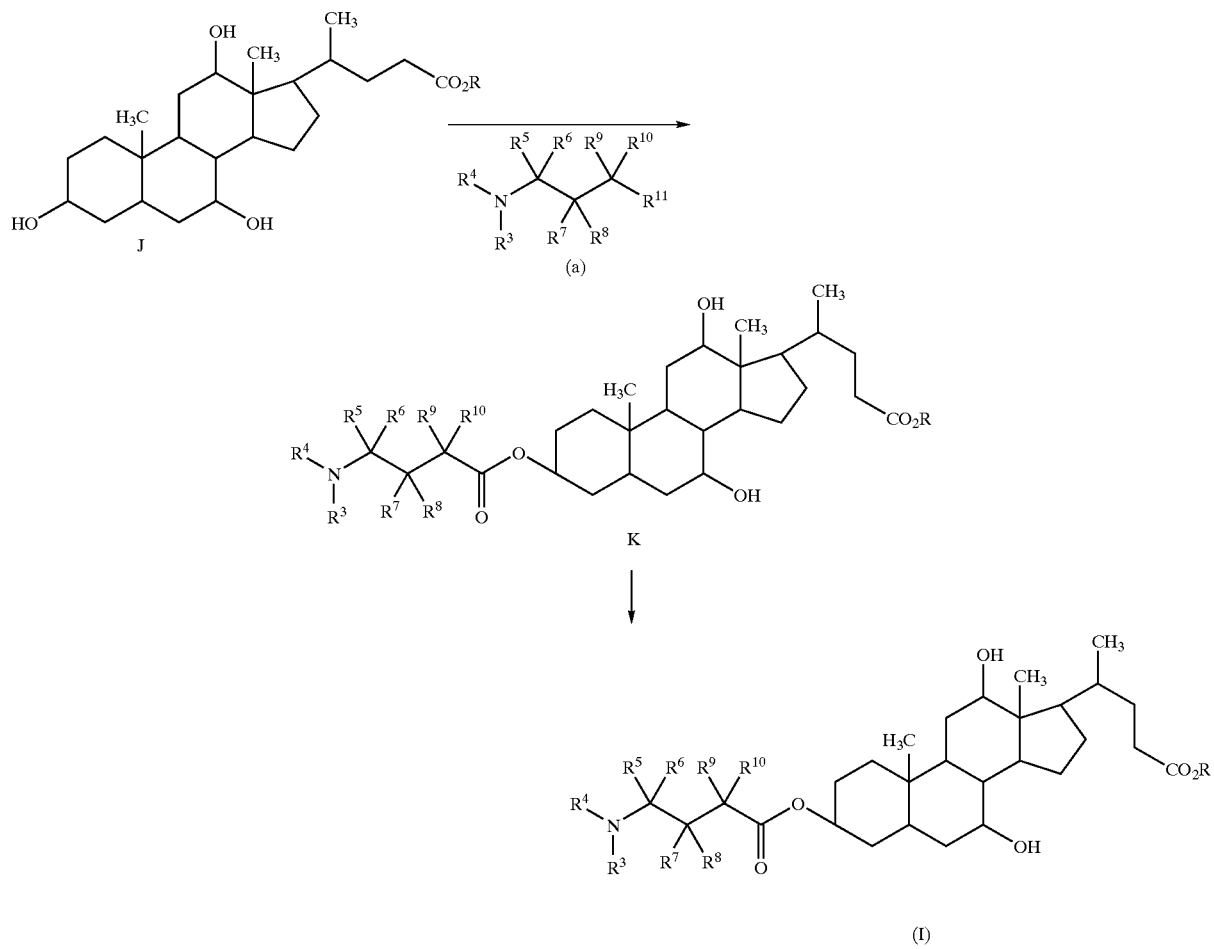

Figure 24:
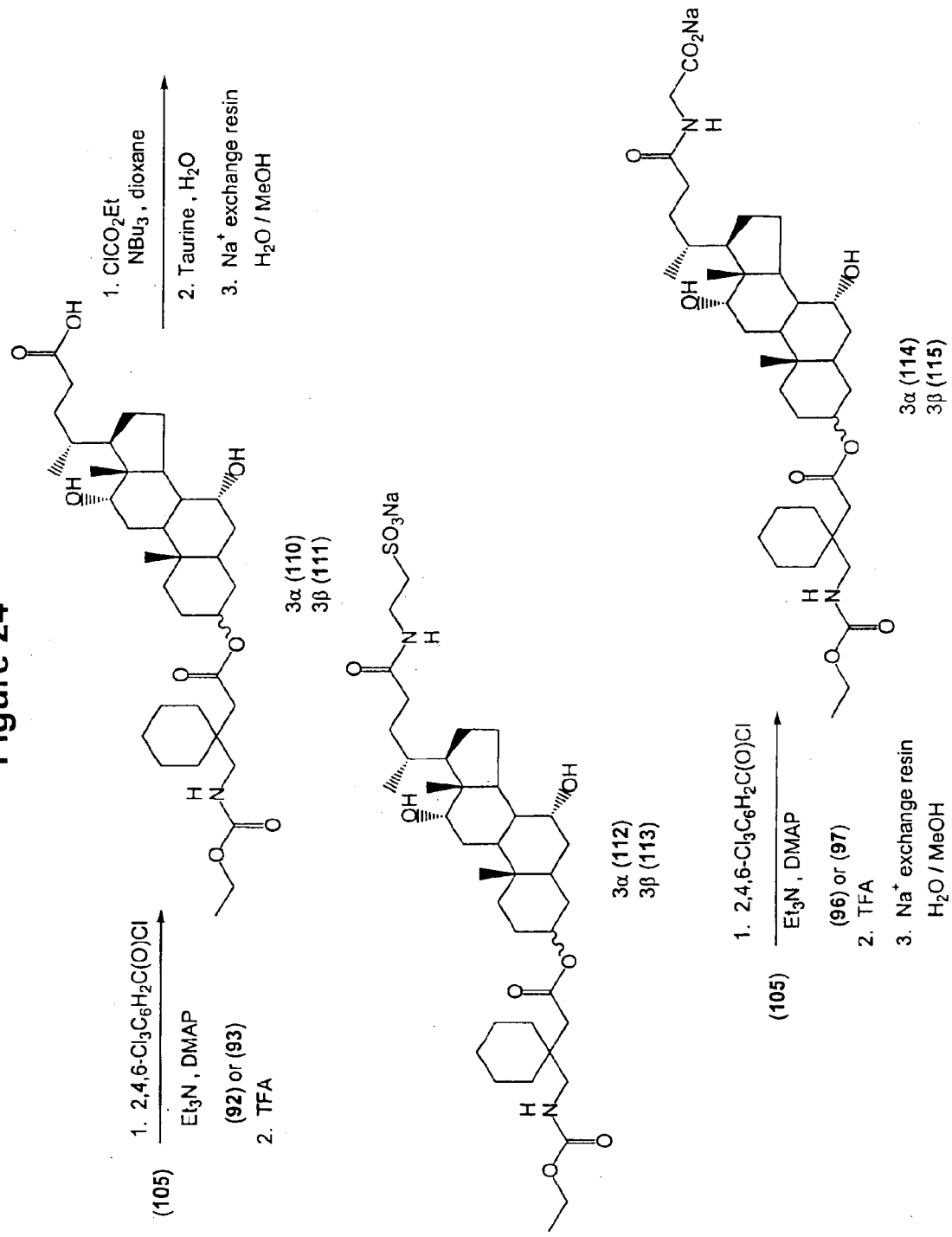
Figure 25:
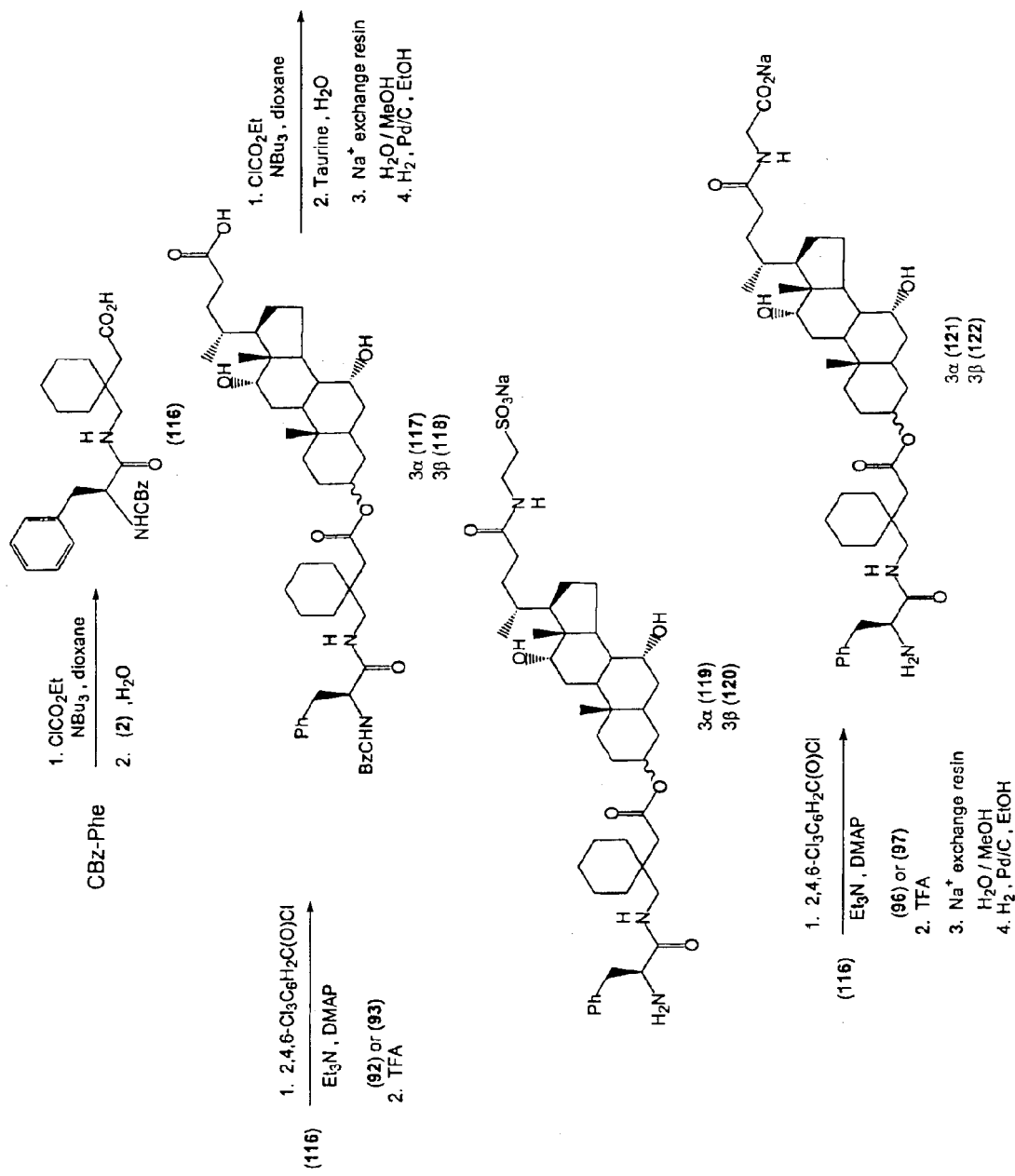
Figure 26:
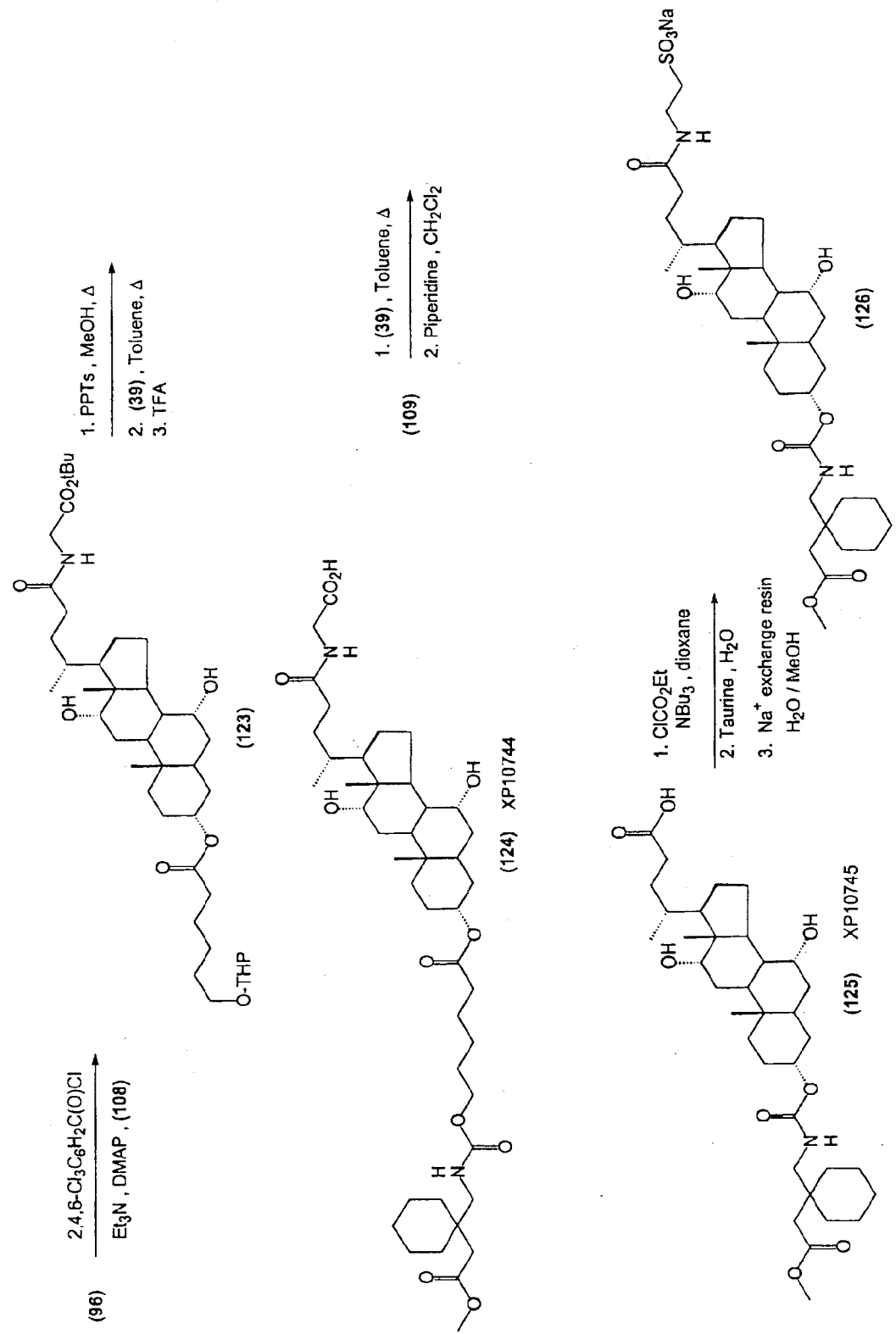
Figure 27:
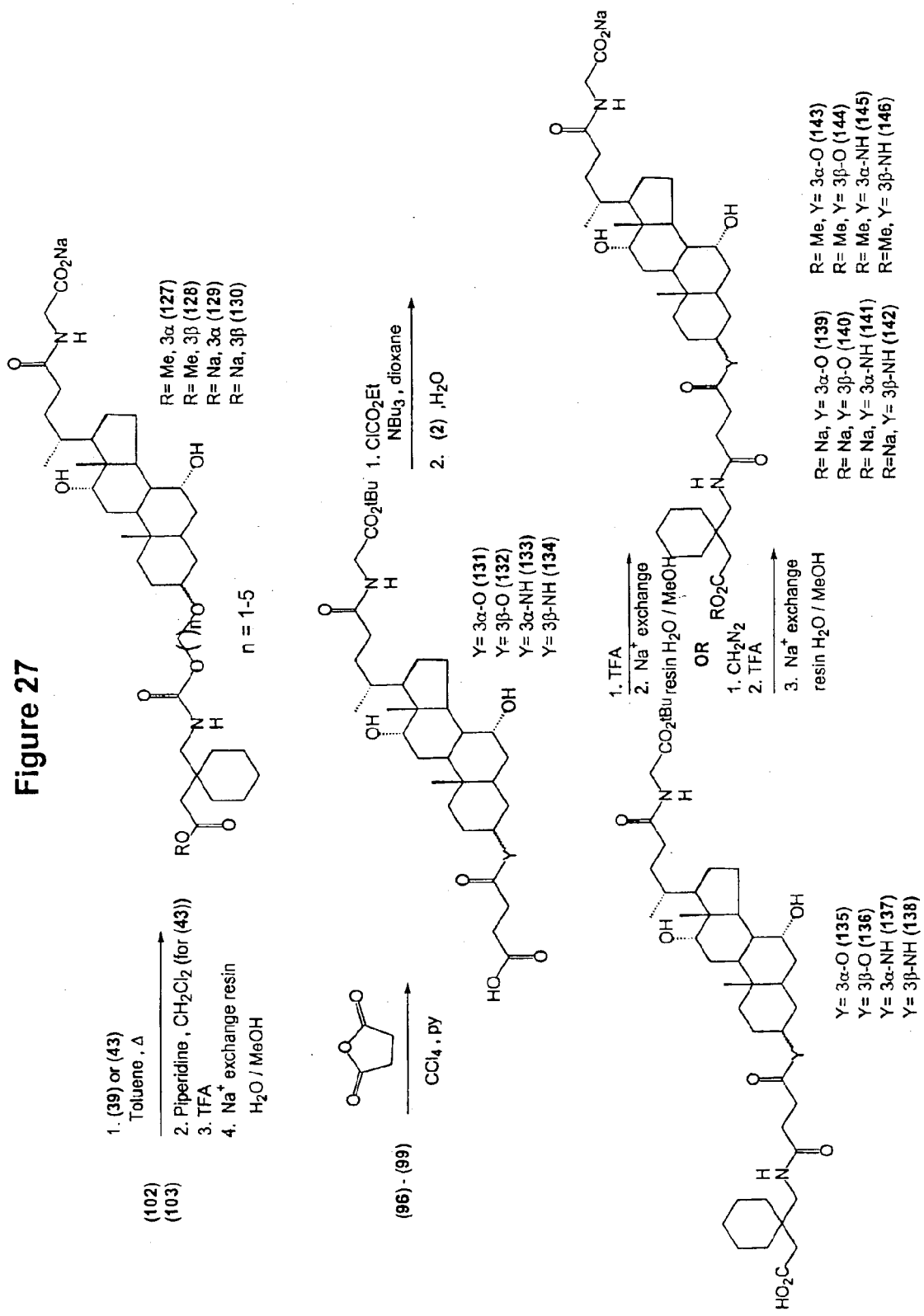
Figure 28:
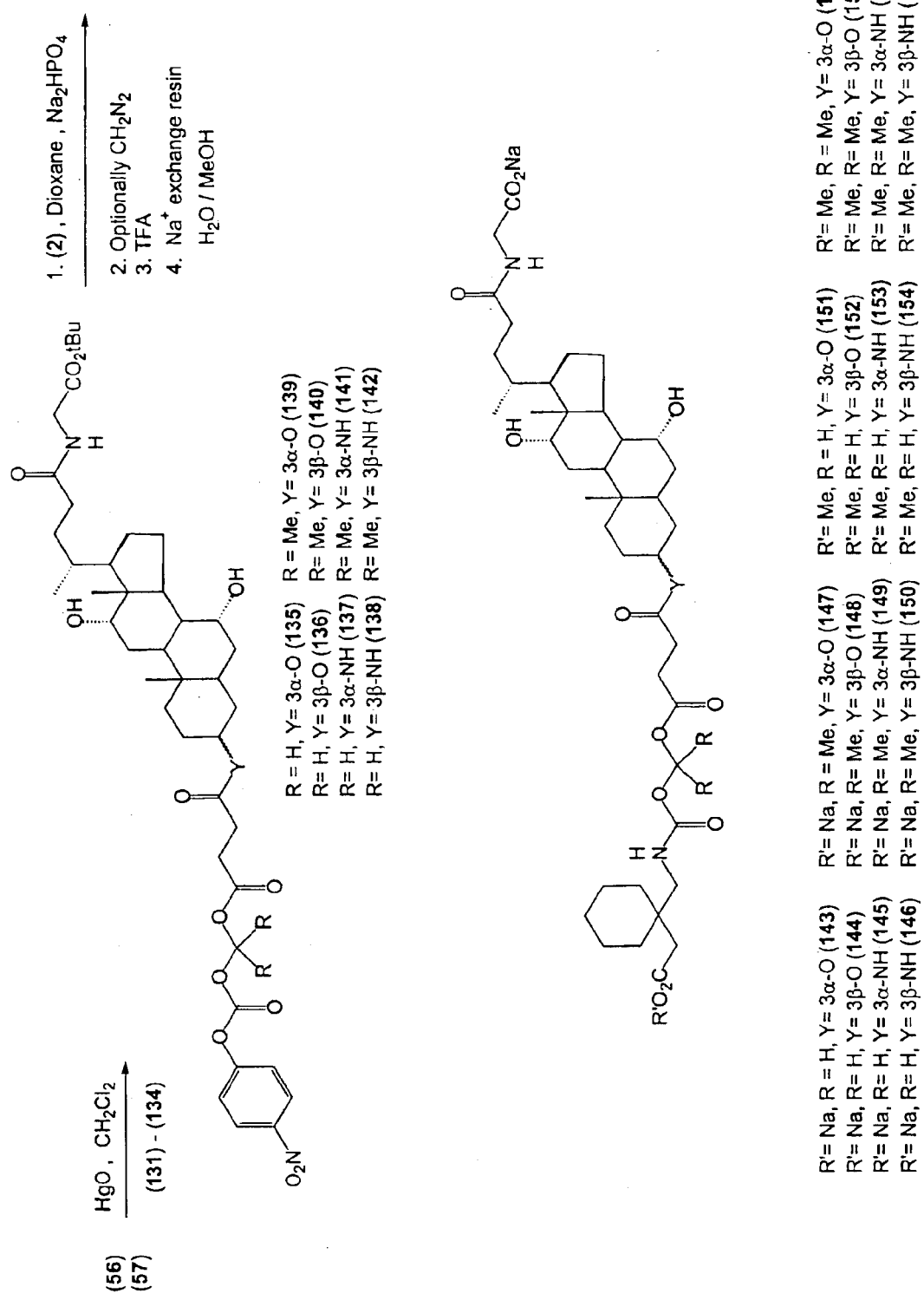
Figure 29:
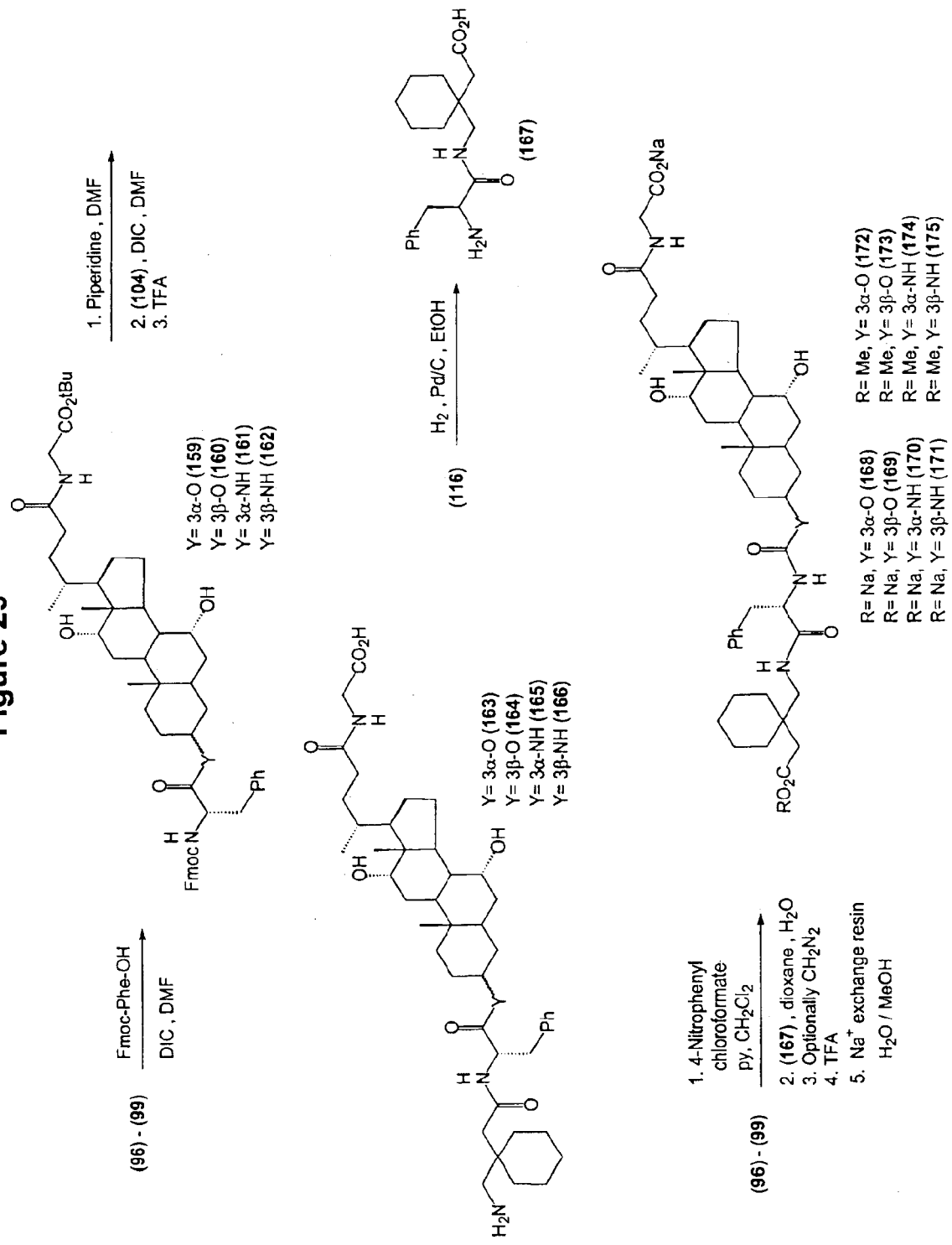
Figure 30:
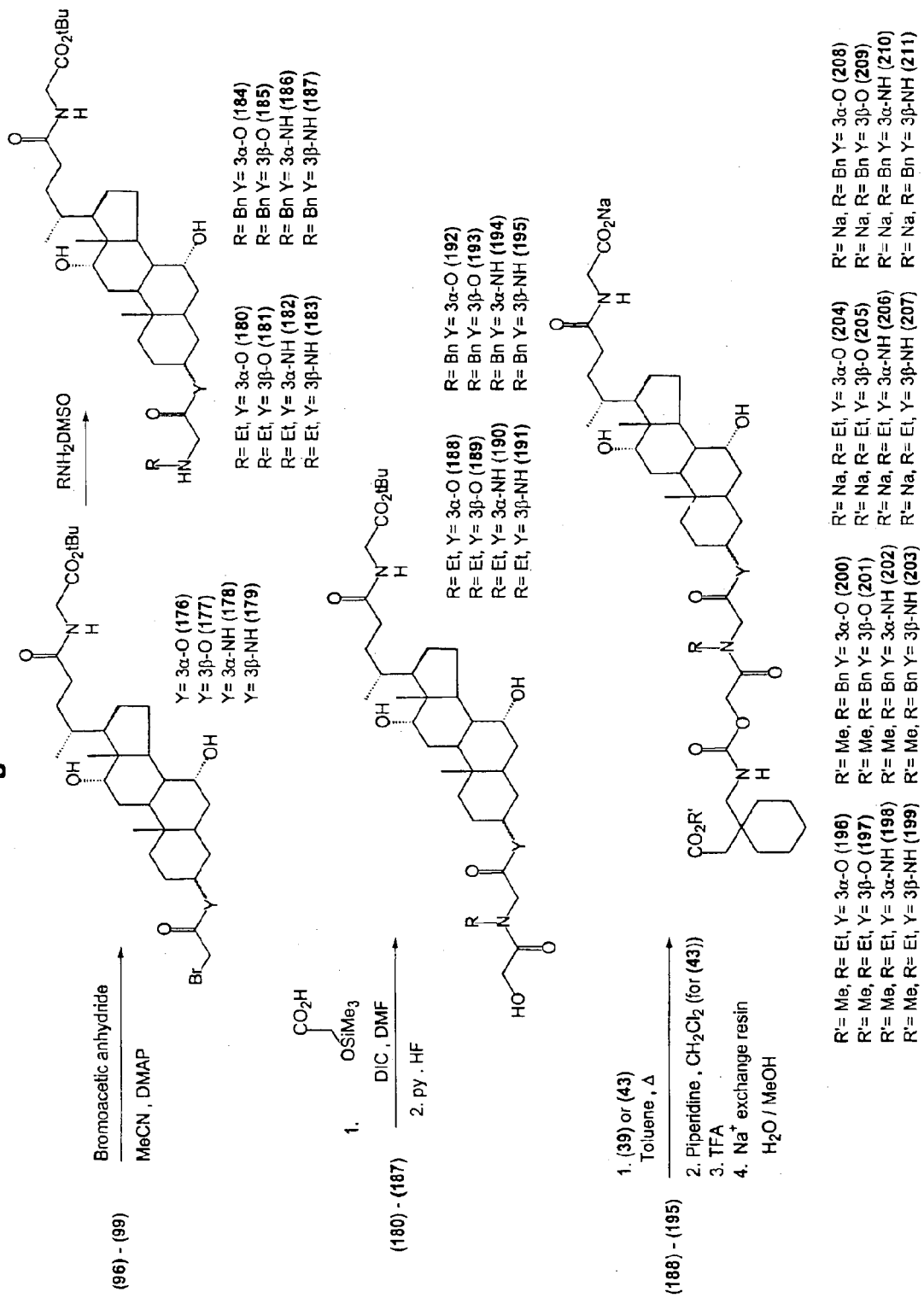
Figure 31:
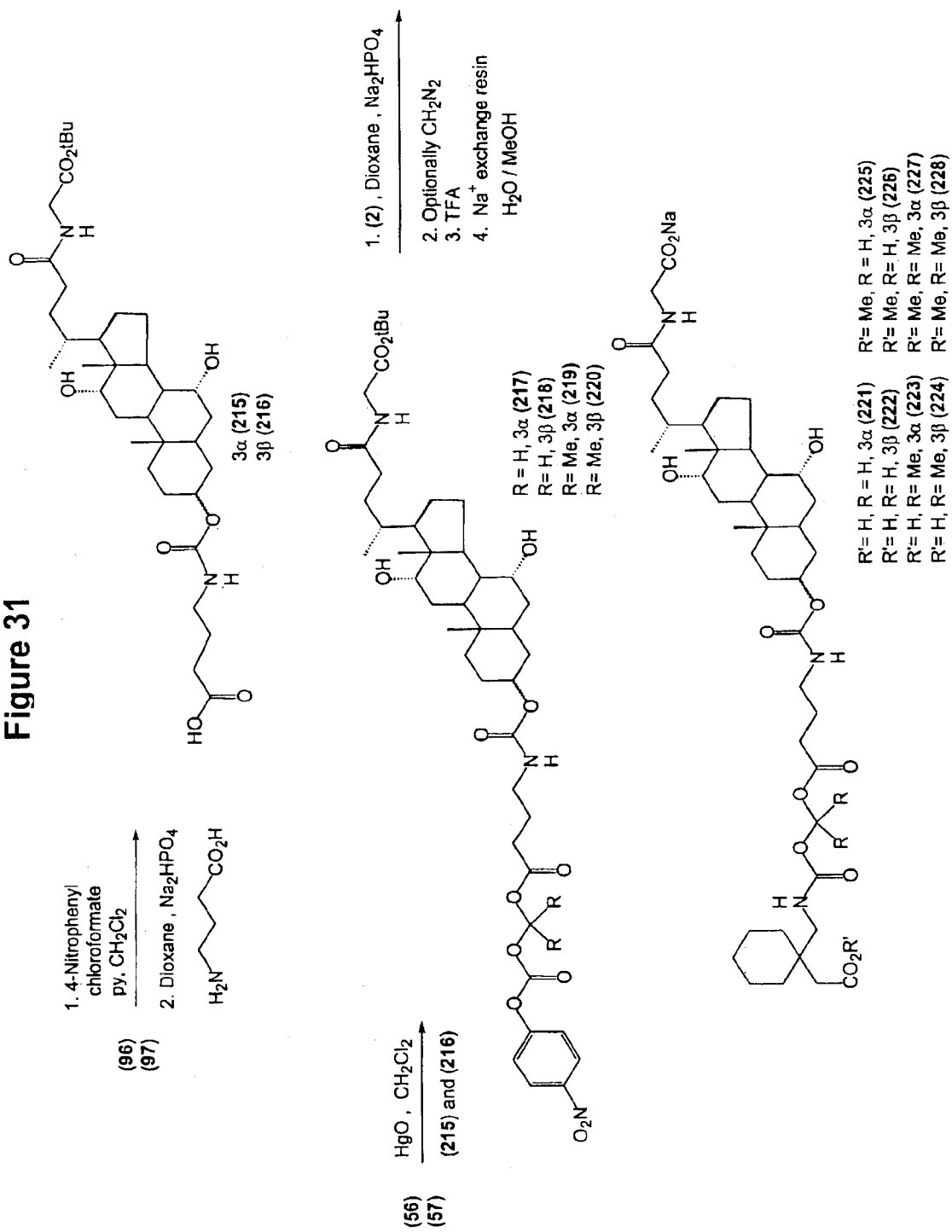
Figure 32:
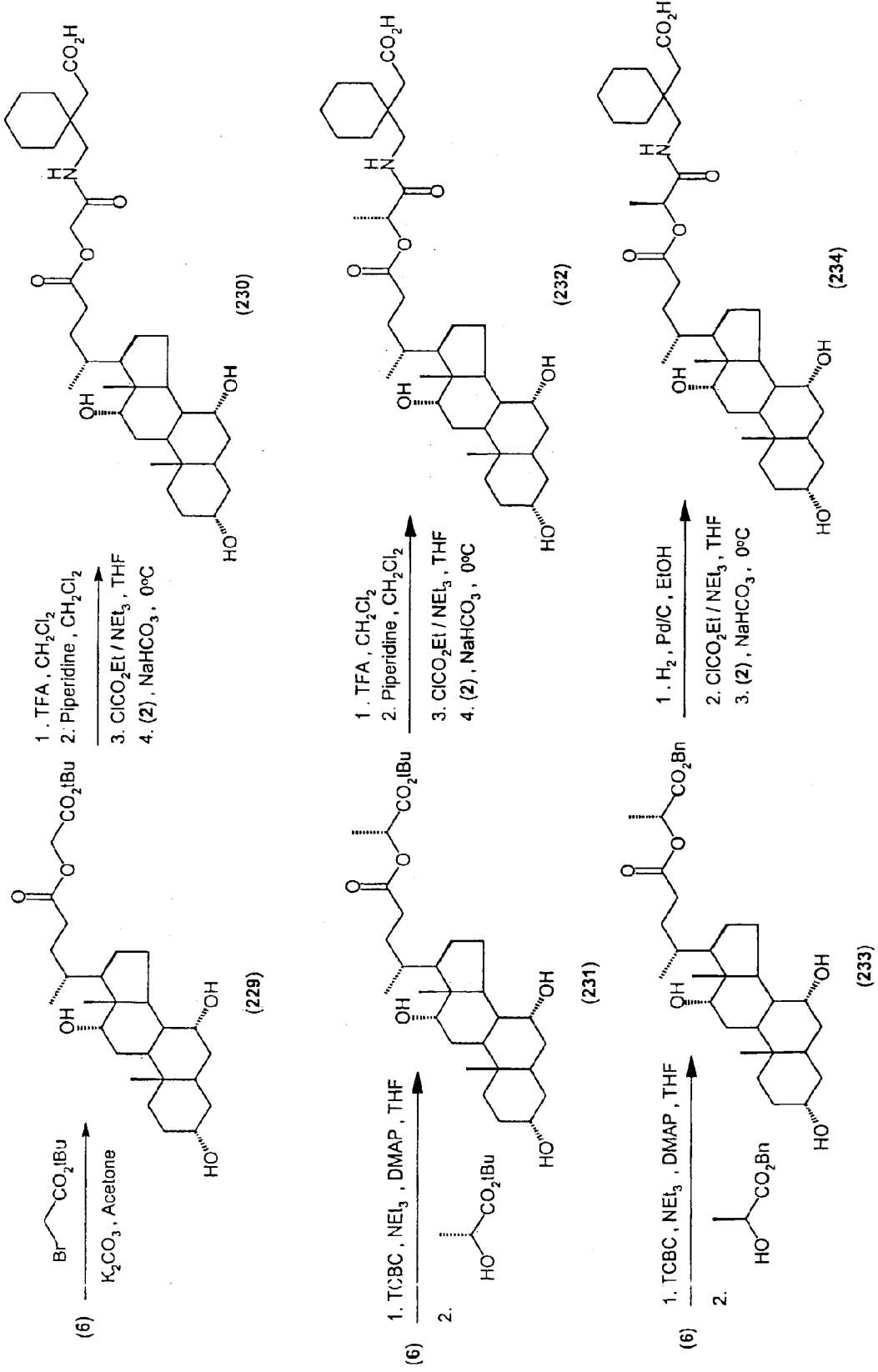
Figure 33:
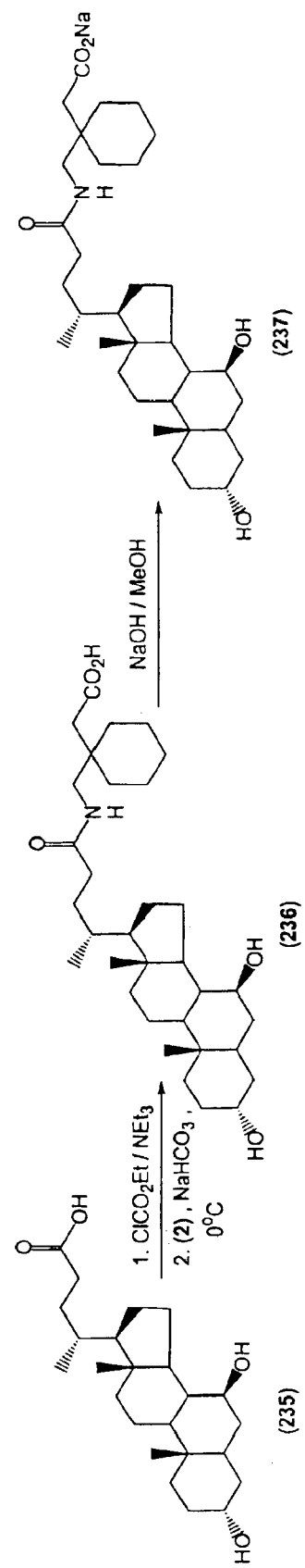

A compound of Formula (I) where $R^1$ and $R^2$ are hydroxy, X is a group of formula D—$Q^a$—(T)— where T is —O—, and D is a GABA analog moiety related to formula (a) that is attached to T through its carboxyl terminus can be prepared by reacting a compound of formula J (where R is a carboxyl protecting group) with a compound of formula (a) wherein $R^3$ is an amino protecting group and $R^{11}$ is —COL, wherein L is a suitable leaving group such as 2,4,6-trichlorobenzoyloxy to provide a compound of formula (I). The amino protecting group can be optionally removed to provide a corresponding compound of formula (I) where $R^3$ is hydrogen. A compound of formula (I) can be converted to other compounds of formula (I). For example, the carboxy group at the C-24 carbon can be converted to a —CONHCH$_2$—CH$_2$SO$_3$Na+ group by treating it with taurine as shown in FIG. 24 and described in Example 23 below.

Aditionally, FIGS. 11–33 and Working Examples 1–41 below describe in detail synthesis of various other compound of formula (I).

Pharmaceutical Formulations

When employed as pharmaceuticals, the compounds of formulae (I)–(III) are usually administered in the form of pharmaceutical compositions that are administered by oral routes. Such compositions are prepared in a manner well known in the pharmaceutical art and comprise at least one active compound.

This invention also includes pharmaceutical compositions that contain, as the active ingredient one or more of the compounds of formulae (I)–(III) above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, etc. containing, for example, up to 10% by weight of the active compound using, for example, soft and hard gelatin capsules.

In preparing a formulation, it may be necessary to mill the active compound to provide the appropriate particle size prior to combining with other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. ~40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.1 to about 5000 mg, more usually about 10 to about 2000 mg, of the active ingredient. The term "unit dosage forms" refers to physically discrete units suitable as unitary dosages for human subjects and other animals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 mg to about 2 g of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| Atm = | atmosphere |
| Boc = | tert-butyloxycarbonyl |
| Cbz = | carbobenzyloxy |
| CPM = | counts per minute |
| DIC = | diisopropylcarbodiimide |
| DMAP = | 4-N,N-dimethylaminopyridine |
| DMEM = | Dulbecco's minimun eagle medium |
| DMF = | N,N-dimethylformamide |
| DMSO = | dimethylsulfoxide |
| FMOC = | 9-fluorenylmethyloxycarbonyl |
| g = | gram |
| h = | hour |
| HBSS = | Hank's buffered saline solution |
| IBAT = | intestinal bile acid transporter |
| L = | liter |
| LBAT = | liver bile acid transporter |
| LC/MS = | liquid chromatography/mass spectroscopy |
| M = | molar |
| min = | minute |
| mL = | milliliter |
| mmol = | millimols |
| NTCP = | Na+ taurocholate cotransporting polypeptide |
| PBS = | phosphate buffered saline |
| PPTS = | pyridinium p-toluenesulfonate |
| TCBC = | 2,4,6-trichlorobenzoyl chloride |
| THF = | tetrahydrofuran |
| TFA = | trifluoroacetic acid |
| TMSOTf = | trimethylsilyltrifluoromethane-sulfonate |
| Trisyl = | 2,4,6-triisopropylbenzenesulfonyl |
| μL = | microliter |
| μM = | micromolar |
| v/v = | volume to volume |

Experimental Methods

The following examples illustrate how the synthesis of drug/linker/transporter conjugates could be conducted in order to prepare compounds of formula (I)–(III). The syntheses described below are illustrated in FIGS. 11–33.

Example 1

Synthesis of Compound (8)

Cholic acid (6) (408 mg, 1 mmol) was dissolved in anhydrous THF (10 mL) and tributylamine (0.285 mL, 1.2 mmol) added slowly with stirring. The solution was cooled to −5° C. in an ice-salt bath, and ethyl chloroformate (0.12 mL, 1.2 mmol) added slowly, maintaining the temperature between −5 to 0° C. After addition was complete, the cold mixture was stirred for an additional 15 minutes. A solution containing 1-aminomethyl-1-cyclohexaneacetic acid hydrochloride (Gabapentin, RBI Sigma) (2) (363 mg, 1.75 mmol) in 2N NaOH (3 mL) was added and the mixture stirred for an additional 60 min at −5 to 0° C. After removal of the THF in vacuo, saturated NaHCO$_3$ (15 mL) was added and the aqueous mixture washed with EtOAc (3×10 mL), then the pH adjusted to 3–4 with citric acid. The product was extracted into EtOAc (3×15 mL), and the combined organic phase dried over MgSO$_4$, and concentrated to dryness. The residue was purified by flash chromatography on silica gel (5% MeOH/CH$_2$Cl$_2$) to give pure free acid (7) (287 mg, 52% yield). Electrospray mass spectrometry showed the expected molecular ion at m/z=562.6 (M+H$^+$). The corresponding sodium salt (8) was prepared in quantitative yield from (7) (287 mg, 0.52 mmol) by addition of a methanol solution of (7) to water containing 0.5N NaOH (1 eq.) and evaporation to dryness on a lyophilizer.

MS (ESI): m/z=560.6 (M–Na$^{31}$). $^1$H NMR (CD$_3$OD, 400 MHz, characteristic resonances only): 3.34 (s, 2H), 2.28 (s, 2H), 1.03 (d, 3H, J=6.4 Hz), 0.91 (s, 3H), 0.70 (s, 3H).

Example 2
Synthesis of Compound (10)

Pregabalin (3), prepared according the methods described in Silverman et al (U.S. Pat. No. 5,563,175), is transformed to the cholyl amide (10) following the procedure detailed above for the gabapentin analog (8).

MS (ESI): m/z 548.39 (M–H$^-$), 550.41 (M+H$^+$). $^1$H NMR (CD$_3$OD, 400 MHz, characteristic resonances only): 1.03 (d, 3H, J=6.4 Hz), 0.91 (s, 3H), 0.83 (d, 3H, J=6.4 Hz), 0.81 (d, 3H, J=6.4 Hz), 0.70 (s, 3H).

Example 3
Synthesis Compounds (13) and (14)

Cholic acid (6) (408 mg, 1 mmol) was dissolved in anhydrous THF (10 mL) and tributylamine (0.285 mL, 1.2 mmol) added slowly with stirring. The solution was cooled to –5° C. in an ice-salt bath, and ethyl chloroformate (0.12 mL, 1.2 mmol) added slowly, maintaining the temperature between –5 to 0° C. After addition was complete, the cold mixture was stirred for an additional 15 minutes. A solution containing either glycine or phenylalanine (1.75 mmol) in 2N NaOH (2 mL) was added and the mixture stirred for an additional 60 min at –5 to 0° C. After removal of the THF in vacuo, saturated NaHCO$_3$ (15 mL) was added and the aqueous mixture washed with EtOAc (3×10 mi]L), then the pH adjusted to 3–4 with citric acid. The product was extracted into EtOAc (3×15 mL), and the combined organic phase dried over MgSO$_4$, and concentrated to dryness. The residue was purified by flash chromatography on silica gel (5% MeOH/CH$_2$Cl$_2$) to give pure free acids (11) and (12) (270 mg, 58% yield for (11)). Electrospray mass spectrometry showed the expected molecular ion at m/z=466.5 (for (11)) and 556.6 (for (12)) (M+H$^+$). These adducts (0.2 mmol) were dissolved in anhydrous THF (5 mL) and tributylamine (0.22 mmol) added slowly with stirring. The solutions were cooled to –5° C. in an ice-salt bath, and ethyl chloroformate (22 μL, 0.22 mmol) added slowly, maintaining the temperature between –5 to 0° C. After addition was complete, the cold mixtures were stirred for an additional 15 minutes. A solution containing Gabapentin (2) (83 mg, 0.4 mmol) in 2N NaOH (1.5 mL) was added and the mixtures stirred for an additional 60 min at –5 to 0° C. After removal of the THF in vacuo, saturated NaHCO$_3$ (5 mL) was added and the aqueous mixtures washed with EtOAc (3×5 mL), then the pH adjusted to 3–4 with citric acid. The products were extracted into EtOAc (3×10 mL), and the combined organic phases dried over MgSO$_4$, and concentrated to dryness. The residues were purified by flash chromatography on silica gel (10% MeOH/CH$_2$Cl$_2$) to give pure free acids. The corresponding sodium salts (13) and (14) were prepared in quantitative yield by addition of a methanol solution of the acids to water containing 0.5N NaOH (1 eq.) and evaporation to dryness on a lyophilizer.

Cholyl-Gly-Gabapentin (13): MS (ESI): m/z 617.50 (M–H$^-$), 619.51 (M+H$^+$).

$^1$H NMR (CD$_3$OD, 400 MHz, characteristic resonances only): 3.81 (s, 2H), 3.34 (s, 2H), 2.28 (s, 2H), 1.03 (d, 3H, J=6.4 Hz), 0.91 (s, 3H), 0.70 (s, 3H).

Cholyl-Phe-Gabapentin (14): MS (ESI): m/z 707.47 (M–H$^-$), 709.36 (M+H$^+$). $^1$H NMR (CD$_3$OD, 400 MHz, characteristic resonances only): 7.26 (m, 5H), 4.59 (m, 1H), 3.34 (s, 2H), 3.25–2.95 (m, 2H), 2.18 (d, 2H, J=7.2 Hz), 0.98 (d, 3H, J=6.4 Hz), 0.91 (s, 3H), 0.68 (s, 3H).

Example 4
Synthesis of Compounds (15) and (16)

Pregabalin (3) is transformed to the cholylglycine and cholylphenylalanine adducts (15) and (16) following the procedure detailed above for the gabapentin analogs (13) and (14).

Cholyl-Gly-Pregabalin (15): MS (ESI): m/z 605.57 (M–H$^-$), 607.55 (M+H$^+$). $^1$H NMR (CD$_3$OD, 400 MHz, characteristic resonances only): 3.81 (s, 2H), 1.03 (d, 3H, J=6.4 Hz), 0.91 (s, 3H), 0.83 (d, 3H, J=6.4 Hz), 0.81 (d, 3H, J=6.4 Hz), 0.70 (s, 3H).

Cholyl-Gly-Pregabalin (16): MS (ESI): m/z 695.58 (M–H$^-$), 697.53 (M+H$^+$). $^1$H NMR (CD$_3$OD, 400 MHz, characteristic resonances only): 7.25 (m, 5H), 4.60 (m, 1H), 3.25–2.95 (m, 2H), 1.03 (d, 3H, J=6.4 Hz), 0.91 (s, 3H), 0.83 (d, 3H, J=6.4 Hz), 0.81 (d, 3H, J=6.4 Hz), 0.70 (s, 3H).

Example 5
Synthesis of Compounds (23)–(26)

Cholic acid (6) (1 mmol) is dissolved in anhydrous THF (10 mL) and tributylamine (1.2 mmol) added slowly with stirring. The solution is cooled to –5° C. in an ice-salt bath, and ethyl chloroformate (1.2 mmol) added slowly, maintaining the temperature between –5 to 0° C. After addition is complete, the cold mixture is stirred for an additional 15 minutes. A solution containing the α-tert-butyl ester of either aspartic acid or glutamic acid (1.75 mmol) in 2N NaOH (2 mL) is added and the mixtures stirred for an additional 60 min at –5 to 0° C. After removal of the THF in vacuo, saturated NaHCO$_3$ (15 mL) is added and the aqueous mixtures washed with EtOAc (3×10 mL), then the pH adjusted to 3–4 with citric acid. The products are extracted into EtOAc (3×15 mL), and the combined organic phases dried over MgSO$_4$, and concentrated to dryness. The residues are purified by flash chromatography on silica gel to give pure acids (17) and (18). These acids (0.4 mmol) are dissolved in anhydrous THF (10 mL) and tributylamine (0.45 mmol) added slowly with stirring. The solutions are cooled to –5° C. in an ice-salt bath, and ethyl chloroformate (0.45 mmol) added slowly, maintaining the temperature between –5 to 0° C. After addition is complete, the cold mixtures are stirred for an additional 15 minutes. A solution containing Gabapentin (2) (0.7 mmol) in 2N NaOH (3 mL) is added and the mixtures stirred for an additional 60 min at –5 to 0° C. After removal of the THF in vacuo, saturated NaHCO$_3$ (10 mL) is added and the aqueous mixtures washed with EtOAc (3×10 mL), then the pH adjusted to 3–4 with citric acid. The products are extracted into EtOAc (3×15 mL), and the combined organic phases dried over MgSO$_4$, and concentrated to dryness. The residues are purified by flash chromatography on silica gel to give pure free acids (19) and (20). The acids (0.15 mmol) are dissolved in methanol (15 mL) and a freshly prepared solution of diazomethane in diethyl ether added until a pale yellow color persists. After stirring for 60 min, the solvent is removed in vacuo to afford the methyl ester derivatives (21) and (22). The tert-butyl esters (19)–(22) are transformed to the corresponding sodium salts (23)–(26) by first treating with 50% (v/v) TFA in CH$_2$Cl$_2$ for 30 min, purification of the resulting acids by flash chromatography on silica gel, and finally addition of methanolic solutions of the acids to water containing 0.5N NaOH (1 eq.) then evaporation to dryness on a lyophilizer.

Example 6
Synthesis of Compounds (30) and (31)

Cholic acid (6) (1 mmol) is dissolved in anhydrous THF (10 mL) and tributylamine (1.2 mmol) added slowly with stirring. The solution is cooled to −5° C. in an ice-salt bath, and ethyl chloroformate (1.2 mmol) added slowly, maintaining the temperature between −5 to 0° C. After addition is complete, the cold mixture is stirred for an additional 15 minutes. A solution containing the S-Trityl thioether derivative of cysteine (1.5 mmol) and 2N NaOH (2 mL) in THF (15 mL) is added and the mixture stirred for an additional 60 min at −5 to 0° C. After removal of the THF in vacuo, saturated NaHCO$_3$ (15 mL) is added and the aqueous mixture washed with EtOAc (3×10 mL), then the pH adjusted to 3–4 with citric acid. The product is extracted into EtOAc (3×15 mL), and the combined organic phase dried over MgSO$_4$, and concentrated to dryness. The residue is purified by flash chromatography on silica gel to give pure acid (27). (27) (0.4 mmol) is dissolved in anhydrous THF (10 mL) and tributylamine (0.45 mmol) added slowly with stirring. The solution is cooled to −5° C. in an ice-salt bath, and ethyl chloroformate (0.45 mmol) added slowly, maintaining the temperature between −5 to 0° C. After addition is complete, the cold mixture is stirred for an additional 15 minutes. A solution containing gabapentin (2) (0.7 mmol) in 2N NaOH (3 mL) is added and the mixture stirred for an additional 60 min at −5 to 0° C. After removal of the THF in vacuo, saturated NaHCO$_3$ (10 mL) is added and the aqueous mixture washed with EtOAc (3×10 mL), then the pH adjusted to 3–4 with citric acid. The product is extracted into EtOAc (3×15 mL), and the combined organic phase dried over MgSO$_4$, and concentrated to dryness. The residue is purified by flash chromatography on silica gel to give gabapentin adduct (28). A portion of this product (0.15 mmol) is dissolved in MeOH (15 mL) and a freshly prepared solution of diazomethane in diethyl ether added until a pale yellow color persists. After stirring for 60 min, the solvent is removed in vacuo to afford the methyl ester derivative (29). Compounds (28) and (29) (0.15 mmol) are treated with 50% (v/v) TFA in CH$_2$Cl$_2$ for 30 min and the solvent removed in vacuo. The residues are dissolved in MeOH (15 mL) and vigorously stirred with an aqueous solution containing 30% (v/v) H$_2$O$_2$ and 2% H$_2$SO$_4$ (15 mL) for 48 h to oxidize the sulfhydryl moieties to sulfonic acids. The solvent is removed in vacuo and the residues purified by flash chromatography on silica gel. Sodium salts of the gabapentin-cholyl cysteate conjugates (30) and (31) are prepared by dissolving each residue in 50% MeOH/H$_2$O (5 mL) and stirring with Na$^+$ cation exchange resin (prepared from Dowex HCR-W2, ~1 mmol) for 30 min. The resins are washed with 50% MeOH/H$_2$O (3×5 mL) and the combined filtrates evaporated to dryness to afford compounds (30) and (31).

Example 7
Synthesis of Compound (35)

Cholic acid (6) (1 mmol) is dissolved in anhydrous THF (10 mL) and tributylamine (1.2 mmol) added slowly with stirring. The solution is cooled to −5° C. in an ice-salt bath, and ethyl chloroformate (1.2 mmol) added slowly, maintaining the temperature between −5 to 0° C. After addition is complete, the cold mixture is stirred for an additional 15 minutes. A solution containing the O-tert-butyl ether derivative of serine (1.5 mmol) and 2N NaOH (2 mL) in THF (10 mL) is added and the mixture stirred for an additional 60 min at −5 to 0° C. After removal of the THF in vacuo, saturated NaHCO$_3$ (15 mL) is added and the aqueous mixture washed with EtOAc (3×10 mL), then the pH adjusted to 3–4 with citric acid. The product is extracted into EtOAc (3×15 mL), and the combined organic phase dried over MgSO$_4$, and concentrated to dryness. The residue is purified by flash chromatography on silica gel to give pure acid (32). (32) (0.4 mmol) is dissolved in anhydrous THF (10 mL) and tributylamine (0.45 mmol) added slowly with stirring. The solution is cooled to −5° C. in an ice-salt bath, and ethyl chloroformate (0.45 mmol) added slowly, maintaining the temperature between −5 to 0° C. After addition is complete, the cold mixture is stirred for an additional 15 minutes. A solution containing gabapentin (2) (0.7 mmol) in 2N NaOH (3 mL) is added and the mixture stirred for an additional 60 min at −5 to 0° C. After removal of the THF in vacuo, saturated NaHCO$_3$ (10 mL) is added and the aqueous mixture washed with EtOAc (3×10 mL), then the pH adjusted to 3–4 with citric acid. The product is extracted into EtOAc (3×15 mL), and the combined organic phase dried over MgSO$_4$, and concentrated to dryness. The residue is purified by flash chromatography on silica gel to give the cholylserine gabapentin acid adduct. This product is dissolved in MeOH (25 mL) and a freshly prepared solution of diazomethane in diethyl ether added until a pale yellow color persists. After stirring for 60 min, the solvent is removed in vacuo to afford the methyl ester derivative (33).

Compound (33) is peracetylated following literature methods (Opsenica et al, 2000). Briefly, (33) (0.5 mmol) is dissolved in a solution containing Ac$_2$O (1 mL) and TMSOTf (0.15 mmol) and stirred at room temperature for 5 min. The reaction is quenched by addition of saturated NaHCO$_3$ (10 mL), the product is extracted into EtOAc (3×15 mL) and the combined organic phase dried over MgSO$_4$, and concentrated to dryness. The residue is purified by flash chromatography on silica gel and then treated with 50% (v/v) TFA in CH$_2$Cl$_2$ for 60 min to generate alcohol (34). Compound (34) (0.5 mmol) is dissolved in DMF (5 mL) containing py.SO$_3$ (0.55 mmol) and stirred for 4 h at room temperature. After removal of the solvent in vacuo, the residue is dissolved in dry MeOH (5 mL) and stirred with anhydrous K$_2$CO$_3$ (1.5 mmol) for 24 h and the solvent again removed in vacuo. Dowex HCR-W2 ion exchange resin (H$^+$ form) is converted to the Na$^+$ form by treatment with 1N NaOH for 30 min, followed by extensive washing with water till neutral. The crude sulfate compound is dissolved in 50% MeOH/H$_2$O (10 mL) and the Na$^+$ cation exchange resin (~2 mmol) is added. The resulting mixture is shaken for 30 min and filtered. The resin is washed with 50% MeOH/H$_2$O (3×10 mL) and the combined filtrates evaporated to dryness to afford the sodium salt of O-sulfate compound (35).

Example 8
Synthesis of Compound (39)

1,1-Cyclohexanediacetic acid (4 g, 20 mmol) and acetic anhydride (3.8 mL, 40 mmol) were heated under reflux until a clear solution was obtained (~1 h), and heating continued for a further hour to ensure the reaction had gone to completion. The mixture was cooled to room temperature and the solvent removed in vacuo to afford 1,1-cyclohexanediacetic anhydride (37) (3.6 g, 99% yield). Electrospray mass spectrometry showed the expected molecular ion at m/z=183.2 (M+H$^+$).

(37) (3.6 g 19.7 mmol) was stirred in 0.5M sodium methoxide/MeOH solution (40 mL) at room temperature for 2 h. After removal of the solvent in vacuo, 0.5 N HCl (20 mL) was added to the residue and the product extracted with EtOAc (3×30 mL). The combined organic phase was dried over MgSO$_4$ and concentrated in vacuo to give monomethyl ester (38) (4 g, 95% yield). Electrospray mass spectrometry showed the expected molecular ion at m/z 213.3 (M−H$^-$).

To a solution of (38) (1.6 g, 7.5 mmol) in anhydrous acetone (10 mL) was slowly added triethylamine (1.25 mL, 9 mmol). The solution was cooled to −5 to 0° C. in an ice-salt bath and ethyl chloroformate (0.89 mL, 9 mmol) in anhydrous acetone (10 mL) was added dropwise, maintaining the temperature between −5 to 0° C. After addition was complete, the cold mixture was stirred for an additional 15 min. A solution of sodium azide (975 mg, 15 mmol) in water (3 mL) was then added slowly, the temperature being maintained between −5 to 0° C. The mixture was stirred for an additional 30 min, poured into ice water (5 mL), and shaken with toluene (4×25 mL). The combined toluene extracts were dried over $MgSO_4$ and the resulting acyl azide (39) used immediately in a Curtius reaction with the appropriate alcohol (vide infra).

Example 9
Synthesis of Compound (43)

Sodium hydride (252 mg, 10 mmol) was suspended in dry THF (100 mL) under nitrogen and 3-hydroxypropylnitrile (40) (683 μL, 10 mmol) added slowly. The mixture was stirred at room temperature for 30 min, and then filtered under nitrogen to give a 0.1 M THF solution of sodium 2-cyanoethoxide (41). This solution could be stored at −20° C. for later use.

(37) (1.82 g, 10 mmol) was treated with this 0.1 M sodium 2-cyanoethoxide solution in THF (100 mL) for 2 hours at room temperature. After removal of the solvent in vacuo, the residue was treated with saturated citric acid solution (20 mL) and the product extracted with EtOAc (3×30 mL). The combined organic phase was dried over $MgSO_4$, the solvent removed in vacuo, and the cyanoethyl ester product (42) (1.8 g, 71% yield) purified by flash chromatography on silica gel ($CH_2Cl_2$—MeOH 97:3). Electrospray mass spectrometry showed the expected molecular ion at m/z=276.3 (M+Na$^+$).

To a solution of (42) (0.7 g, 2.8 mmol) in anhydrous acetone (5 mL) was slowly added triethylamine (0.47 mL, 3.4 mmol). The solution was cooled to −5 to 0° C. in an ice-salt bath and ethyl chloroformate (0.34 ML, 3.4 mmol) in anhydrous acetone (4 mL) was added dropwise, maintaining the temperature between −5 to 0° C. After addition was complete, the cold mixture was stirred for an additional 15 min. A solution of sodium azide (440 mg, 6.8 mmol) in water (1 mL) was then added slowly, the temperature being maintained between −5 to 0° C. The mixture was stirred for an additional 30 min, poured into ice water (5 mL), and shaken with toluene (4×10 mL). The combined toluene extracts were dried over $MgSO_4$ and the resulting acyl azide (43) used immediately in a Curtius reaction with the appropriate alcohol (vide infra).

Example 10
Synthesis of Compound (45)

23-Nor-5β-cholanic acid-3α,7α,12α-triol (212) is prepared from cholic acid according to the methods of Ayra and Burton (U.S. Pat. No. 5,541,348). (212) (5 mmol) is stirred under nitrogen at room temperature overnight in a solution containing pyridine (2 mL), acetic anhydride (10 mL), DMAP (0.5 mmol) and $CH_2Cl_2$ (30 mL). The mixture is washed with a saturated aqueous solution of $NH_4Cl$, the organic layer dried over $MgSO_4$ and the solvent removed in vacuo. A solution of the resulting tri-O-acetyl derivative (2 mmol) in $CCl_4$ (150 mL) containing iodosobenzene diacetate (1.1 mmol) and iodine (1 mmol) is irradiated with two 100-W tungsten-filament lamps at reflux temperature for 45 min. Additional portions of iodosobenzene diacetate (1.1 mmol) and iodine (1 mmol) are added and irradiation continued at this temperature for 45 min. The mixture is washed with dilute aqueous sodium thiosulfate and the iodo-derivative (213) purified by flash chromatography on silica gel.

(213) (1 mmol) is heated at 40° C. in DMSO (5 mL) containing potassium acetate (1.5 mmol) and 18-crown-6 (1 mmol) for 2 h. A solution of 2N NaOH (2.5 mL) is added and stirring continued for an additional 4 h. After removal of the solvent in vacuo, the residue is treated with a saturated aqueous solution of $NH_4Cl$ and extracted with EtOAc (3×10 mL). The combined organic phase is dried over $MgSO_4$, the solvent removed in vacuo, and the bis-norcholanol (214) purified by flash chromatography on silica gel.

(214) (0.5 mmol) is heated under reflux in a toluene solution containing acyl azide (43) (2 mmol) for 12 h. The solvent is removed in vacuo, the residue dissolved in EtOAc (10 mL), washed with water (2×5 mL) and dried over $MgSO_4$. After removal of the solvent in vacuo, the cyanoethyl ester product (44) is purified by preparative TLC on silica gel. (44) is treated with 20% (v/v) piperidine in $CH_2Cl_2$ (5 mL) for 30 min and the solvent removed in vacuo. Aqueous citric acid (pH 3–4) is added to the residue, the crude acid extracted with EtOAc (3×5 mL) and the organic layer dried over $MgSO_4$. Purification by preparative TLC on silica gel afforded gabapentin carbamate (45).

Example 11
Synthesis of Compound (47)

Cholic acid (6) (1 mmol) is dissolved in anhydrous THF (10 mL) and tributylamine (1.2 mmol) added slowly with stirring. The solution is cooled to −5° C. in an ice-salt bath, and ethyl chloroformate (1.2 mmol) added slowly, maintaining the temperature between −5 to 0° C. After addition is complete, the cold mixture is stirred for an additional 15 minutes. A solution containing the α-tert-butyl ester of serine (1.75 mmol) in 2N NaOH (2 mL) is added and the mixture stirred for an additional 60 min at −5 to 0° C. After removal of the THF in vacuo, saturated aqueous citric acid (pH ~3) (15 mL) is added, the product is extracted into EtOAc (3×15 mL), and the combined organic phase dried over $MgSO_4$, and concentrated to dryness. The residue is purified by flash chromatography on silica gel to give cholylserine derivative (46).

(46) (0.5 mmol) is heated under reflux in a toluene solution containing acyl azide (39) (2 mmol) for 12 h. The solvent is removed in vacuo, the residue dissolved in EtOAc (10 mL), washed with water (2×5 mL) and dried over $MgSO_4$. After removal of the solvent in vacuo, the resulting carbamate adduct is purified by preparative TLC on silica gel. This material is converted to the corresponding carboxylic acid (47) by treatment with 50% (v/v) TFA in $CH_2Cl_2$ for 30 min followed by preparative TLC on silica gel.

Example 12
Synthesis of Compound (52)

Phosphonoacetic acid ethyl ester (48) (10 mmol) is stirred in dioxane (20 mL) with diisopropylethylamine (DIEA, 20 mmol) and benzyl bromide (20 mmol) for 4 h at room temperature. After removal of the solvent in vacuo, product (49) is purified by flash chromatography on silica gel.

(49) (10 mmol) is dissolved in anhydrous THF (25 mL) and cooled to −78° C. A 0.5M toluene solution of potassium hexamethyldisilazide (12 mmol) is added slowly followed by dropwise addition of a 2M THF solution of trisyl azide. After stirring for 2 h at −78° C., the solution is allowed to warm to room temperature and the solvent is removed in vacuo. The resulting azidophosphonate is purified by flash chromatography on silica gel, dissolved in THF and treated with triphenylphosphine (12 mmol) and water (12 mmol). After stirring for 8 h, the solvent is removed in vacuo and the residue partitioned between $CH_2Cl_2$ and 0.5M aqueous KHSO$_4$ (pH=3–4). The organic layer is discarded and the aqueous phase basified to pH ~9 with 0.5M Na$_2$CO$_3$. The crude aminophosphonate (50) is isolated by extraction into EtOAc (3×20 mL), and after removal of the solvent in vacuo, used as is in the subsequent reaction.

Cholic acid (6) (1 mmol) is dissolved in anhydrous THF (10 mL) and tributylamine (1.2 mmol) added slowly with stirring. The solution is cooled to −5° C. in an ice-salt bath, and ethyl chloroformate (1.2 mmol) added slowly, maintaining the temperature between −5 to 0° C. After addition is complete, the cold mixture is stirred for an additional 15 minutes. A solution containing (50) (1.5 mmol) and pyridine (1 mL) in THF (5 mL) is added and the mixture stirred for an additional 60 min at −5 to 0° C. After removal of the solvent in vacuo, saturated aqueous citric acid (pH ~3) (15 mL) is added, the product is extracted into EtOAc (3×15 mL), and the combined organic phase dried over MgSO$_4$, and concentrated to dryness. The residue is dissolved in EtOH (10 mL) and sodium borohydride (1.5 mmol) added with stirring. After warming the solution to 40° C. for 2 h, the solvent is removed in vacuo and the residue purified by flash chromatography on silica gel to afford alcohol (51).

(51) (0.5 mmol) is heated under reflux in a toluene solution containing acyl azide (39) (2 mmol) for 12 h. The solvent is removed in vacuo, the residue dissolved in EtOAc (10 mL), washed with water (2×5 mL) and dried over MgSO$_4$. After removal of the solvent in vacuo, the resulting carbamate adduct is purified by preparative TLC on silica gel. This material is converted to the sodium salt of the corresponding carboxylic acid, (52), by hydrogenation over 5% palladium on charcoal (8 h in EtOAc/HOAc), removal of the solvent in vacuo, and dissolution of the residue in 50% MeOH/H$_2$O (5 mL) and stirring with Na$^+$ cation exchange resin (prepared from Dowex HCR-W2, ~2 mmol) for 30 min. The resin is washed with 50% MeOH/H$_2$O (3×5 mL) and the combined filtrates evaporated to dryness to afford compound (52).

Example 13
Synthesis of Compound (55)

(27) (1 mmol) is dissolved in anhydrous THF (10 mL) and tributylamine (1.2 mmol) added slowly with stirring. The solution is cooled to −5° C. in an ice-salt bath, and ethyl chloroformate (1.2 mmol) added slowly, maintaining the temperature between −5 to 0° C. After addition is complete, the cold mixture is stirred for an additional 15 minutes then a solution of sodium borohydride (1.5 mmol) in EtOH (5 mL) added and the mixture stirred at room temperature for 2 h. After removal of the solvent in vacuo, the residue is purified by flash chromatography on silica gel to afford alcohol (54).

(54) (0.5 mmol) is heated under reflux in a toluene solution containing acyl azide (39) (2 mmol) for 12 h. The solvent is removed in vacuo, the residue dissolved in EtOAc (10 mL), washed with water (2×5 mL) and dried over MgSO$_4$. After removal of the solvent in vacuo, the resulting carbamate adduct is purified by preparative TLC on silica gel. This material is converted to the corresponding carboxylic acid by treatment with 50% (v/v) TFA in CH$_2$Cl$_2$ for 30 min and the solvent is removed in vacuo. The residue is dissolved in MeOH (5 mL) and vigorously stirred with an aqueous solution containing 30% (v/v) H$_2$O$_2$ and 2% H$_2$SO$_4$ (5 mL) for 48 h to oxidize the sulfhydryl moiety to the sulfonic acid. The solvent is removed in vacuo and the residue purified by flash chromatography on silica gel. The sodium salt (55) is prepared by dissolution of the sulfonic acid in 50% MeOH/H$_2$O (5 mL) and stirring with Na$^+$ cation exchange resin (prepared from Dowex HCR-W2, ~2 mmol) for 30 min. The resin is washed with 50% MeOH/H$_2$O (3×5 mL) and the combined filtrates evaporated to dryness to afford compound (55).

Example 14
Synthesis of Compounds (60) and (61)

A suspension of mercuric oxide (5 mmol) and cholic acid (6) (10 mmol) in CH$_2$Cl$_2$ (75 mL) is stirred overnight at room temperature. 10 mmol of either chloromethyl 4-nitrophenyl carbonate (56) (Maybridge) or 2-chloroisopropyl 4-nitrophenyl carbonate (57) (prepared as described by Alexander, U.S. Pat. No. 5,684,018) is added to this suspension and stirring continued for 24 h. The solutions are washed with saturated NaHCO$_3$, water and brine and the organic phase evaporated to dryness. The residues are purified by flash chromatography on silica gel to afford carbonates (58) and (59) respectively.

(58) or (59) (1 mmol each) is dissolved in dioxane (10 mL) and a solution of gabapentin (2) (1 mmol) in aqueous phosphate buffer at pH ~8.5 (1 mL) added with vigorous stirring. After 2 h, the solvent is removed in vacuo, the residues treated with aqueous citric acid (pH 3–4) and extracted with EtOAc (3×10 mL). The combined organic phases are dried over MgSO$_4$, concentrated to ~5 mL and purified by flash chromatography on silica gel. Neutralization of the gabapentin acyloxyalkylcarbamates with 0.5N NaOH afforded sodium salts (60) and (61).

Example 15
Synthesis of Compounds (74)–(81)

A suspension of mercuric oxide (1 mmol) and either (17) or (18) (2 mmol) in CH$_2$Cl$_2$ (15 mL) is stirred overnight at room temperature. 2 mmol of either (56) or (57) is added to these suspensions and stirring continued for 24 h. The four solutions are washed with saturated NaHCO$_3$, water and brine and the organic phase evaporated to dryness. The residues are purified by flash chromatography on silica gel to afford carbonates (62)–(65).

(62)–(65) (1 mmol each) are dissolved in dioxane (10 mL) and a solution of gabapentin (2) (1 mmol) in aqueous phosphate buffer at pH ~8.5 (1 mL) added with vigorous stirring. After 2 h, the solvent is removed in vacuo, the residues treated with aqueous citric acid (pH 3–4) and extracted with EtOAc (3×10 mL). The combined organic phases are dried over MgSO$_4$, concentrated to ~5 mL and purified by flash chromatography on silica gel to afford the acids (66)–(69).

(66)–(69) (1 mmol each) are dissolved in methanol (15 mL) and a freshly prepared solution of diazomethane in diethyl ether added until a pale yellow color persists. After stirring for 60 min, the solvent is removed in vacuo to afford the methyl ester derivatives (70)–(73).

(66)–(73) (1 mmol each) are treated with 50% (v/v) TFA in CH$_2$Cl$_2$ for 30 min and the solvent removed in vacuo. The acids are converted to the corresponding sodium salts by dissolving each residue in 50% MeOH/H$_2$O (5 mL) and stirring with Na$^+$ cation exchange resin (prepared from Dowex HCR-W2, ~2 mmol) for 30 min. The resins are washed with 50% MeOH/H$_2$O (3×5 mL) and the combined filtrates evaporated to dryness to afford (74)–(81).

Example 16
Synthesis of Compounds (88)–(91)

A suspension of mercuric oxide (1 mmol) and (27) (2 mmol) in CH$_2$Cl$_2$ (15 mL) is stirred overnight at room temperature. 2 mmol of either (56) or (57) is added to this suspension and stirring continued for 24 h. The solutions are washed with saturated NaHCO$_3$, water and brine and the organic phase evaporated to dryness. The residues are purified by flash chromatography on silica gel to afford carbonates (82) and (83).

(82) and (83) (1 mmol each) are dissolved in dioxane (10 mL) and a solution of gabapentin (2) (1 mmol) in aqueous phosphate buffer at pH ~8.5 (1 mL) added with vigorous stirring. After 2 h, the solvent is removed in vacuo, the residues treated with aqueous citric acid (pH 3–4) and extracted with EtOAc (3×10 mL). The combined organic phases are dried over $MgSO_4$, concentrated to ~5 mL and purified by flash chromatography on silica gel to afford the acids (84) and (85).

(84) and (85) (1 mmol each) are dissolved in methanol (15 mL) and a freshly prepared solution of diazomethane in diethyl ether added until a pale yellow color persists. After stirring for 60 min, the solvent is removed in vacuo to afford the methyl ester derivatives (86) and (87).

(84)–(87) (1 mmol each) are treated with 50% (v/v) TFA in $CH_2Cl_2$ for 30 min and the solvent removed in vacuo. The residues are dissolved in MeOH (5 mL) and vigorously stirred with an aqueous solution containing 30% (v/v) $H_2O_2$ and 2% $H_2SO_4$ (5 mL) for 48 h to oxidize the sulfhydryl moieties to sulfonic acids. The solvent is removed in vacuo and the residues purified by flash chromatography on silica gel. The acids are converted to the corresponding sodium salts by dissolving each compound in 50% $MeOH/H_2O$ (5 mL) and stirring with $Na^+$ cation exchange resin (prepared from Dowex HCR-W2, ~2 mmol) for 30 min. The resins are washed with 50% $MeOH/H_2O$ (3×5 mL) and the combined filtrates evaporated to dryness to afford (88)–(91).

Example 17
Synthesis of Compounds (92)–(103)

Compounds (92)–(103) are prepared following methods described in U.S. Provisional Patent Application Ser. No. 60/238,758 of Gallop and Cundy entitled "Bile Acid—Derived Compounds for Enhancing Oral Absorption and Systemic Bioavailability of Drugs" filed on Oct. 6, 2000 which application is incorporated herein by reference in its entirety.

Example 18
Synthesis of Compound (104)

A solution of di-tert-butyl carbonate (10 mmol) in dioxane (5 mL) is added to a solution containing gabapentin (2) (10 mmol) and potassium carbonate (5 mmol) in 75% (v/v) dioxane/water (5 mL) cooled to 5° C. After stirring for 2 h, the solvent is removed in vacuo and the residue partitioned between aqueous citric acid (pH 3) and EtOAc. The organic phase is dried over $MgSO_4$, and evaporated to dryness yielding Boc-protected gabapentin (104).

Example 19
Synthesis of Compound (105)

A solution of ethyl chloroformate (10 mmol) in dioxane (5 mL) is added to a solution containing gabapentin (2) (10 mmol) and potassium carbonate (5 mmol) in dioxane (5 mL) cooled to 5° C. After stirring for 2 h, the solvent is removed in vacuo and the residue partitioned between aqueous citric acid (pH 3) and EtOAc. The organic phase is dried over $MgSO_4$, and evaporated to dryness yielding ethyl carbamate (105).

Example 20
Synthesis of Compound (108)

A solution containing ethyl 6-hydroxyhexanoate (106) (162 μL, 1 mmol), 3,4-dihydro-2H-pyran (137 μL, 1.5 mmol) and pyridium p-toluenesulfonate (25 mg, 0.1 mmol) in dry $CH_2Cl_2$ (10 mL) was stirred at room temperature for 4 h. $CH_2Cl_2$ (10 mL) was added and the reaction mixture and washed with brine (3×5 mL). The organic phase was dried over $MgSO_4$ and evaporated to dryness yielding (107). The resulting residue was treated with aqueous 0.5 N NaOH (10 mL) and MeOH (10 mL) at 60° C. for 2 h. After removal of MeOH in vacuo and washing with $CH_2Cl_2$ (10 mL), the aqueous phase was acidified with citric acid. Extraction with ether (3×15 mL) and concentration in vacuo gave the THP-protected hydroxy-acid (108) (216 mg, 100% yield), which was used without further purification. Electrospray mass spectrometry showed the expected molecular ion at m/z=215.3 (M−H⁻).

Example 21
Synthesis of Compound (109)

To a solution of cholic acid (6) (2.04 g, 5 mmol) in dry THF (100 mL) was added triethylamine (765 μL, 5.5 mmol) followed by 2,4,6-trichlorobenzoylchloride (858 μL, 5.5 mmol). After 10 min a solution of 3-hydroxypropylnitrile (40) (341 μL, 5 mmol) in dry THF was added followed by DMAP (65 mg). The mixture was stirred at room temperature for 18 h. The reaction mixture was washed with saturated $NaHCO_3$ (10 mL) then saturated aqueous citric acid (3×10mL). The organic phase was dried over $MgSO_4$, the solvent removed in vacuo and the residue purified by flash chromatography on silica gel ($CH_2Cl_2$—MeOH 97:3) to give pure cyanoethyl cholate (109) (2.05 g, 89% yield).

MS (ESI): m/z=462.6 (M+H⁺). $^1$H NMR (CD$_3$OD, 400 MHz, characteristic resonances only): 4.27 (t, 2H, J=6 Hz), 2.70 (t, 2H, J=6 Hz), 0.99 (d, 3H, J=6.4 Hz), 0.88 (s, 3H), 0.68 (s, 3H).

Example 22
Synthesis of Compounds (112) and (113)

To a solution of (105) (1 mmol) in dry THF (10 mL) is added triethylamine (1.1 mmol) followed by 2,4,6-trichlorobenzoylchloride (1.1 mmol). After 10 min a solution of either (92) or (93) (1 mmol each) in dry THF (5 mL) is added followed by DMAP (0.5 mmol). The mixture is stirred at room temperature for 18 h. The reaction mixture is washed with saturated $NaHCO_3$ (10 mL) then saturated aqueous citric acid (3×10 mL). The organic phase is dried over $MgSO_4$, the solvent removed in vacuo and the residue purified by flash chromatography on silica gel to give respectively the 3α- and 3β-tert-butyl cholate derivatives. These are treated with 50% (v/v) TFA in $CH_2Cl_2$ for 30 min and the solvent removed in vacuo to afford (110) and (111).

(110) and (111) (1 mmol) are each dissolved in dry dioxane (10 mL) containing tri-n-butylamine (2 mmol), cooled to 0° C., and ethyl chloroformate (1 mmol) added dropwise. After stirring for 20 min a solution of taurine (2 mmol) in 2 M aqueous NaOH (1 mL) is slowly added and the mixtures warmed to room temperature with stirring for 2 h. The mixtures are poured into water (20 mL), neutralized with 1M aqueous HCl, and extracted thoroughly with ethyl acetate containing 5% (v/v) methanol. The organic layers are dried over $MgSO_4$ and chromatographed on silica gel to afford the corresponding taurocholate conjugates. These sulfonic acids are converted to the corresponding sodium salts by dissolving each compound in 50% $MeOH/H_2O$ (5 mL) and stirring with $Na^+$ cation exchange resin (prepared from Dowex HCR-W2, ~4 mmol) for 30 min. The resins are washed with 50% $MeOH/H_2O$ (3×5 mL) and the combined filtrates evaporated to dryness to afford (112) and (113).

Example 23
Synthesis of Compounds (114) and (115)

To a solution of (105) (1 mmol) in dry THF (10 mL) is added triethylamine (1.1 mmol) followed by 2,4,6-trichlorobenzoylchloride (1.1 mmol). After 10 min a solution of either (96) or (97) (1 mmol each) in dry THF (5 mL) is added followed by DMAP (0.5 mmol). The mixtures are stirred at room temperature for 18 h then washed with saturated $NaHCO_3$ (10 mL) and saturated aqueous citric acid (3×10 mL). The organic layers are dried over $MgSO_4$, the solvent removed in vacuo and the residues purified by flash chromatography on silica gel to give respectively the 3α- and 3β-glycocholate tert-butyl ester derivatives. These compounds are treated with 50% (v/v) TFA in $CH_2Cl_2$ for 30 min and the solvent removed in vacuo. The acids are converted to the corresponding sodium salts by dissolving each compound in 50% $MeOH/H_2O$ (5 mL) and stirring with $Na^+$ cation exchange resin (prepared from Dowex HCR-W2, ~4 mmol) for 30 min. The resins are washed with 50% $MeOH/H_2O$ (3×5 mL) and the combined filtrates evaporated to dryness to afford (114) and (115).

Example 24
Synthesis of Compound (116)

CBz-phenylalanine (2 mmol) is dissolved in anhydrous dioxane (10 mL) and tributylamine (2.5 mmol) added slowly with stirring. The solution is cooled to −5° C. in an ice-salt bath, and ethyl chloroformate (2.5 mmol) added slowly, maintaining the temperature between −5 to 0° C. After addition is complete, the cold mixture is stirred for an additional 15 minutes. A solution containing gabapentin (2) (3 mmol) in 2N NaOH (2 mL) is added and the mixture stirred for an additional 60 min at 0° C. After removal of the dioxane in vacuo, saturated $NaHCO_3$ (15 mL) is added and the aqueous mixture washed with EtOAc (3×10 mL), then the pH adjusted to 3–4 with citric acid. The product is extracted into EtOAc (3×15 mL), and the combined organic phases dried over $MgSO_4$, and concentrated to dryness. Purification by flash chromatography on silica gel afforded peptide (116).

Example 25
Synthesis of Compounds (119) and (120)

To a solution of (116) (1 mmol) in dry THF (10 mL) is added triethylamine (1.1 mmol) followed by 2,4,6-trichlorobenzoylchloride (1.1 mmol). After 10 min a solution of either (92) or (93) (1 mmol each) in dry THF (5 mL) is added followed by DMAP (0.5 mmol). The mixture is stirred at room temperature for 18 h. The reaction mixture is washed with saturated $NaHCO_3$ (10 mL) then saturated aqueous citric acid (3×10 mL). The organic phase is dried over $MgSO_4$, the solvent removed in vacuo and the residue purified by flash chromatography on silica gel to give respectively the 3α- and 3β-tert-butyl cholate derivatives. These are treated with 50% (v/v) TFA in $CH_2Cl_2$ for 30 min and the solvent removed in vacuo to afford (117) and (118).

(117) and (118) (1 mmol) are each dissolved in dry dioxane (10 mL) containing tri-n-butylamine (2 mmol), cooled to 0° C., and ethyl chloroformate (1 mmol) added dropwise. After stirring for 20 min a solution of taurine (2 mmol) in 2 M aqueous NaOH (1 mL) is slowly added and the mixtures warmed to room temperature with stirring for 2 h. The mixtures are poured into water (20 mL), neutralized with 1M aqueous HCl, and extracted thoroughly with ethyl acetate containing 5% (v/v) methanol. The organic layers are dried over $MgSO_4$ and chromatographed on silica gel to afford the corresponding taurocholate conjugates. These sulfonic acids are converted to the corresponding sodium salts by dissolving each compound in 50% $MeOH/H_2O$ (5 mL) and stirring with $Na^+$ cation exchange resin (prepared from Dowex HCR-W2, ~4 mmol) for 30 min. The resins are washed with 50% $MeOH/H_2O$ (3×5 mL) and the combined filtrates evaporated to dryness. The salts are each dissolved in 10% aqueous EtOH (5 mL) and stirred with 5% Pd/C (50 mg) under 1 atm hydrogen gas for 2 h, affording the pure Phe-gabapentin conjugates (119) and (120).

Example 26
Synthesis of Compounds (121) and (122)

To a solution of (116) (1 mmol) in dry THF (10 mL) is added triethylamine (1.1 mmol) followed by 2,4,6-trichlorobenzoylchloride (1.1 mmol). After 10 min a solution of either (96) or (97) (1 mmol each) in dry THF (5 mL) is added followed by DMAP (0.5 mmol). The mixtures are stirred at room temperature for 18 h then washed with saturated $NaHCO_3$ (10 mL) and saturated aqueous citric acid (3×10 mL). The organic layers are dried over $MgSO_4$, the solvent removed in vacuo and the residues purified by flash chromatography on silica gel to give respectively the 3α- and 3β-glycocholate tert-butyl ester derivatives. These compounds are treated with 50% (v/v) TFA in $CH_2Cl_2$ for 30 min and the solvent removed in vacuo. The acids are converted to the corresponding sodium salts by dissolving each compound in 50% $MeOH/H_2O$ (5 mL) and stirring with $Na^+$ cation exchange resin (prepared from Dowex HCR-W2, ~4 mmol) for 30 min. The resins are washed with 50% $MeOH/H_2O$ (3×5 mL) and the combined filtrates evaporated to dryness. The salts are each dissolved in 10% aqueous EtOH (5 mL) and stirred with 5% Pd/C (50 mg) under 1 atm hydrogen gas for 2 h, affording the pure Phe-gabapentin conjugates (121) and (122).

Example 27
Synthesis of Compound (124)

To a solution of (108) (216 mg, 1 mmol) in dry $CH_2Cl_2$ (10 mL) was added triethylamine (167 µL, 1.2 mmol) followed by 2,4,6-trichlorobenzoylchloride (187 µL, 1.2 mmol). After 10 min, a solution of (96) (521 mg, 1 mmol) in dry $CH_2Cl_2$ (20 mL) was added dropwise, followed by DMAP (12 mg). The reaction mixture was stirred at room temperature for 18 h, then washed with saturated aqueous $NaHCO_3$ (10 mL) and saturated aqueous citric acid (3×10 mL). The organic phase was dried over $MgSO_4$ and purified by flash chromatography on silica gel ($CH_2Cl_2$—MeOH 97:3) to give compound (123) (345 mg, 48% yield).

MS (ESI): m/z=742.6 ($M+Na^+$). $^1H$ NMR ($CD_3OD$, 400 MHz, characteristic resonances only): 3.91 (s, 2H), 1.44 (s, 9H), 0.97 (d, 3H, J=6.4 Hz), 0.88 (s, 3H), 0.67 (s, 3H).

A mixture of (123) (230 mg, 0.32 mmol) and pyridium p-toluenesulfonate (8 mg, 0.032 mmol) in MeOH (10 mL) was stirred at 55° C. for 4 h. The solvent was removed in vacuo, and the residue purified by chromatography on silica gel to afford the pure alcohol intermediate (173 mg, 85% yield). Electrospray mass spectrometry showed the expected molecular ion at m/z=636.6 ($M+H^+$). A sample of this product (48 mg, 0.075 mmol) was heated under reflux with a toluene solution containing acyl azide (39) (~2.5 mmol) for 14 h. After cooling to room temperature, the solvent was removed in vacuo and the residue dissolved in EtOAc (20 mL), washed with water (2×10 mL) and dried over $MgSO_4$. This tent-butyl ester product (30 mg, 47% yield) was purified using preparative TLC (10% $MeOH/CH_2Cl_2$). Electrospray mass spectrometry showed the expected molecular ion at m/z=847.63 ($M+H^+$). The ester was treated with 50% $TFA/CH_2Cl_2$ for 3 h, the solvent removed in vacuo and the resulting residue stirred for 30 min with 20% piperidine in $CH_2Cl_2$ (10 mL). After removal of the solvent in vacuo, the residue was purified using preparative TLC (10% MeOH/$CH_2Cl_2$) to afford glycocholate derivative (124) (15 mg, 54% yield).

MS (ESI): 791.6 (M+H$^+$). $^1$H NMR (CD$_3$OD, 400 MHz, characteristic resonances only): 3.88 (s, 2H), 3.65 (s, 3H), 3.34 (s, 2H), 2.28 (s, 2H), 1.02 (d, 3H, J=6.4 Hz), 0.91(s, 3H), 0.71 (s, 3H).

Example 28
Synthesis of Compound (125)

(109) (120 mg, 0.26 mmol) was heated under reflux with a toluene solution containing acyl azide (39) (~2.5 mmol) for 14 h. After cooling to room temperature, the solvent was removed in vacuo and the residue dissolved in EtOAc (20 mL), washed with water (2×10 mL) and dried over MgSO$_4$. The cyanoethyl ester product (40 mg, 23% yield) was purified using preparative TLC (10% MeOH/$CH_2Cl_2$). Electrospray mass spectrometry showed the expected molecular ion at m/z=673.5 (M+H$^+$). This material was treated with 20% piperidine/$CH_2Cl_2$ (2 mL) for 30 min and the solvent removed in vacuo. Purification of the resulting residue by preparative TLC (10% MeOH/$CH_2Cl_2$) afforded the gabapentin carbamate conjugate (125) (28 mg, 77% yield). Electrospray mass spectrometry showed the expected molecular ion at m/z=620.6 (M+H$^+$).

Example 29
Synthesis of Compound (126)

(125) (0.5 mmol) is dissolved in dry dioxane (5 ML) containing tri-n-butylamine (1 mmol), cooled to 0° C., and ethyl chloroformate (0.5 mmol) added dropwise. After stirring for 20 min a solution of taurine (1 mmol) in 2 M aqueous NaOH (0.5 mL) is slowly added and the mixture warmed to room temperature with stirring for 2 h. The mixture is poured into water (10 mL), neutralized with 1M aqueous HCl, and extracted thoroughly with ethyl acetate containing 5% (v/v) methanol. The organic layer is dried over MgSO$_4$ and chromatographed on silica gel to afford the corresponding taurocholate conjugate. This sulfonic acid is converted to the corresponding sodium salt by dissolution in 50% MeOH/H$_2$O (2 mL) and stirring with Na$^+$ cation exchange resin (prepared from Dowex HCR-W2, ~2 mmol) for 30 min. The resin is washed with 50% MeOH/H$_2$O (3×2 mL) and the combined filtrates evaporated to dryness to afford compound (126).

Example 30
Synthesis of Compounds (127)–(130)

(102) and (103) (0.5 mmol each) are separately heated under reflux with a toluene solution containing either acyl azide (39) or (43) (~2.5 mmol) for 14 h. After cooling to room temperature, the solvent is removed in vacuo and the four residues dissolved in EtOAc (20 mL), washed with water (2×10 mL) and dried over MgSO$_4$. The products are purified by preparative TLC on silica gel plates. The two cyanoethyl ester products are deprotected by treatment with 20% piperidine/$CH_2Cl_2$ (2 mL) for 30 min and the solvent removed in vacuo. The four tert-butyl esters are treated with 50% (v/v) TFA in $CH_2Cl_2$ for 30 min and the solvent removed in vacuo. The acids are converted to the corresponding sodium salts by dissolving each compound in 50% MeOH/H$_2$O (5 mL) and stirring with Na$^+$ cation exchange resin (prepared from Dowex HCR-W2, ~2 mmol) for 30 min. The resins are washed with 50% MeOH/H$_2$O (3×5 mL) and the combined filtrates evaporated to dryness to afford compounds (127)–(130).

Example 31
Synthesis of Compounds (139)–(146)

Compounds (131)–(134) are prepared from compounds (96)–(99) respectively following the method of Batta et al (*J. Lipid Res.* 1991, 32, 977–983). The starting steroids (5 mmol) are heated under reflux in a mixture of carbon tetrachloride (10 mL) and pyridine (10 mL) with succinic anhydride (5 mmol) for 3 h. The solvent is removed in vacuo and the residues taken up in ethyl acetate, washed with 0.2 M aqueous KHSO$_4$, dried over MgSO$_4$ then chromatographed on silica gel to give the hemisuccinate products (131)–(134).

These acids (2 mmol each) are separately dissolved in anhydrous dioxane (20 mL) and tributylamine (2.2 mmol) added slowly with stirring. The solutions are cooled to –5° C. in an ice-salt bath, and ethyl chloroformate (2.2 mmol) added slowly, maintaining the temperature between –5 to 0° C. After addition is complete, the cold mixtures are stirred for an additional 15 minutes. A solution containing gabapentin (2) (3 mmol) in 2N NaOH (3 mL) is added and the mixtures stirred for an additional 60 min at –5 to 0° C. After removal of the dioxane in vacuo, saturated NaHCO$_3$ (20 mL) is added and the aqueous mixtures washed with EtOAc (3×10 mL), then the pH adjusted to 3–4 with citric acid. The products are extracted into EtOAc (3×20 mL), and the combined organic phases dried over MgSO$_4$, and concentrated to dryness. The residues are purified by flash chromatography on silica gel to give the gabapentin acid conjugates acids (135)–(138).

These acids (135)–(138) (0.5 mmol each) are separately dissolved in methanol (10 mL) and a freshly prepared solutions of diazomethane in diethyl ether added until a pale yellow color persists. After stirring for 60 min, the solvent is removed in vacuo to afford the corresponding methyl ester derivatives.

The tert-butyl ester moieties in acids (135)–(138) and their corresponding methyl ester analogs (0.5 mmol each) are transformed to the corresponding sodium salts (139)–(146) by first treating with 50% (v/v) TFA in $CH_2Cl_2$ (5 mL) for 30 min, purification of the resulting acids by flash chromatography on silica gel, and finally stirring each compound in 50% MeOH/H$_2$O (5 mL) with Na$^+$ cation exchange resin (prepared from Dowex HCR-W2, ~2 mmol) for 30 min.

Example 32
Synthesis of Compounds (143)–(158)

A suspension of mercuric oxide (1 mmol) and each of (131)–(134) (2 mmol) in $CH_2Cl_2$ (15 mL) are separately stirred overnight at room temperature. 2 mmol of either (56) or (57) is added to these suspensions and stirring continued for 24 h. The eight solutions are washed with saturated NaHCO$_3$, water and brine and the organic phase evaporated to dryness. The residues are purified by flash chromatography on silica gel to afford carbonates (135)–(142).

(135)–(142) (1 mmol each) are dissolved in dioxane (10 mL) and a solution of gabapentin (2) (1 mmol) in aqueous phosphate buffer at pH ~8.5 (1 mL) added to each with vigorous stirring. After 2 h, the solvent is removed in vacuo, the residues treated with aqueous citric acid (pH 3–4) and extracted with EtOAc (3×10 mL). The combined organic phases are dried over MgSO$_4$, concentrated to ~5 mL and purified by flash chromatography on silica gel to afford the corresponding gabapentin acid adducts. Each adduct is divided into two equal portions, one of which is dissolved in methanol (5 mL) and stirred with excess of a freshly prepared solution of diazomethane in diethyl ether. After stirring for 60 min, the solvent is removed in vacuo to afford the methyl ester analogs. These esters along with the remaining portions of their acid precursors are separately treated with 50% (v/v) TFA in $CH_2Cl_2$ for 30 min and the solvent removed in vacuo. The products are converted to the corresponding sodium salts by dissolving each residue in 50% MeOH/$H_2O$ (5 mL) and stirring with $Na^+$ cation exchange resin (prepared from Dowex HCR-W2, ~4 mmol) for 30 min. The resins are washed with 50% MeOH/$H_2O$ (3×5 mL) and the combined filtrates evaporated to dryness to afford compounds (143)–(158).

Example 33
Synthesis of Compounds (163)–(166)

Four solutions containing Fmoc-phenylalanine (1 mmol) and one of compounds (96)–(99) (1 mmol each) in dry DMF (4 mL) are treated with diisopropylcarbodiimide (DIC) (1 mmol) for 4 h at room temperature. After filtering the solutions, the solvent is removed in vacuo, the residues redissolved in ethyl acetate and washed thoroughly with 0.2 M aqueous solutions of $KHSO_4$. The organic layers are dried over $MgSO_4$ and chromatographed on silica gel to afford compounds (159)–(162).

Each product is stirred for 30 min in a 20% (v/v) solution of piperidine in DMF (5 mL) and the solvent removed in vacuo. To each residue is added a solution containing (104) (1.2 mmol) and DIC (1.2 mmol) in DMF (5 mL) and the mixtures stirred at room temperature for 2 h. After filtering the solutions, the solvent is removed in vacuo, the residues are redissolved in ethyl acetate and washed thoroughly with saturated aqueous $NaHCO_3$. The organic layers are dried over $MgSO_4$ and chromatographed on silica gel to afford the protected gabapentin peptidyl glycocholates. These products are separately treated with 50% (v/v) TFA in $CH_2Cl_2$ for 30 min and the solvent removed in vacuo to afford compounds (163)–(166).

Example 34
Synthesis of Compound (167)

Compound (116) (1 mmol) dissolved in EtOH (20 mL) is stirred with 5% Pd/C (100 mg) under 1 atm hydrogen gas for 2 h and the solvent removed in vacuo to afford compound (167) in quantitative yield.

Example 35
Synthesis of Compounds (168)–(175)

Solutions of compounds (96)–(99) (1 mmol each) in dry $CH_2Cl_2$ (10 mL) and pyridine (1 mL) are cooled to 0° C. and separately treated with 4-nitrophenyl chloroformate (1 mmol) with stirring for 2 h. The solutions are washed with saturated $NaHCO_3$, water and brine and the organic layers evaporated to dryness. The residues are purified by flash chromatography on silica gel to afford the intermediate 4-nitrophenyl carbonates or carbamates. Each product is separately dissolved in dioxane (5 mL) and a solution of (167) (1 mmol) in aqueous phosphate buffer at pH ~8.5 (1 mL) added to each with vigorous stirring. After 2 h, the solvent is removed in vacuo, the residues treated with aqueous citric acid (pH 3–4) and extracted with EtOAc (3×10 mL). The combined organic phases are dried over $MgSO_4$, concentrated to ~5 mL and purified by flash chromatography on silica gel to afford the corresponding gabapentin acid adducts. Each adduct is divided into two equal portions, one of which is dissolved in methanol (5 mL) and stirred with excess of a freshly prepared solution of diazomethane in diethyl ether. After stirring for 60 min, the solvent is removed in vacuo to afford the methyl ester analogs. These esters along with the remaining portions of their acid precursors are separately treated with 50% (v/v) TFA in $CH_2Cl_2$ for 30 min and the solvent removed in vacuo. The products are converted to the corresponding sodium salts by dissolving each residue in 50% MeOH/$H_2O$ (5 mL) and stirring with $Na^+$ cation exchange resin (prepared from Dowex HCR-W2, ~2 mmol) for 30 min. The resins are washed with 50% MeOH/$H_2O$ (3×5 mL) and the combined filtrates evaporated to dryness to afford compounds (168)–(175).

Example 36
Synthesis of Compounds (196)–(211)

Compounds (96)–(99) (3 mmol each) are separately dissolved in dry acetonitrile (15 mL) together with DMAP (3 mmol). Solutions of bromoacetic anhydride (3.5 mmol) in acetonitrile are added dropwise and the reaction mixtures stirred for 4 h at room temperature. The solvent is removed in vacuo, the residues redissolved in ethyl acetate and washed thoroughly with a 0.2 M aqueous solution of $KHSO_4$. The organic phases are dried over $MgSO_4$ and evaporated to dryness to afford the crude bromoacetates (176) and (177), and bromoacetamides (178) and (179), which are used as is in subsequent steps.

Solutions containing either 2 M ethylamine or benzylamine in dry DMSO (1 mL) are added separately to solutions of the bromoacetyl compounds (176)–(179) (2 mmol) in dry DMSO (4 mL). After stirring at room temperature for 4 h, the solvent is removed in vacuo. The residues are redissolved in ethyl acetate and washed with saturated $NaHCO_3$, water and brine, then the organic layers evaporated to dryness. The resulting amine compounds (180)–(187) are used in the subsequent step without further purification.

Solutions containing O-trimethylsilyl-glycolic acid (1.1 mmol) and DIC (1.1 mmol) in DMF (1 mL) are separately added to solutions of compounds (180)–(187) (1 mmol each) in DMF (4 mL). After stirring for 2 h at room temperature, the solutions are filtered and the solvent removed in vacuo. The residues are redissolved in ethyl acetate, washed thoroughly with 0.2 M aqueous $KHSO_4$, and the organic layers dried over $MgSO_4$ and evaporated to dryness. The resulting O-silyl-glycolamides are each dissolved in $CH_2Cl_2$ containing pyridine-HF complex (1.5 mmol) and the mixtures stirred for 2 h at room temperature. After removal of the solvent in vacuo, the residues are purified by flash chromatography on silica gel to afford glycolamides (188)–(195).

(188)–(195) (0.5 mmol each) are separately heated under reflux with a toluene solution containing either acyl azide (39) or (43) (~2.5 mmol) for 14 h. After cooling to room temperature, the solvent is removed in vacuo and the sixteen residues dissolved in EtOAc (20 mL), washed with water (2×10 mL) and dried over $MgSO_4$. The products are purified by preparative TLC on silica gel plates. The eight cyanoethyl ester products are deprotected by treatment with 20% piperidine/$CH_2Cl_2$ (2 mL) for 30 min and the solvent removed in vacuo. The sixteen tert-butyl esters are treated with 50% (v/v) TFA in $CH_2Cl_2$ for 30 min and the solvent removed in vacuo. The acids are converted to the corresponding sodium salts by dissolving each compound in 50% MeOH/$H_2O$ (5 mL) and stirring with $Na^+$ cation exchange resin (prepared from Dowex HCR-W2, ~2 mmol) for 30 min. The resins are washed with 50% MeOH/$H_2O$ (3×5 mL) and the combined filtrates evaporated to dryness to afford compounds (196)–(211).

Example 37
Synthesis of Compounds (221)–(228)

Solutions of compounds (96) and (97) (2 mmol each) in dry $CH_2Cl_2$ (20 mL) and pyridine (2 mL) are cooled to 0°

C. and separately treated with 4-nitrophenyl chloroformate (2 mmol) with stirring for 2 h. The solutions are washed with saturated NaHCO$_3$, water and brine and the organic layers evaporated to dryness. The residues are purified by flash chromatography on silica gel to afford the intermediate 4-nitrophenyl carbonates. Each product is separately dissolved in dioxane (10 mL) and a solution of GABA (2 mmol) in aqueous phosphate buffer at pH ~8.5 (2 mL) added to each with vigorous stirring. After 2 h, the solvent is removed in vacuo, the residues treated with aqueous citric acid (pH 3–4) and extracted with EtOAc (3×15 mL). The combined organic phases are dried over MgSO$_4$, concentrated to ~5 L and purified by flash chromatography on silica gel to afford the corresponding acids (215) and (216).

A suspension of mercuric oxide (1 mmol) and each of (215) and (216) (2 mmol) in CH$_2$Cl$_2$ (15 mL) are separately stirred overnight at room temperature. 2 mmol of either (56) or (57) is added to these suspensions and stirring continued for 24 h. The four solutions are washed with saturated NaHCO$_3$, water and brine and the organic layers evaporated to dryness. The residues are purified by flash chromatography on silica gel to afford carbonates (217)–(220).

(217)–(220) (1 mmol each) are dissolved in dioxane (10 mL) and a solution of gabapentin (2) (1 mmol) in aqueous phosphate buffer at pH ~8.5 (1 mL) added to each with vigorous stirring. After 2 h, the solvent is removed in vacuo, the residues treated with aqueous citric acid (pH 3–4) and extracted with EtOAc (3×10 mL). The combined organic phases are dried over MgSO$_4$, concentrated to ~5 mL and purified by flash chromatography on silica gel to afford the corresponding gabapentin acid adducts. Each adduct is divided into two equal portions, one of which is dissolved in methanol (5 mL) and stirred with excess of a freshly prepared solution of diazomethane in diethyl ether. After stirring for 60 min, the solvent is removed in vacuo to afford the corresponding methyl ester analogs. These esters along with the remaining portions of their acid precursors are separately treated with 50% (v/v) TFA in CH$_2$Cl$_2$ for 30 min and the solvent removed in vacuo. The products are converted to the corresponding sodium salts by dissolving each residue in 50% MeOH/H$_2$O (5 mL) and stirring with Na$^+$ cation exchange resin (prepared from Dowex HCR-W2, ~2 mmol) for 30 min. The resins are washed with 50% MeOH/H$_2$O (3×5 mL) and the combined filtrates evaporated to dryness to afford compounds (221)–(228).

Example 38
Synthesis of Compound (230)

Cholic acid (6) (2 g, 4.9 mmol) was dissolved in anhydrous acetone (50 mL) and tert-butyl bromoacetate (0.87 mL, 5.9 mmol) and powdered K$_2$CO$_3$ (1.4 g, 9.8 mmol) added. The solution was heated under reflux overnight and then cooled to room temperature. The mixture was filtered and the filtrate concentrated to a small volume. The protected glycolate product (229) was isolated as a white solid after purification by flash chromatography on silica gel, eluting with CH$_2$Cl$_2$/MeOH (95/5). Compound (229) (160 mg, 0.26 mmol) was dissolved in 60% (v/v) TFA/CH$_2$Cl$_2$ and stirred for 2 h at room temperature. After removal of the solvent in vacuo the residue was treated with water and extracted with ethyl acetate. The organic layer was dried and concentrated in vacuo. This residue was treated with 25% (v/v) piperidine/CH$_2$Cl$_2$ for 1 h to saponify any trifluoroacetate ester formed during the TFA deprotection step. After removal of the piperidine/CH$_2$Cl$_2$ in vacuo, the product was extracted with ethyl acetate, washed with aqueous citric acid solution, dried over MgSO$_4$ and concentrated in vacuo. This crude acid product was dissolved in dry THF (10 mL), NEt$_3$ (47 µL, 0.34 mmol) added and the solution cooled to –5° C. in an ice-salt bath. Ethyl chloroformate (19 µL, 0.2 mmol) was added slowly, maintaining the temperature between –5 to 0° C. After addition was completed, the cold mixture was stirred for an additional 30 minutes. A solution containing gabapentin (2) (57 mg, 0.34 mmol) and NaHCO$_3$ (28 mg, 0.34 mmol) in water (1 mL) was added to this mixture and stirred at for 30 minutes at 0° C. and then at room temperature for an additional 30 minutes. The pH of the solution was adjusted to 3–4 by addition of citric acid and the mixture extracted with ethyl acetate (2×20 mL). The organic layer was dried over MgSO$_4$ and concentrated in vacuo. The product (230) (50 mg, 50% yield) was isolated after purification by flash chromatography on silica gel, eluting with EtOAc/MeOH (90/10).

MS (ESI): m/z=620.5 (M+H$^+$). $^1$H NMR (CD$_3$OD, 400 MHz, characteristic resonances only): 4.55 (s, 2H), 3.34 (s, 2H), 2.29 (s, 2H), 1.02 (d, 3H, J=6.4 Hz), 0.91 (s, 3H), 0.71(s, 3H).

Example 39
Synthesis of Compound (232)

Cholic acid (6) (490 mg, 1.2 mmol) and NEt$_3$ (145 µL, 2 mmol) were dissolved in dry THF (20 mL) and trichlorobenzoyl chloride (292 mg, 1.2 mmol) added. After stirring for 30 minutes tert-butyl (R)-lactate (150 mg, 1 mmol) was added followed by catalytic DMAP (20 mg). The reaction mixture was stirred for 16 h at room temperature and the solvent removed in vacuo. The residue was treated with aqueous citric acid and extracted into ethyl acetate. The organic phase was dried over MgSO$_4$ and concentrated in vacuo. The protected lactate product (231) (450 mg, 84% yield) was purified by flash chromatography on silica gel, eluting with EtOAc/MeOH (97/3). Compound (231) was dissolved in 40% (v/v) TFA/CH$_2$Cl$_2$ and stirred for 2 h at room temperature. After removal of the solvent in vacuo the residue was treated with water and extracted with ethyl acetate. The organic layer was dried and concentrated in vacuo. This residue was treated for 1 h with 25% (v/v) piperidine/CH$_2$Cl$_2$ to saponify any trifluoroacetate ester formed during the TFA deprotection step. After removal of the piperidine/CH$_2$Cl$_2$ in vacuo, the lactic acid conjugate was extracted with ethyl acetate, washed with aqueous citric acid solution, dried over MgSO$_4$ and concentrated in vacuo. To 590 mg of this product (1.2 mmol) was added dry THF (20 mL), NEt$_3$ (335 µL, 2.4 mmol) and the solution cooled to –5° C. in an ice-salt bath. Ethyl chloroformate (140 µL, 1.5 mmol) was added slowly, maintaining the temperature between –5 to 0° C. After addition was completed, the cold mixture was stirred for an additional 30 minutes. A solution containing gabapentin (2) (412 mg, 2.4 mmol) and NaHCO$_3$ (336 mg, 4 mmol) in water (5 mL) was added to this mixture and stirred at for 30 minutes at 0° C. and then at room temperature for an additional 30 minutes. The pH of the solution was adjusted to 3–4 by addition of citric acid and the mixture extracted with ethyl acetate (3×30 mL). The organic layer was dried over MgSO$_4$ and concentrated in vacuo. The product (232) (250 mg, 32% yield) was isolated after purification by flash chromatography on silica gel, eluting with EtOAc/MeOH (97/3).

MS (ESI): m/z=634.5 (M+H$^+$). $^1$H NMR (CD$_3$OD, 400 MHz, characteristic resonances only): 5.03 (q, 1H, J=6.8 Hz), 3.34 (s, 2H), 2.29 (s, 2H), 1.42 (d, 3H, 3=6.8 Hz), 101 (d, 3H, J=6.4 Hz), 0.91 (s, 3H), 0.71(s, 3H).

Example 40
Synthesis of Compound (234)

Cholic acid (6) (490 mg, 1.2 mmol) and NEt$_3$ (145 µL, 2 mmol) were dissolved in dry THF (20 mL) and trichlorobenzoyl chloride (292 mg, 1.2 mmol) added. After stirring for 30 minutes benzyl (S)-lactate (180 mg, 1 mmol) was added followed by catalytic DMAP (20 mg). The reaction mixture was stirred for 16 h at room temperature and the solvent removed in vacuo. The residue was treated with aqueous citric acid and extracted into ethyl acetate. The organic phase was dried over $MgSO_4$ and concentrated in vacuo. The protected lactate product (233) was purified by flash chromatography on silica gel, eluting with EtOAc/MeOH (97/3). Compound (233) (480 mg, 1 mmol) was dissolved in EtOAc (30 mL) and stirred with 5% Pd/C (50 mg) under 1 atm hydrogen gas for 6 h to remove the benzyl protecting group. After removal of the solvent in vacuo the residue was dissolved in dry THF (20 mL), $NEt_3$ (335 µL, 2.4 mmol) was added and the solution cooled to −5° C. in an ice-salt bath. Ethyl chloroformate (140 µL, 1.5 mmol) was added slowly, maintaining the temperature between −5 to 0° C. After addition was completed, the cold mixture was stirred for an additional 30 minutes. A solution containing gabapentin (2) (412 mg, 2.4 mmol) and $NaHCO_3$ (336 mg, 4 mmol) in water (5 mL) was added to this mixture and stirred at for 30 minutes at 0° C. and then at room temperature for an additional 30 minutes. The pH of the solution was adjusted to 3–4 by addition of citric acid and the mixture extracted with ethyl acetate (3×30 mL). The organic layer was dried over $MgSO_4$ and concentrated in vacuo. The product (234) was isolated after purification by flash chromatography on silica gel, eluting with EtOAc/MeOH (97/3).

MS (ESI): m/z=634.5 $(M+H^+)$. $^1H$ NMR ($CD_3OD$, 400 MHz, characteristic resonances only): 5.03 (q, 1H, J=6.8 Hz), 3.34 (s, 2H), 2.29 (s, 2H), 1.43 (d, 3H, J=6.8 Hz), 1.01 (d, 3H, J=6.4 Hz), 0.91(s, 3H), 0.71 (s, 3H).

Example 41

Synthesis of Compound (237)

Ursodeoxycholic acid (235) (825 mg, 2.1 mmol) and $NEt_3$ (1.1 mL, 8 mmol) were dissolved in dry THF (35 mL) and the solution cooled to −5° C. in an ice-salt bath. Ethyl chloroformate (242 µL, 2.5 mmol) was added slowly, maintaining the temperature between −5 to 0° C. After addition was completed, the cold mixture was stirred for an additional 30 minutes. A solution of HOBt (378 mg, 2.8 mmol) in dry THF (5 mL) was added and the solution stirred for 30 minutes at 0° C. A solution of gabapentin (2) (684 mg, 4 mmol) in 2N NaOH (5 mL) was added to this mixture and stirred at for 30 minutes at 0° C. and then at room temperature for an additional 30 minutes. The pH of the solution was adjusted to 3–4 by addition of citric acid and the mixture extracted with ethyl acetate (3×50 mL). The organic layer was dried over $MgSO_4$ and concentrated in vacuo. The product (236) (280 mg, 25% yield) was isolated after purification by preparative HPLC, using a Waters Nova-Pak C-18 column (19×300 mm) and eluting with a water/acetonitrile/0.05% formic acid gradient at 25 mL/min (30% MeCN ramping to 43% in 3 min, then to 53% MeCN by 22 min). Electrospray mass spectrometry showed the expected molecular ion at m/z=???$(M+H^+)$. The corresponding sodium salt (237) was prepared in quantitative yield by stirring (236) with 1 equivalent aqueous $NaHCO_3$ and lyophilization to dryness.

MS (ESI): m/z=546.49 $(M+H^+)$ and 544.54 $(M-H^-)$. $^1H$ NMR ($CD_3OD$, 400 MHz, characteristic resonances only): 3.30 (s, 2H), 2.29 (s, 2H), 0.98 (d, 3H, J=6.4 Hz), 0.96 (s, 3H), 0.70 (s, 3H).

Example 42

In Vitro Compound Transport Assays with IBAT and LBAT-Expressing Cell Lines (a) Inhibition of Radiolabeled Taurocholate Uptake CHO cells transfected with either the IBAT or LBAT transporter were seeded into 96-well microtiter plates at 100,000 cells/well in 100 µL DMEM containing 10% serum, glutamine and Penstrep. After overnight incubation the media was removed and test compound (25 µL) added at 2× the final desired concentration. Tritiated taurocholate (50,000 CPM/well) was diluted with cold substrate to a final concentration of 5 µM and 25 µL/well of this mixture was added to the plate. After incubating for 1 h at room temperature the solution was removed and the plate washed 4× with PBS at 4° C. 200 µL/well of scintillant is added and the plate then read in a Wallac microbeta counter. The inhibition data is processed by standard methods to calculate an inhibition constant $K_i$ for the test compound.

(b) Analysis of Electrogenic Transport in *Xenopus* Oocytes RNA Preparation:

Human IBAT and LBAT Transporter cDNAs were subcloned into a modified pGEM plasmid that contains 5' and 3' untranslated sequences from the *Xenopus* β-actin gene. These sequences increase RNA stability and protein expression. Plasmid cDNA was linearized and used as template for in vitro transcription (Epicentre Technologies transcription kit, 4:1 methylated:non-methylated GTP).

*Xenopus* oocyte isolation. *Xenopus laevis* frogs were anesthetized by immersion in Tricaine (1.5 g/mL in deionized water) for 15 min. Oocytes were removed and digested in frog ringer solution (90 mM NaCl, 2 mM KCl, 1 mM $MgCl_2$, 10 mM NaHEPES, pH 7.45, no $CaCl_2$) with 1 mg/mL collagenase (Worthington Type 3) for 80–100 min with shaking. The oocytes were washed 6 times, and the buffer changed to frog ringer solution containing $CaCl_2$ (1.8 mM). Remaining follicle cells were removed if necessary. Cells were incubated at 16° C., and each oocyte injected with 10–20 µg RNA in 45 µL solution.

Electrophysiology measurements. Transport currents were measured 2–14 days after injection, using a standard two-electrode electrophysiology set-up (Geneclamp 500 amplifier, Digidata 1320/PCLAMP software and ADInstruments hardware and software were used for signal acquisition). Electrodes (2–4 mΩ) were microfabricated using a Sutter Instrument puller and filled with 3M KCl. The bath was directly grounded (transporter currents were less than 0.3 µA). Bath flow was controlled by an automated perfusion system (ALA Scientific Instruments, solenoid valves).

For transporter pharmacology, oocytes were clamped at −60 to −90 mV, and continuous current measurements acquired using PowerLab Software and an ADInstruments digitizer. Current signals were lowpass filtered at 20 Hz and acquired at 4–8 Hz. All bath and drug-containing solutions were frog ringers solution containing $CaCl_2$. Drugs were applied for 10–30 seconds until the induced current reached a new steady-state level, followed by a control solution until baseline currents returned to levels that preceded drug application. The difference current (baseline subtracted from peak current during drug application) reflected the net movement of charge resulting from electrogenic transport and was directly proportional to tranport rate. Recordings were made from a single oocyte for up to 60 min, enabling 30–40 separate compounds to be tested per oocyte. Compound-induced currents were saturable and gave half-maximal values at substrate concentrations comparable to radiolabel competition experiments. To compare results between oocytes expressing different levels of transport activity, a saturating concentration of glycodeoxycholate (100 μM) was used as a common reference to normalize results from test compounds. Using this normalization procedure $V_{max}$ (i.e. maximal induced current) for different compounds at 100 μM tested on different oocytes could be compared.

TABLE 1

In vitro transport data for selected compounds on IBAT-expressing cells

| COMPOUND | $IC_{50}$ (M) | $EC_{50}$ (M) | % Max. (GDC) |
|---|---|---|---|
| (8) | 36 | 70 | 67 |
| (13) | 66 | 22 | 67 |
| (124) | 7 | 58 | 28 |
| (125) | >100 | >100 | 0 |
| (230) | 4 | 30 | 83 |
| (232) | 12 | 25 | 70 |
| (234) | 5.6 | 16 | 76 |
| (237) | ND | 67 | 60 |

$IC_{50}$ data from radiolabeled competition assay in transporter-expressing CHO cells
$EC_{50}$ and % Max data (relative to glycodeoxycholate) from transporter-expressing oocytes
ND-Not determined

TABLE 2

In vitro transport data for selected compounds on LBAT-expressing cells

| COMPOUND | $IC_{50}$ (M) | $EC_{50}$ (M) | % Max. (GDC) |
|---|---|---|---|
| (8) | 8 | 19 | 38 |
| (13) | 64 | ND | 38 |
| (124) | 1.7 | ND | ND |
| (125) | 0.7 | 31 | 140 |
| (230) | 2.3 | ND | ND |
| (232) | 4.1 | ND | ND |
| (234) | 1.6 | ND | ND |

Figure 9:
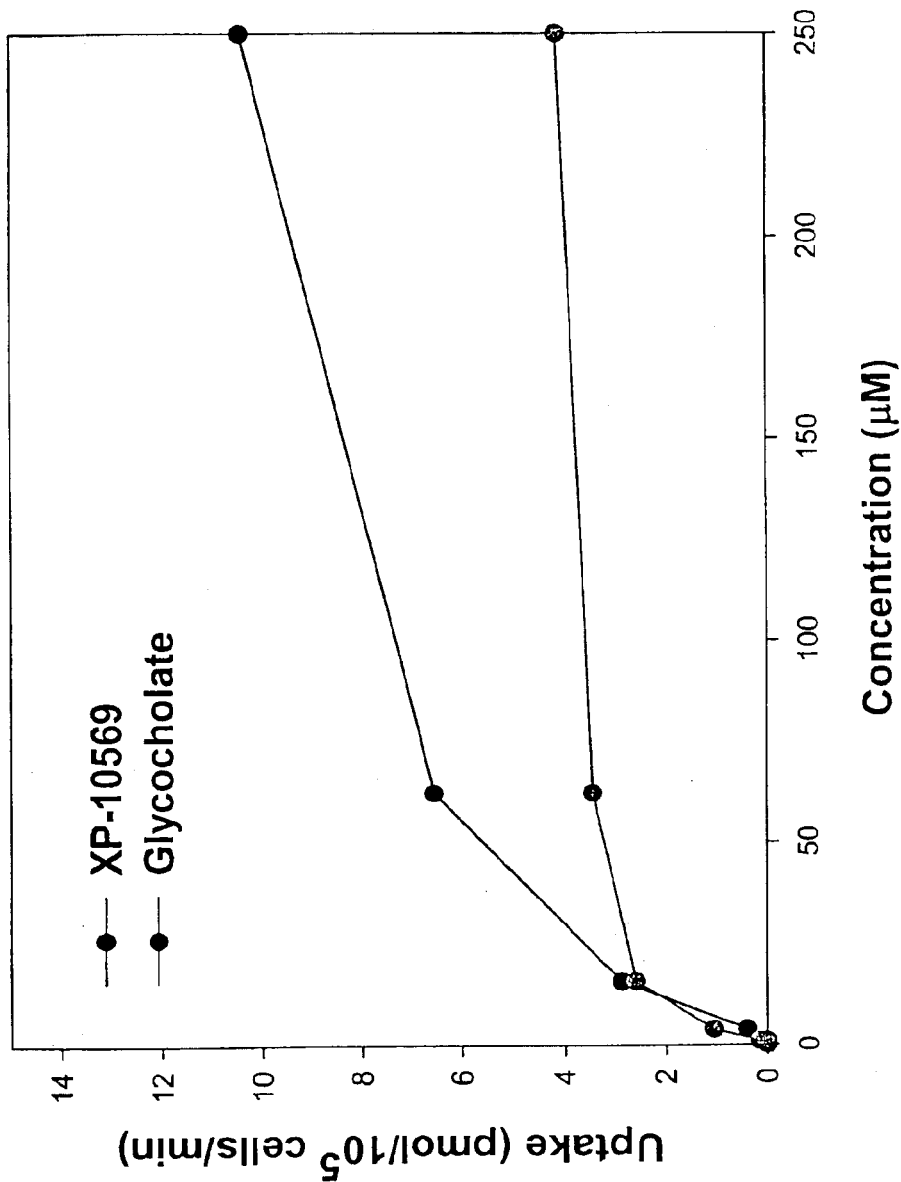
FIG. 9 illustrates the effect of substrate concentration on the active uptake of (8) or glycocholate by IBAT-transfected CHO cells in vitro. Non-specific uptake by untransfected CHO K1 cells has been subtracted.
Figure 10:
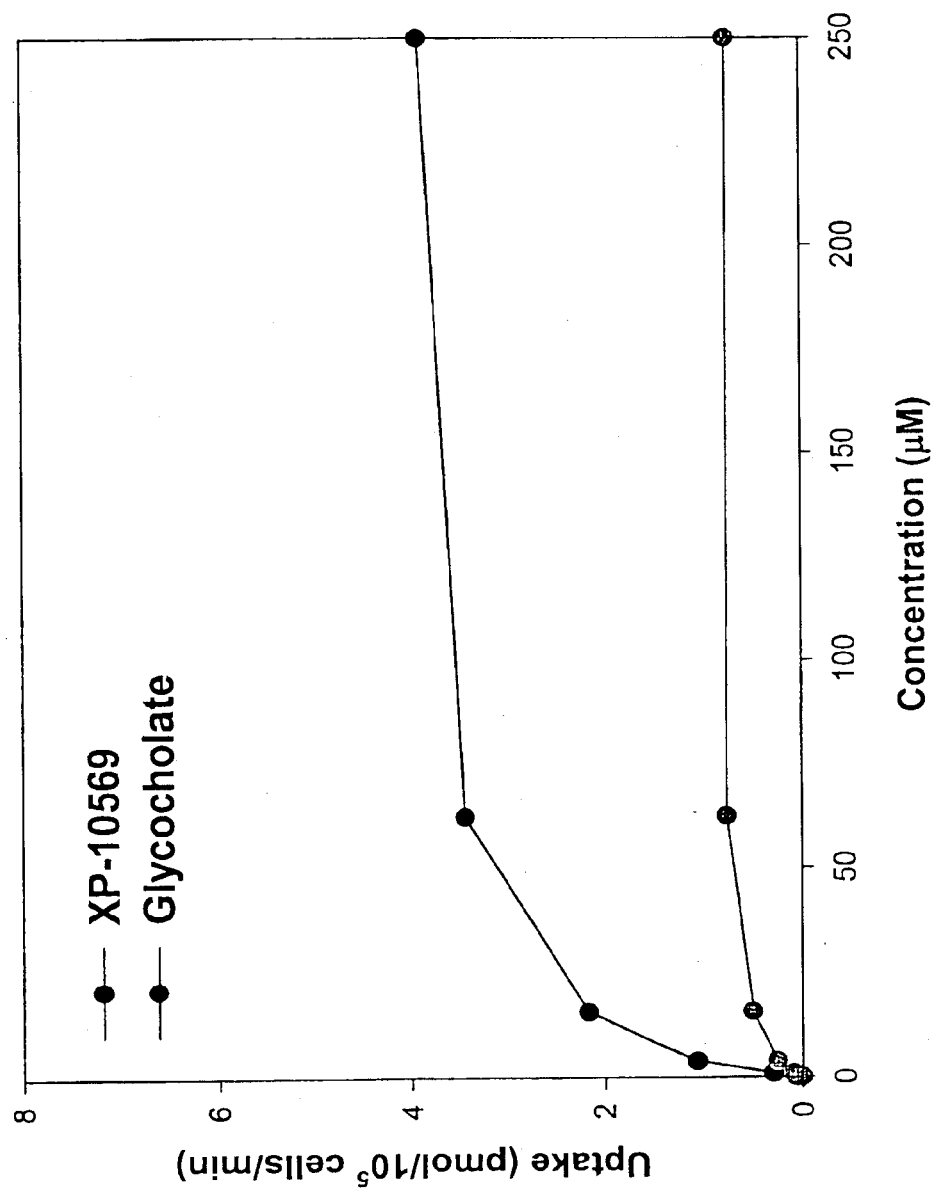
FIG. 10 illustrates the effect of substrate concentration on the active uptake of (8) or glycocholate by LBAT-transfected CHO cells in vitro. Non-specific uptake by untransfected CHO K1 cells has been subtracted.
Figure 11:
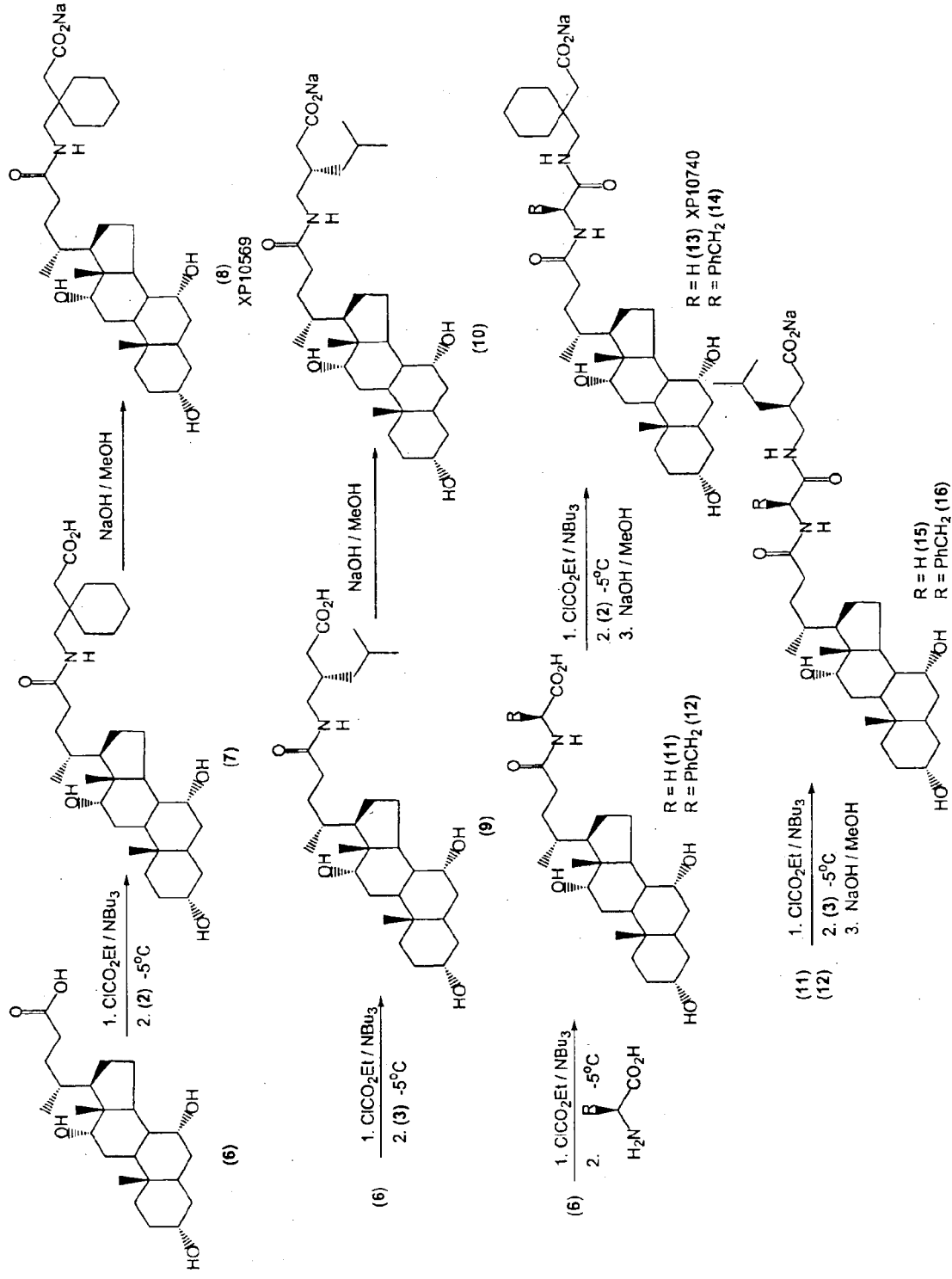
FIGS. 11–33 illustrate reaction sequences for preparation of compounds of formulae (I)–(III).
Figure 12:
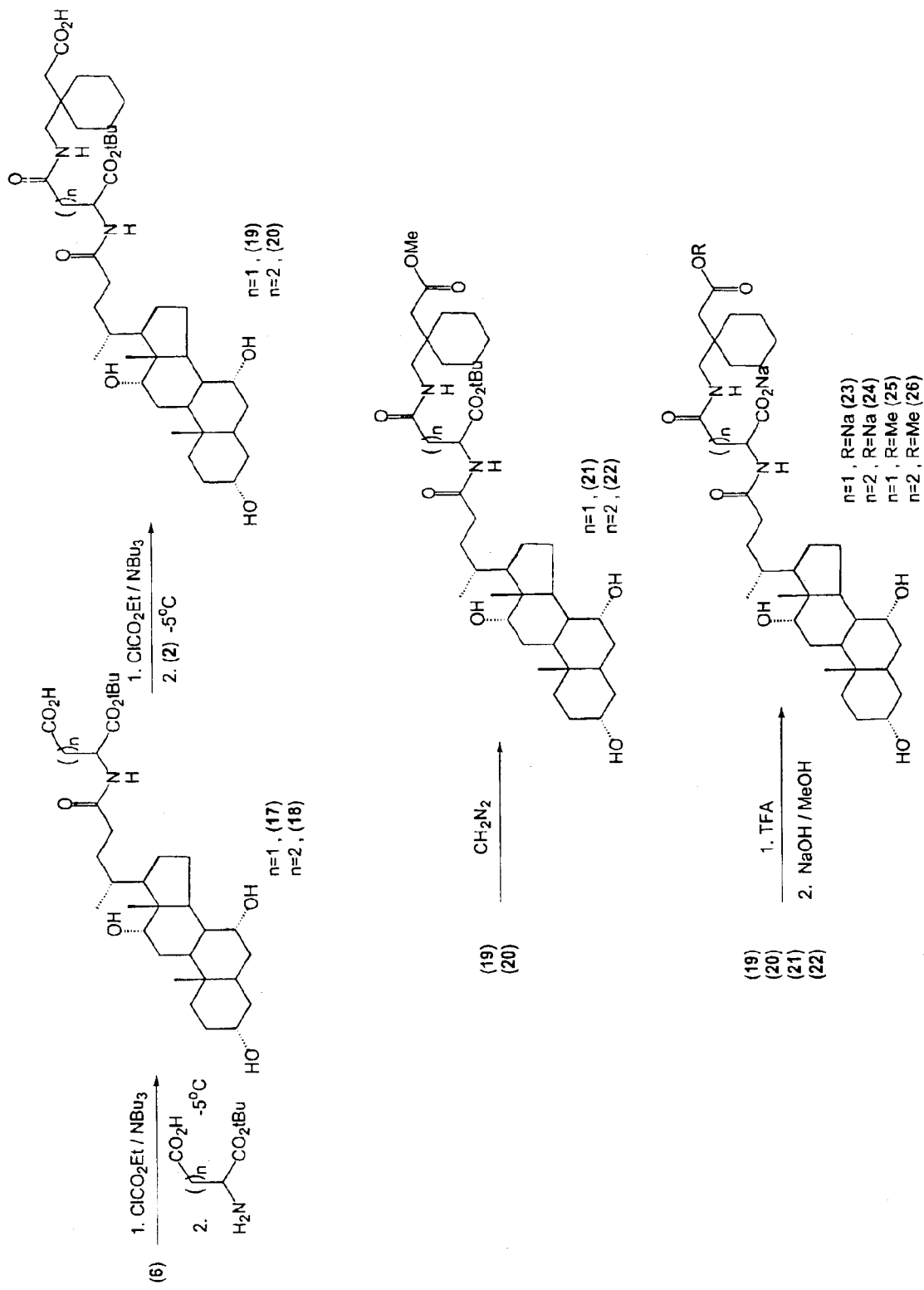
Figure 13:
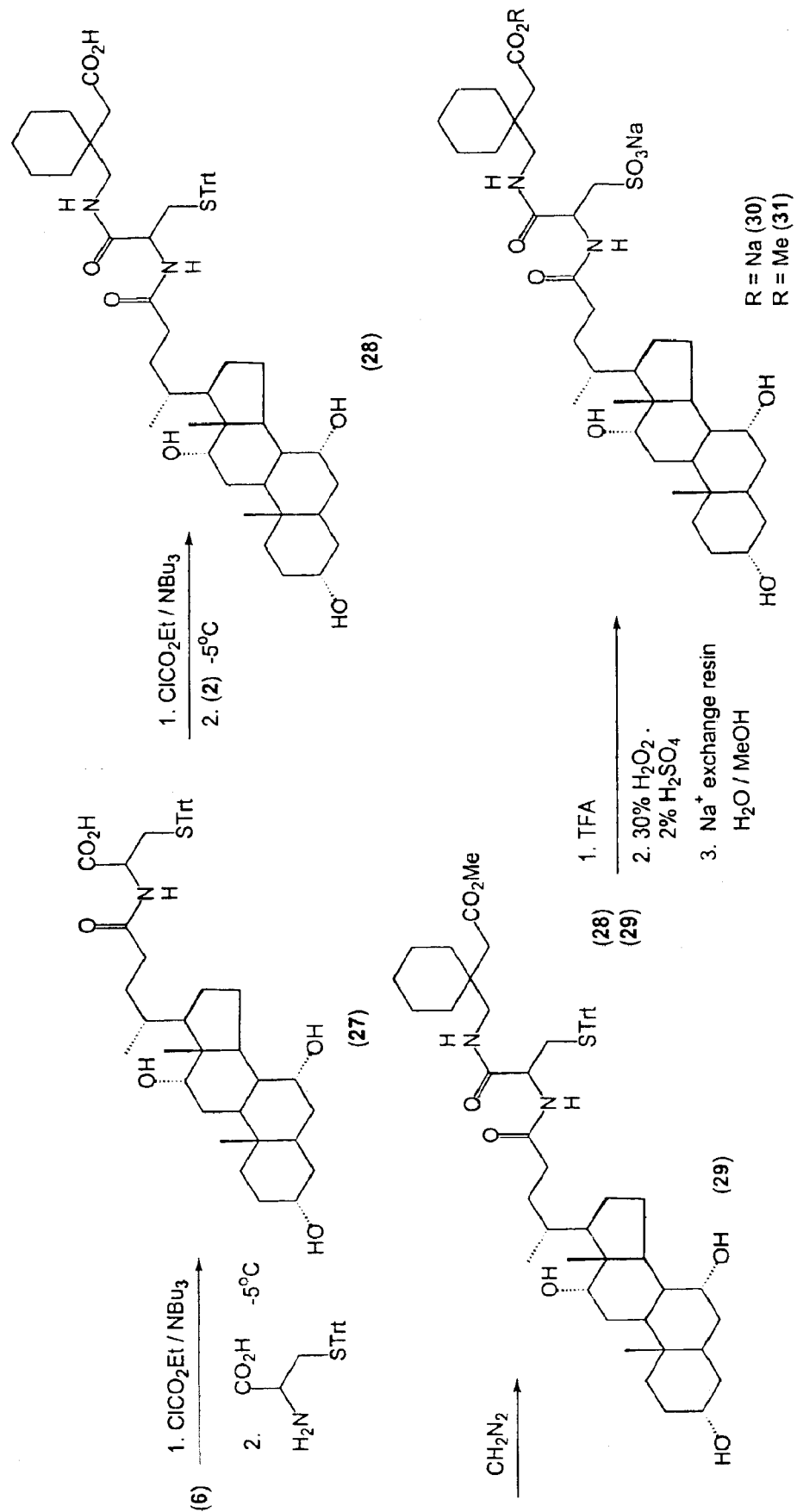
Figure 14:
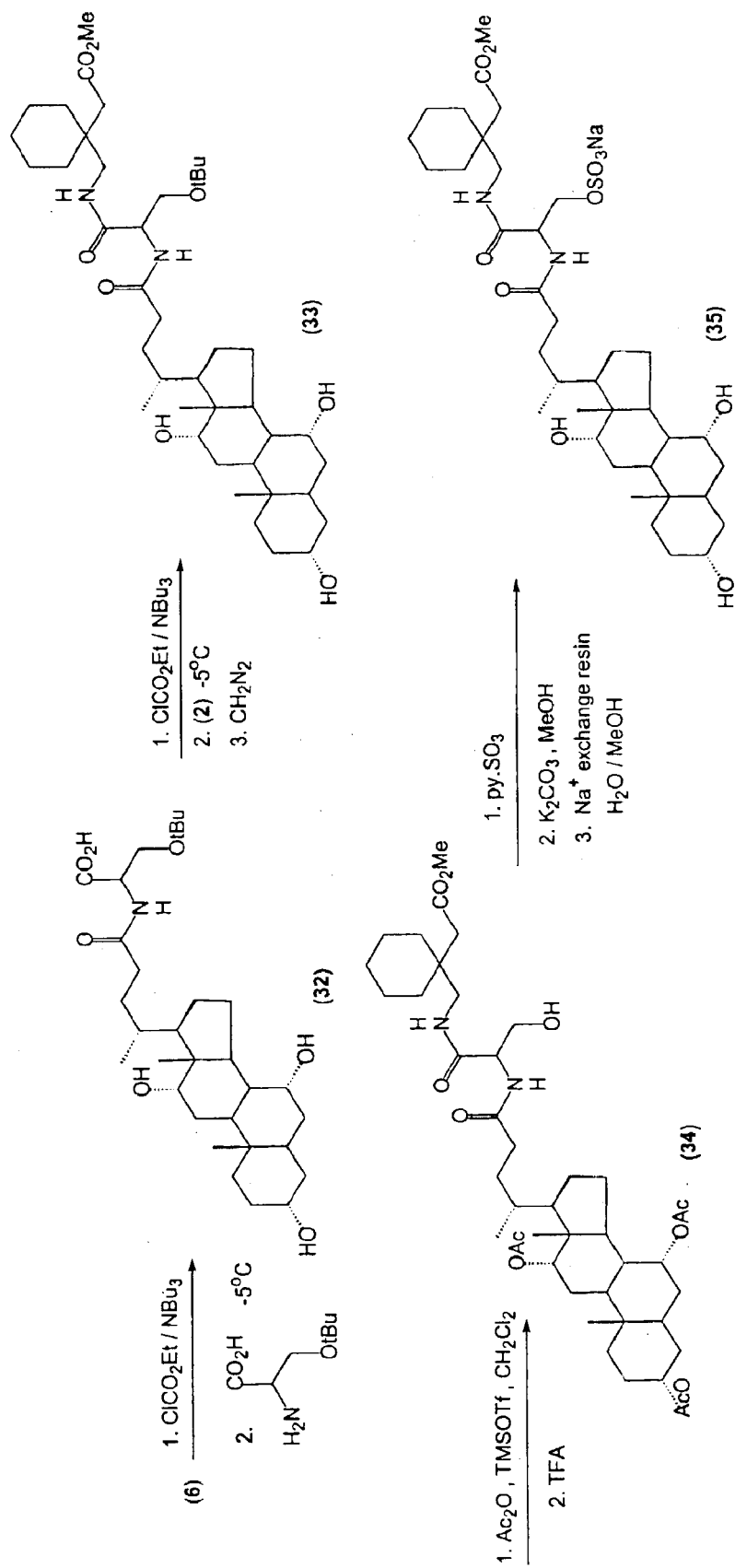
Figure 15:
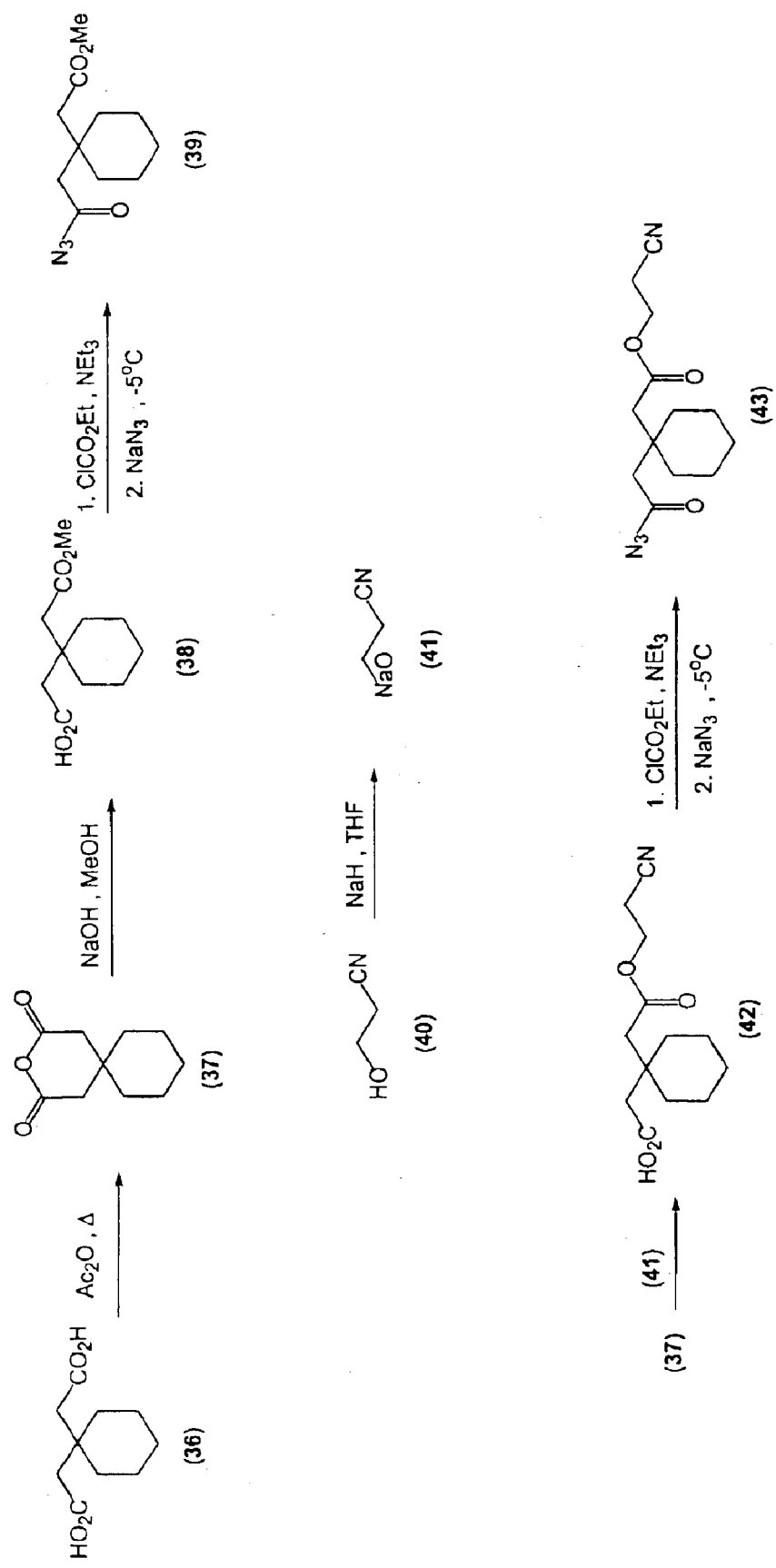
Figure 16:
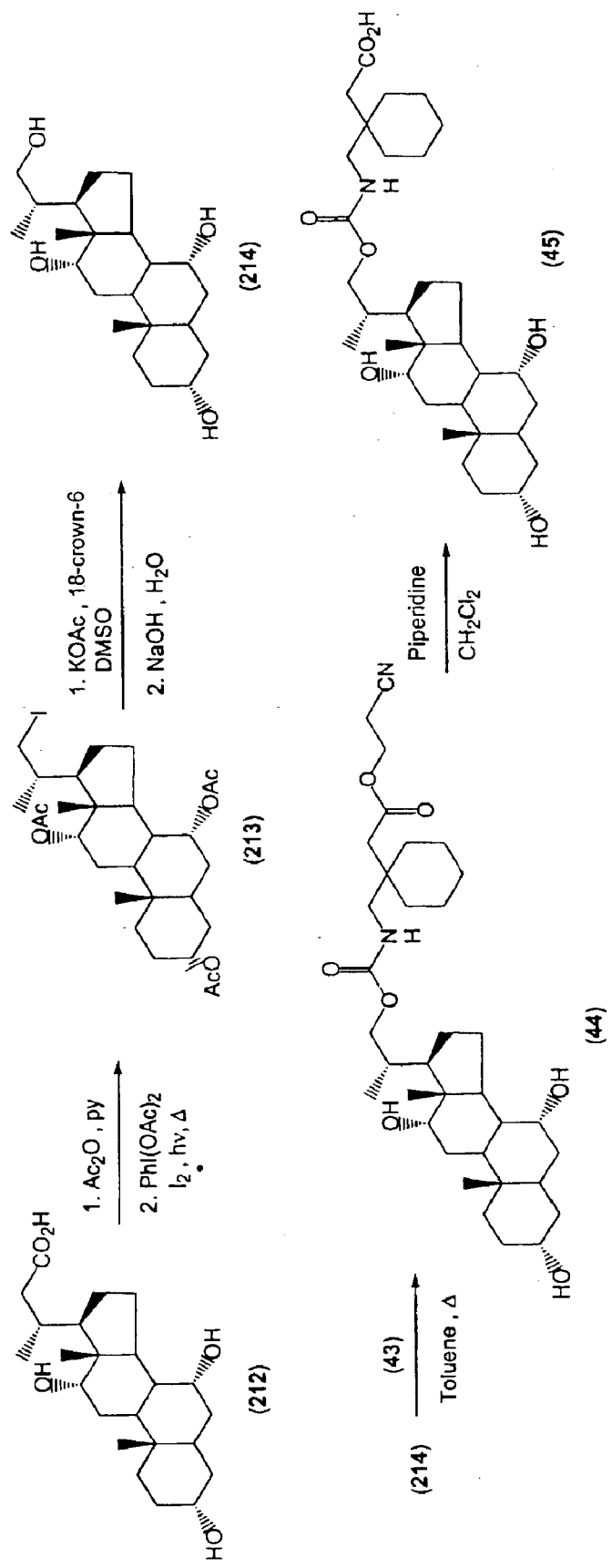
Figure 17:
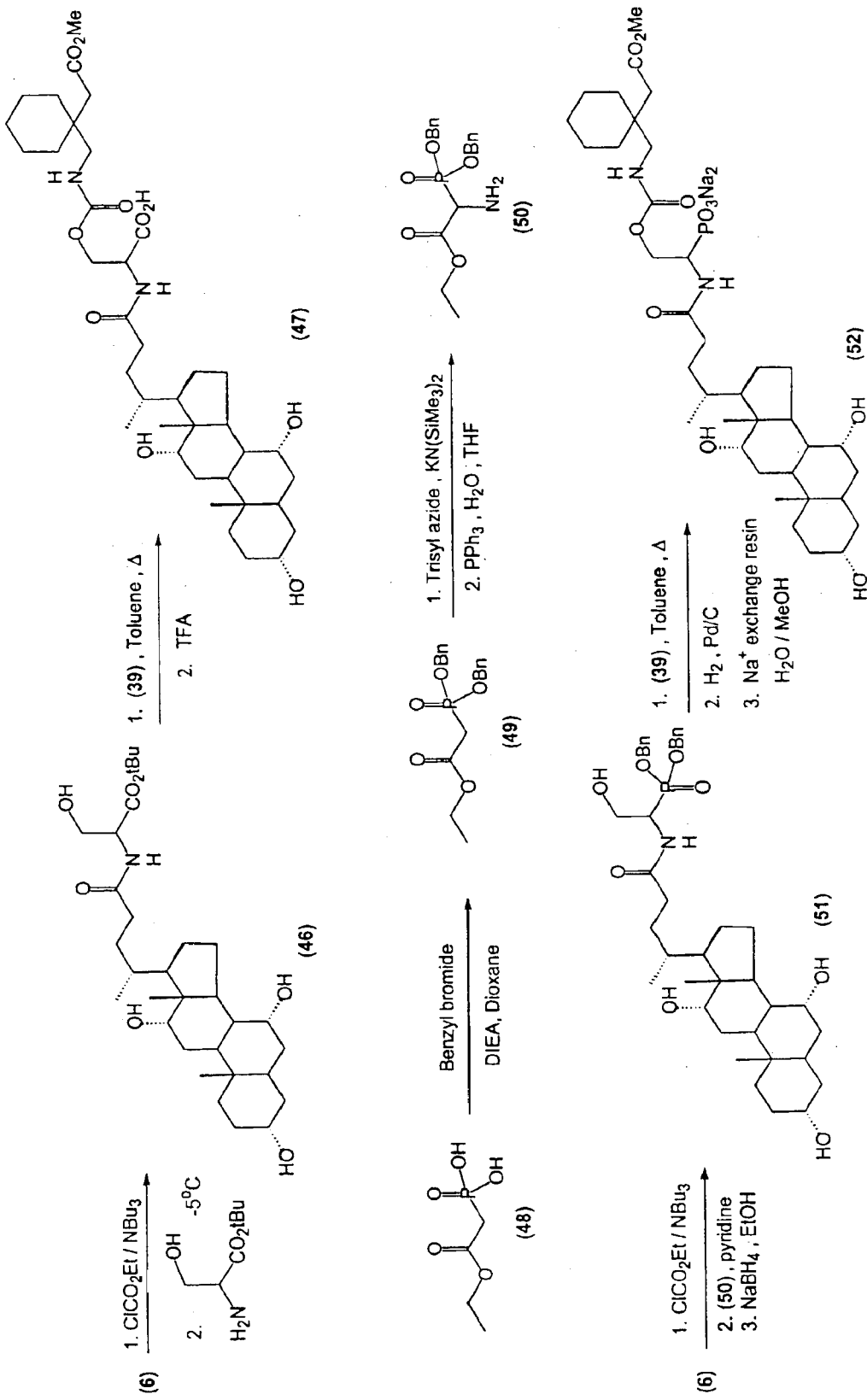
Figure 18:
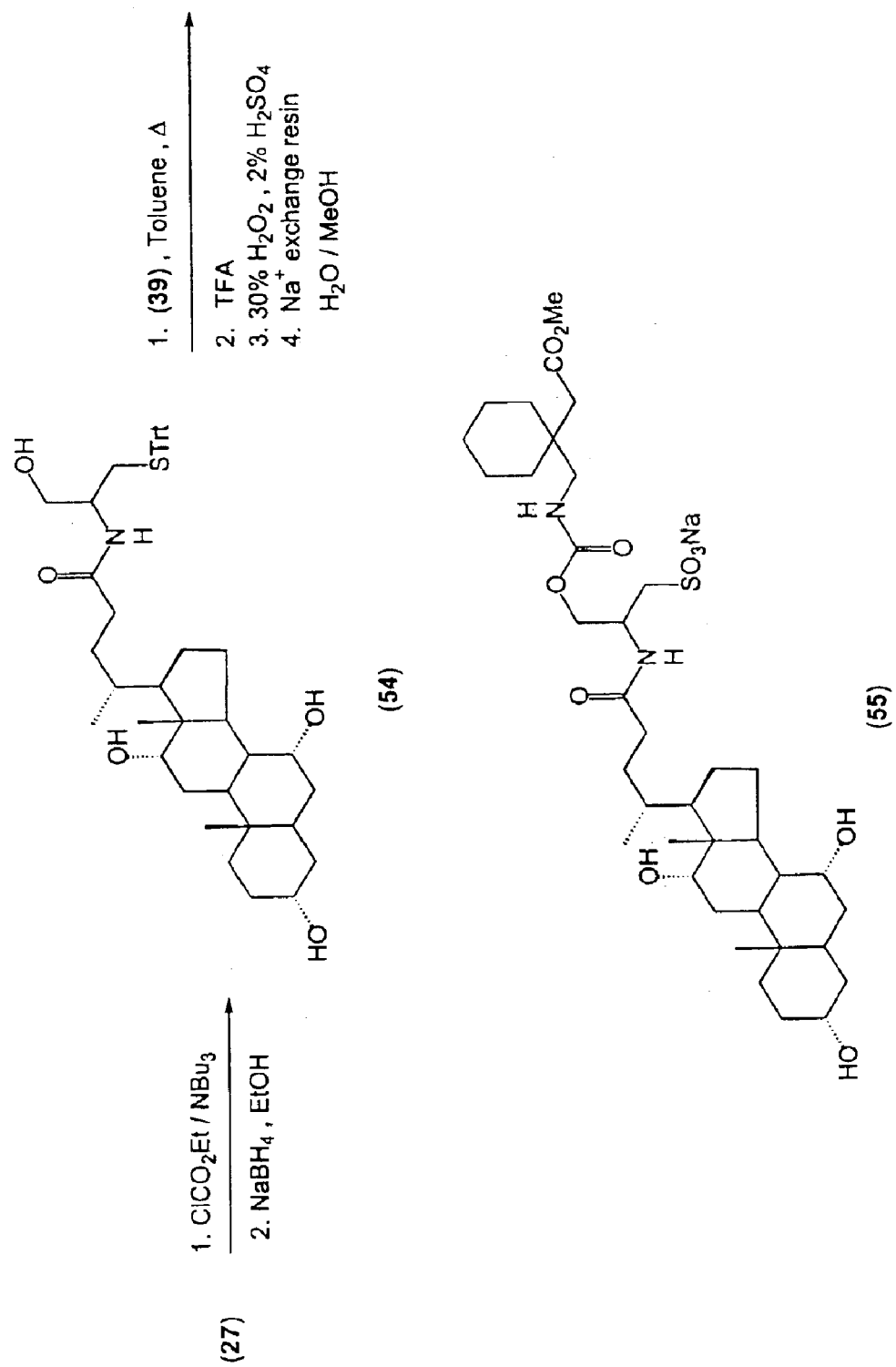
Figure 19:
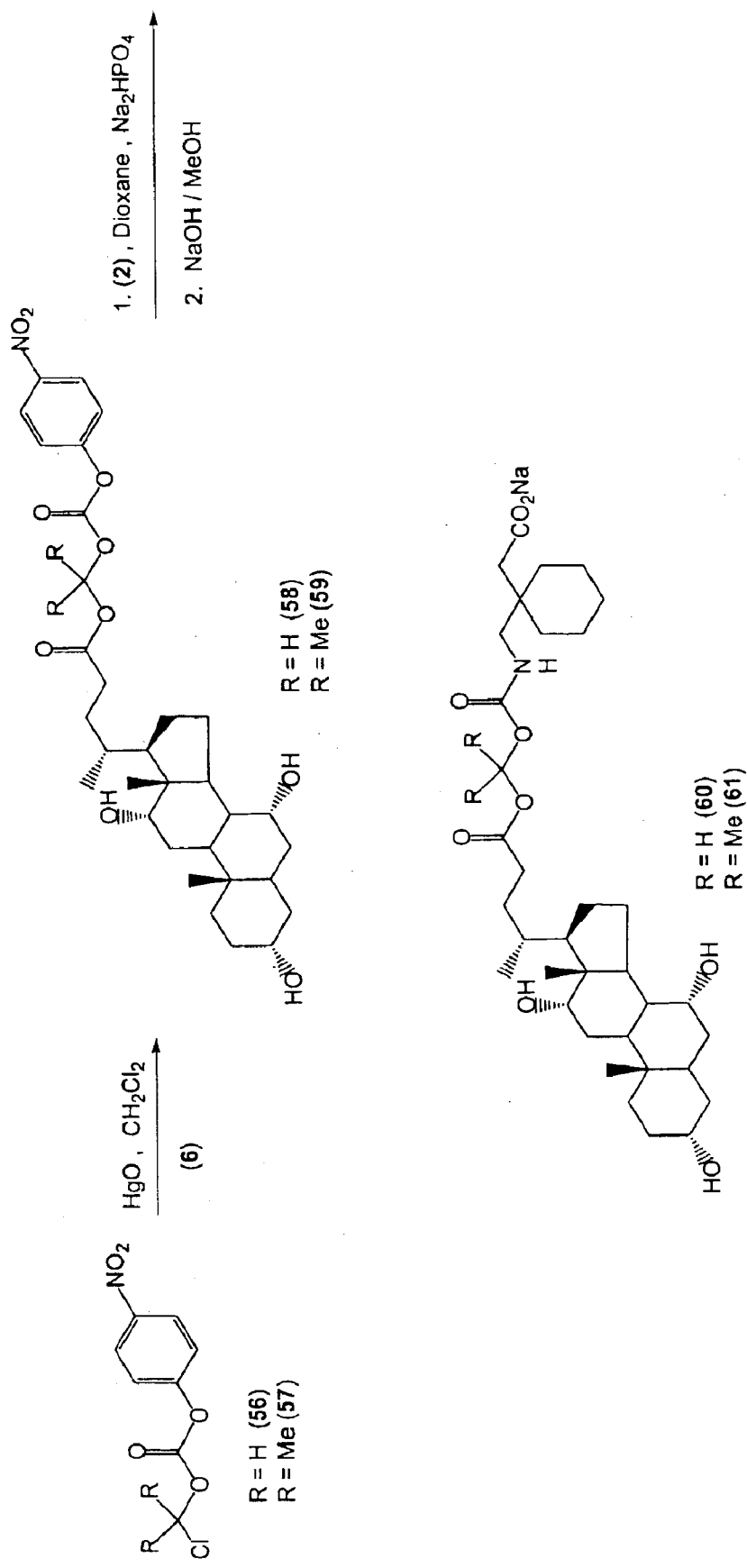
Figure 20:
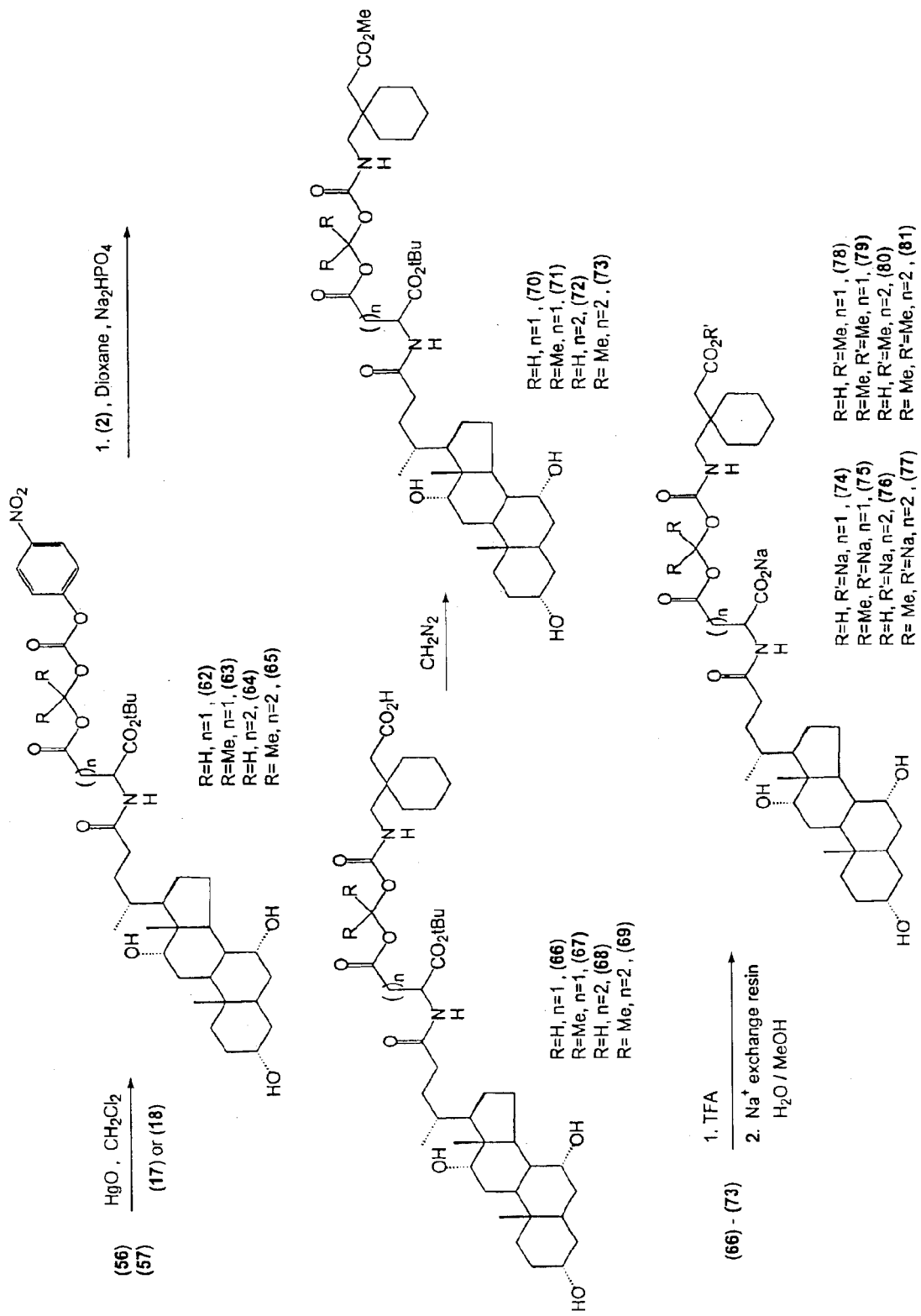
Figure 21:
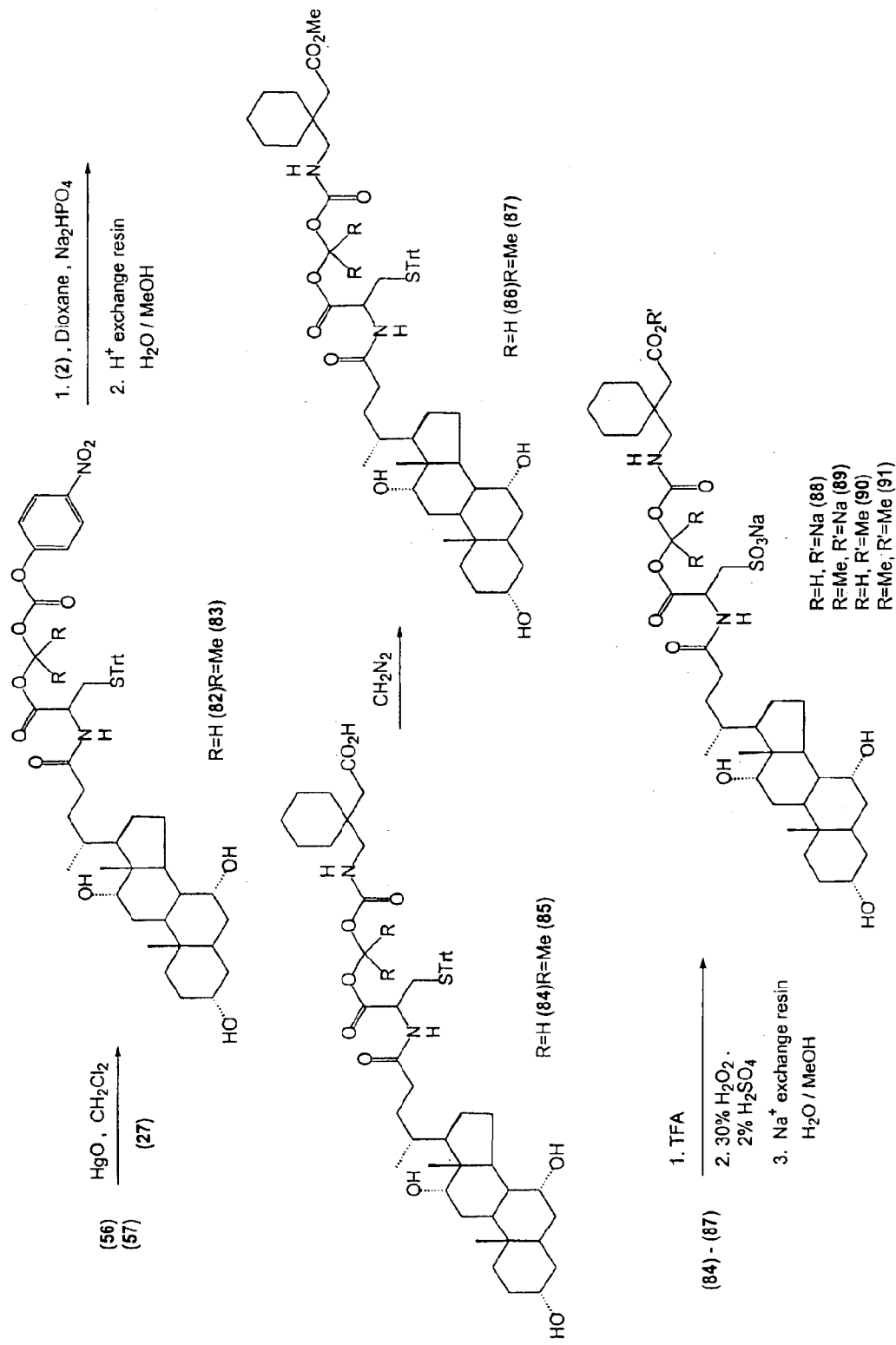
Figure 22:
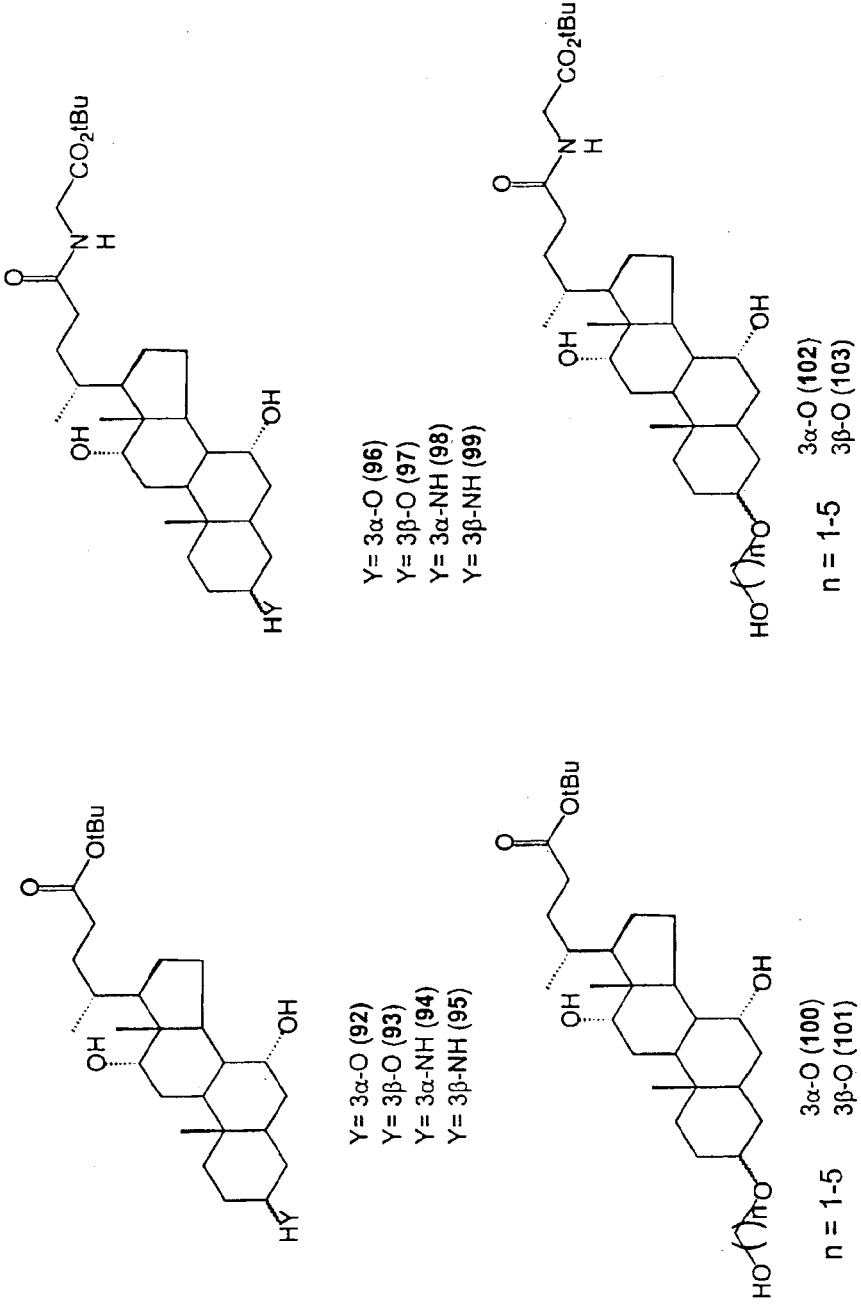
Figure 23:
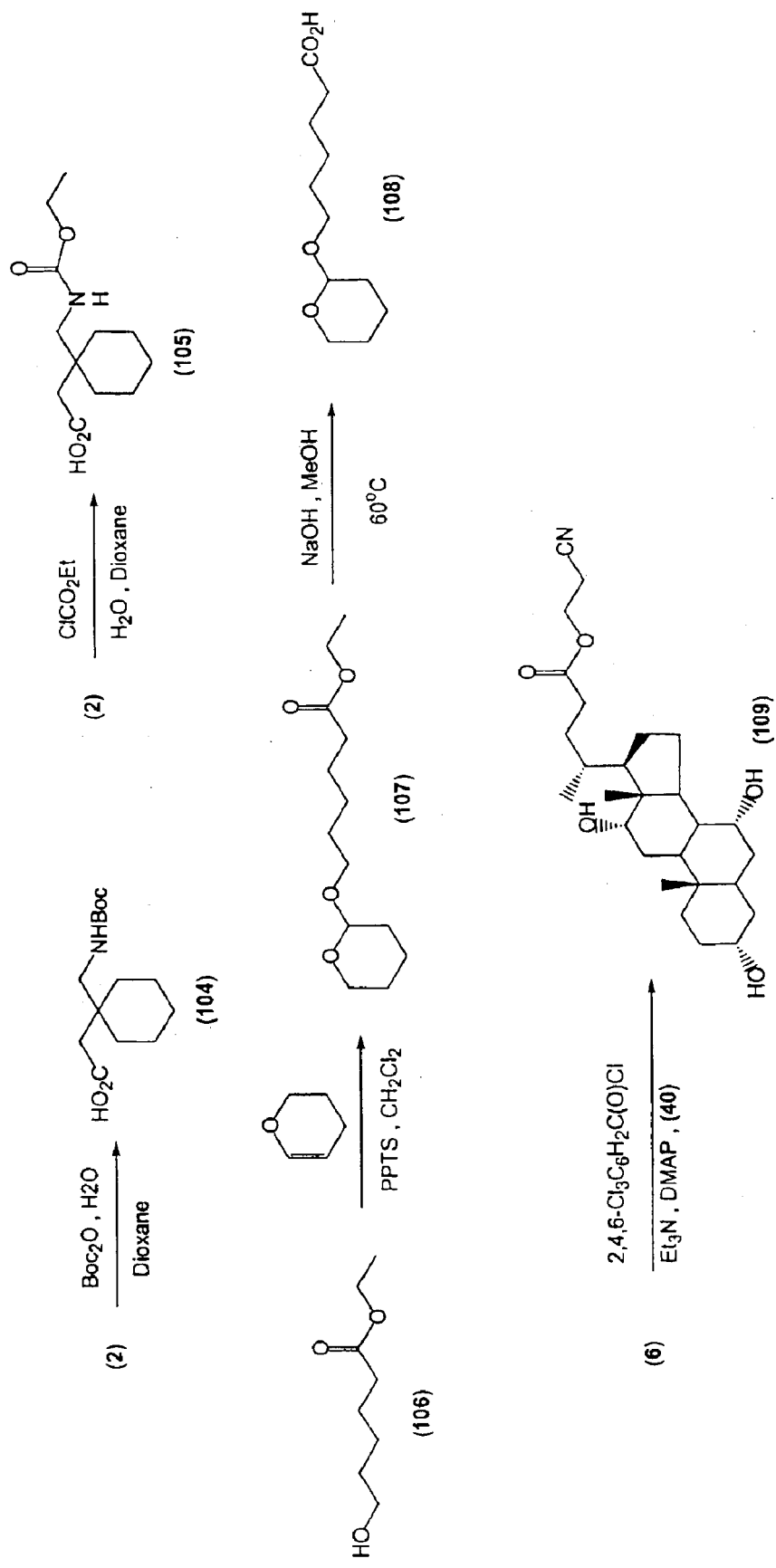

$IC_{50}$ data from radiolabeled competition assay in transporter-expressing CHO cells
$EC_{50}$ and % Max data (relative to glycodeoxycholate) from transporter-expressing oocytes
ND-Not determined Example 43
In Vitro Uptake of (8) by CHO Cells Transfected with IBAT or LBAT Evaluated by LC-MS/MS Active transport of (8) by the bile acid transport system was evaluated in vitro by incubation of (8) or glycocholate (control substrate) with untransfected CHO K1 cells or CHO cells transfected with either IBAT or LBAT. Cells ($10^5$ cells/mL) were incubated in 96 well plates with varying concentrations (0.06 to 1000 μM) of (8) or glycocholate for 10 min. Cells were then washed with Hank's Balanced Salt Solution (HBSS) and lysed and extracted by addition of 100 μL of water followed by sonication. Concentrations of (8) or glycocholate in cell extracts were determined by direct injection onto an API 2000 LC/MS/MS equipped with an Agilent 1100 binary pump and autosampler. Separation was achieved using a Keystone BDS Hypersil 2×50 mm column heated to 45° C. during the analysis. The mobile phases were: 0.1% formic acid in water (A) and 0.1% formic acid in acetonitrile (B). The gradient condition was: 5% B for 1 min, increasing to 90% B in 0.2 min, maintained for 2.8 min and returning to 5% B for 2 min. A TurbolonSpray source was used on the API 2000. The analysis was performed in the positive ion mode and MRM transitions of 466/412 and 562/154 were used in the analysis of glycocholate and (8), respectively. Ten microliters of the cell extracts were injected. Peaks were integrated using Analyst quantitation software. The method was linear for (8) or glycocholate over the concentration range 0.039 to 10 μM. FIG. 9 shows the relationship between the substrate concentration and the rate of uptake of (8) or glycocholate into IBAT transfected cells (the background non-specific uptake of these compounds into untransfected CHO K1 cells was subtracted to provide specific active uptake). Similarly, FIG. 10 shows the relationship between the substrate concentration and the rate of uptake of (8) or glycocholate into LBAT transfected cells (the background non-specific uptake of these compounds into untransfected CHO K1 cells was subtracted to provide specific active uptake). Active uptake of (8) was observed for both bile acid transport systems indicating the potential for enterohepatic recirculation of the prodrug.

Example 44
In Vitro Enzymatic Release of Gabapentin (2) from (8)

Sustained oral delivery of a drug molecule by attachment through a cleavable linker arm to an actively transported promoiety requires that the drug eventually be released from the drug/cleavable linker/transporter compound (prodrug) by enzymatic cleavage in one or more tissues of the enterohepatic circulation. The release of gabapentin from the prodrug (8) was evaluated in vitro using tissues representative of those involved in the enterohepatic circulation. Tissues were obtained from commercial sources (e.g., Pel-Freez Biologicals, Rogers, Ariz. or GenTest Corporation, Woburn, Mass.). Stability of (8) towards specific enzymes (e.g., carboxypeptidase A, cholylglycine hydrolase) was also evaluated by incubation with the purified enzyme. Experimental conditions used for the in vitro studies are described in Table 3 below. Each preparation was incubated with (8) at 37° C. for one hour. Aliquots (50 μL) were removed at 0, 30, and 60 min and quenched with 0.1% trifluoroacetic acid in acetonitrile. Samples were then centrifuged and analyzed by LC/MS/MS as described in Example 43. Gabapentin was quantified using MRM transition of 172.0/137.2. The data indicate a slow rate of hydrolysis of (8) in plasma, liver, or intestine resulting in formation of gabapentin. Substantially faster release of gabapentin was catalyzed by cholylglycine hydrolase (the naturally occurring bacterial enzyme responsible for hydrolysis of glycocholate in vivo).

TABLE 3

In Vitro Enzymatic Release of Gabapentin from (8)

| Preparation | Substrate Concentration | Cofactors | Percent of Gabapentin Released in 60 min |
|---|---|---|---|
| Rat Plasma | 2.0 μM | None | 0.55 |
| Human Plasma | 2.0 μM | None | 0.31 |
| Rat Liver S9 (0.5 mg/mL) | 2.0 μM | NADPH | 1.67 |
| Human Liver S9 (0.5 mg/mL) | 2.0 μM | NADPH | 4.89 |
| Human Intestine S9 (0.5 mg/mL) | 2.0 μM | NADPH | 1.31 |
| Cholylglycine Hydrolase (87 units/mL) | 0.8 μM | None | 35.31 |
| Carboxypeptidase A (10 units/mL) | 2.0 μM | None | Stable |

Example 45
Sustained Release of Gabapentin from (8) Following Oral Administration to Rats The pharmacokinetics of the prodrug (8) were examined in rats. Three groups of four male Sprague-Dawley rats (approx 200 g) with jugular cannulae each received one of the following treatments: A) a single bolus intravenous injection of gabapentin (25 mg/kg, as a solution in water); B) a single oral dose of gabapentin (25 mg/kg, as a solution in water) administered by oral gavage; C) a single oral dose of (8) (85.25 mg/kg, as a solution in water) administered by oral gavage. Animals were fasted overnight prior to dosing and until 4 hours post-dosing. Serial blood samples were obtained over 24 hours following dosing and blood was processed for plasma by centrifugation. Plasma samples were stored at −80° C. until analyzed. Concentrations of (8) or gabapentin in plasma samples were determined by LC/MS/MS as described in Example 44. Plasma (50 μL) was precipitated by addition of 100 mL of methanol and supernatent was injected directly onto the LC/MS/MS system. The method was linear for gabapentin over the concentration range 0.001 to 20 ng/mL and for (8) over the concentration range 0.01 to 10 ng/mL. Following oral administration of gabapentin, concentrations of gabapentin in plasma reached a maximum at 2.8±2.5 hours ($T_{max}$) and declined thereafter with a terminal half-life of 2.4±0.5 hours. The oral bioavailability of gabapentin was 87±18%. Following oral administration of (8), concentrations of intact (8) in plasma reached a maximum at ~8 hours post-dosing and were sustained out to 24 hours (terminal half-life>12 hours). Concentrations of released gabapentin in plasma were similarly sustained out to 24 hours (half-life>12 hours). These data indicate that prodrug (8) is metabolized to gabapentin in vivo, and that substantially sustained release of gabapentin was achieved following oral administration of (8) compared to the relatively rapid clearance observed for oral gabapentin.

Example 46
Secretion of (8) in Bile Following Oral Administration to Rats

Sustained release of gabapentin from a prodrug that is subject to enterohepatic recirculation requires that a proportion of the intact prodrug be absorbed after oral administration and subsequently secreted into the bile intact. The potential for enterohepatic recirculation of intact (8) was examined in rats with indwelling bile duct fistulae. A group of four male Sprague-Dawley rats (approx. 200 g) cannulated in both the jugular vein and the common bile duct each received a single oral dose of (8) (85.25 mg/kg, as a solution in water) by oral gavage. Serial blood samples were obtained over 24 hours following dosing and blood was processed for plasma by centrifugation. Bile was collected continuously in aliquots over 24 hours. Plasma and bile samples were frozen at −80° C. until analyzed. Concentrations of (8) or gabapentin in plasma samples were determined by LC/MS/MS as described in Example 45. Concentrations of intact (8) in bile were similarly determined by LC/MS/MS. Bile (20 μL) was diluted 1:1000 with methanol and injected directly onto the HPLC system. Concentrations of (8) in bile reached a maximum at ~6 hours post-dosing and were sustained up to 24 hours. These data indicate that (8) was successfully transported across the intestine by the ileal bile acid transport system (IBAT) and further secreted into the bile by the liver bile acid transporter (LBAT). However, no gabapentin was detected in plasma of bile duct-cannulated rats, indicating that cleavage of the prodrug was dependent on enterohepatic recirculation.

In view of the above disclosure, it is understood, of course, that combinations of substituents within the compounds of the present invention do not include any combination that is chemically impossible or non-feasible as would be appreciated by one skilled in the art.

What is claimed is:

1. A method for achieving sustained therapeutic or prophylactic blood concentrations of a GABA analog or an active metabolite thereof in the systemic circulation of an animal which method comprises orally administering to said animal a compound of formula (I):

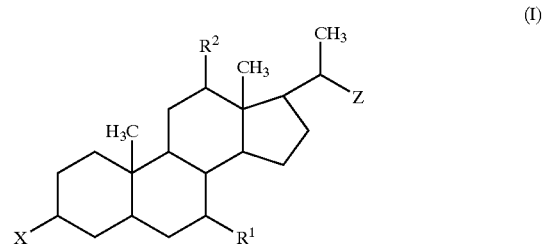

(I)

wherein:
$R^1$ and $R^2$ are independently hydrogen or hydroxy;
X is hydroxy;
Z is a group of the formula:

—M—$Q^b$—D' wherein:
M is selected from the group consisting of —CH$_2$OC(O)— and —CH$_2$CH$_2$C(O)—;
$Q^b$ is a linking group of formula:

—[E—(F*)$_n$—G]$_m$— wherein:
m is an integer of from 1 to 4;
n is 0 or 1;
E is —O—;
F* is selected from a group consisting of alkylene, substituted alkylene, alkenylene, substituted alkenylene, alkynylene, and substituted alkynylene; and
G is —C(O);
wherein $Q^b$ is cleavable under physiological conditions provided that $Q^b$ is not a linear oligopeptide consisting of 1, 2 or 3 α-amino acids and/or β-amino acids; and
D' is a GABA analog moiety of the formula:

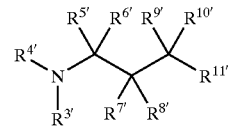

wherein:
$R^{3'}$ is a covalent bond linking the GABA analog moiety to $Q^b$;
$R^{4'}$ is hydrogen or $R^{4'}$ and $R^{9'}$ together with the atoms to which they are attached form a heterocyclic ring;
$R^{5'}$ and $R^{6'}$ are independently selected from the group consisting of hydrogen, alkyl, substituted alkyl, alkenyl, substituted alkenyl, alkynyl, aryl, substituted aryl, heteroaryl and substituted heteroaryl;

R[7'] and R[8'] are independently selected from the group consisting of hydrogen, alkyl, substituted alkyl, alkenyl, alkynyl, aryl, substituted aryl, heteroaryl and substituted heteroaryl, or R[7'] and R[8'] together with the atoms to which they are attached form a cycloalkyl, substituted cycloalkyl, heterocyclic or substituted heterocyclic ring;

R[9'] is selected from the group consisting of hydrogen, alkyl, substituted alkyl, alkenyl, alkynyl, aryl, substituted aryl, heteroaryl and substituted heteroaryl;

R[10'] is selected from the group consisting of hydrogen, alkyl, substituted alkyl, alkenyl, alkynyl, aryl, substituted aryl, heteroaryl and substituted heteroaryl;

R[11'] is selected from the group consisting of carboxylic acid, carboxylic amide, and carboxylic ester; or a pharmaceutically acceptable salt thereof.

2. The method according to claim 1 wherein
R[1] and R[2] are both α-OH; or
R[1] is β-OH and R[2] is hydrogen; or
R[1] is α-OH and R[2] is hydrogen; or
R[1] is hydrogen and R[2] is α-OH; or
R[1] is β-OH and R[2] is α-OH; or
R[1] and R[2] are both hydrogen.

3. The method according to claim 1 wherein —M—$Q^b$—D' is selected to cleave under physiological conditions at a rate to provide a therapeutic and/or prophylactic blood concentration of the GABA analog or active metabolite thereof in the animal for a period of at least about 10% longer than when the GABA analog is orally delivered by itself at an equivalent dose.

4. A compound of formula (I):

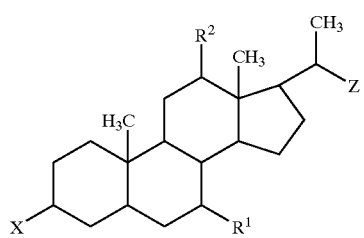

(I)

wherein:
R[1] and R[2] are independently hydrogen or hydroxy;
X is hydroxy;
Z is a group of the formula:

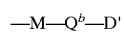
—M—$Q^b$—D' wherein:
M is selected from the group consisting of —CH$_2$OC(O)— and —CH$_2$CH$_2$C(O)—;
$Q^b$ is a linking group of formula:

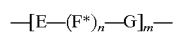
—[E—(F*)$_n$—G]$_m$— wherein:
m is an integer of from 1 to 4;
n is 0 or 1;
E is —O—;
F* is selected from a group consisting of alkylene, substituted alkylene, alkenylene, substituted alkenylene, alkynylene and substituted alkynylene, and
G is —C(O)—;

wherein $Q^b$ is cleavable under physiological conditions; and

D' is a GABA analog moiety of the formula:

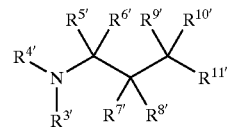

wherein:
R[3'] is a covalent bond linking the GABA analog moiety to $Q^b$;
R[4'] is hydrogen or R[4'] and R[9'] together with the atoms to which they are attached form a heterocyclic ring;
R[5'] and R[6'] are independently selected from the group consisting of hydrogen, alkyl, substituted alkyl, alkenyl, substituted alkenyl, alkynyl, aryl, substituted aryl, heteroaryl and substituted heteroaryl;
R[7'] and R[8'] are independently selected from the group consisting of hydrogen, alkyl, substituted alkyl, alkenyl, alkynyl, aryl, substituted aryl, heteroaryl and substituted heteroaryl, or R[7'] and R[8'] together with the atoms to which they are attached form a cycloalkyl, substituted cycloalkyl, heterocyclic or substituted heterocyclic ring;
R[9'] is selected from the group consisting of hydrogen, alkyl, substituted alkyl, alkenyl, alkynyl, aryl, substituted aryl, heteroaryl and substituted heteroaryl;
R[10'] is selected from the group consisting of hydrogen, alkyl, substituted alkyl, alkenyl, alkynyl, aryl, substituted aryl, heteroaryl and substituted heteroaryl;
R[11'] is selected from the group consisting of carboxylic acid, carboxylic amide, and carboxylic ester; or
a pharmaceutically acceptable salt thereof;
provided that $Q^b$ is not a linear oligopeptide comprised exclusively of 1, 2 or 3 α-amino acids and/or β-amino acids.

5. A compound of formula (II):

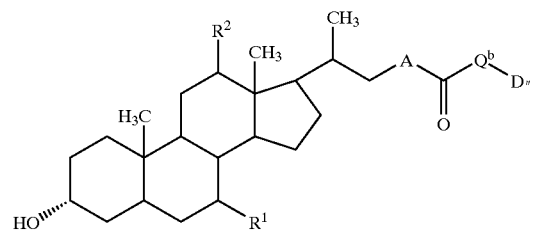

(II)

wherein:
R[1] and R[2] are both α-OH; or R[1] is β-OH and R[2] is hydrogen; or R[1] is α-OH and R[2] is hydrogen; or R[1] is hydrogen and R[2] is α-OH; or R[1] is β-OH and R[2] is α-OH; or R[1] and R[2] are both hydrogen;
A is —O— or —CH$_2$—;
D" is a GABA analog moiety selected from the group consisting of:

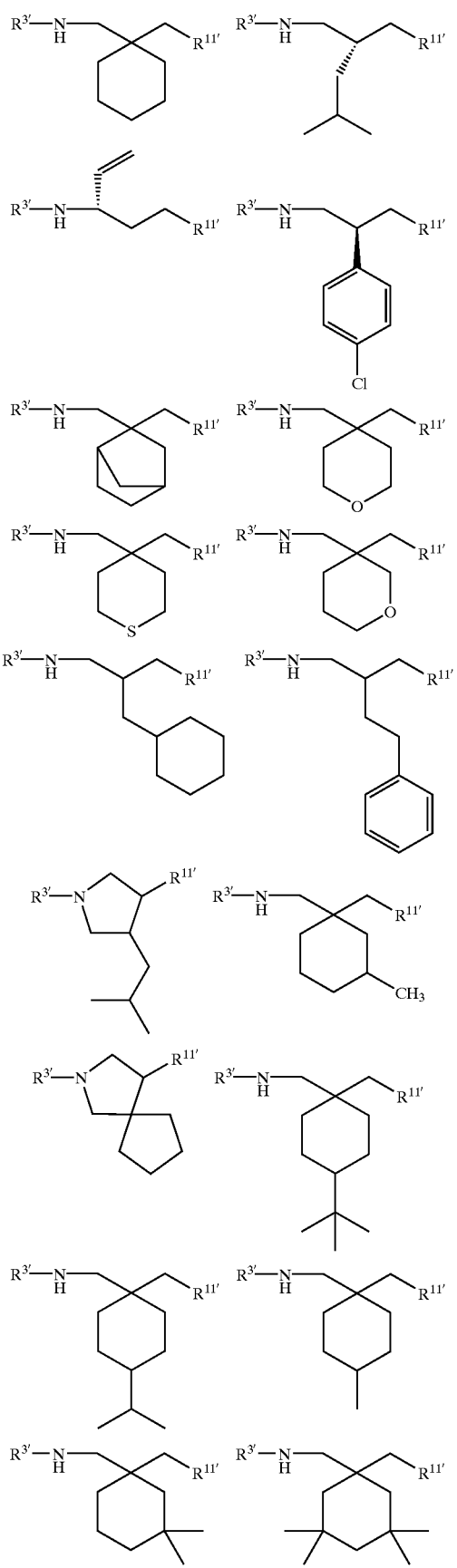
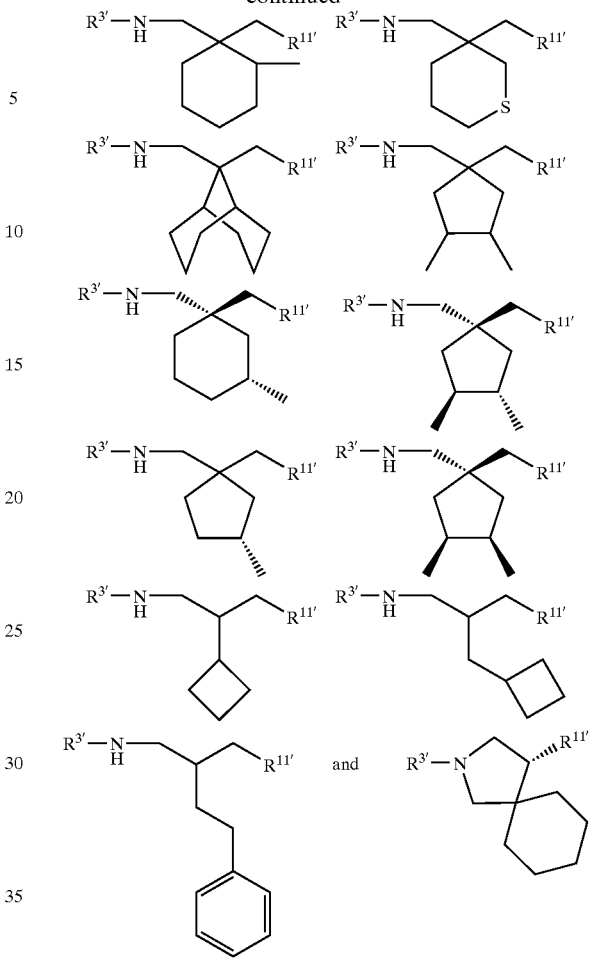

where
R[3'] is a covalent bond linking D" to $Q^b$;
R[11'] is carboxyl acid; and
$Q^b$ is a linker of the following formula:

—[E—(F*)$_n$—G]$_m$— wherein:
m is an integer of from 1 to 4;
n is 0 or 1;
E is —O—;
F* is selected from a group consisting of alkylene, substituted alkylene, alkenylene, substituted alkenylene, alkynylene, and substituted alkynylene; and
G is —C(O)—;
wherein $Q^b$ is cleavable under physiological conditions provided $Q^b$ is not a linear oligopeptide consisting of 1, 2 or 3 α-amino acids and/or β-amino acids; or
a pharmaceutically acceptable salt thereof.

6. The compound according to claim 5, wherein F* is selected from a group consisting of alkylene, alkynylene and alkylene substituted with a group selected from the group consisting of —COOH, —SO$_3$H, —SO$_2$H, —P(O)(OR$^{19}$)(OH), —OP(O)(OR$^{19}$)(OH), —OSO$_3$H, wherein R$^{19}$ is selected from the group consisting of alkyl, substituted alkyl, aryl and substituted aryl; and where one, two or three methylene groups are optionally replaced by a carboxy (—C(O)O—) group.

7. The compound according to claim 5 wherein $Q^b$ is a cleavable linker of formula (vii):

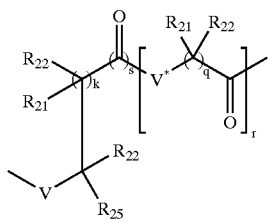

wherein:
V and V* are O;
$R^{25}$ is $R^{21}$ or $(CR^{21}R^{22})_1Z$;
Z is selected from the group consisting of —$CO_2H$, —$SO_3H$, —$OSO_3H$, —$SO_2H$, —$P(O)(OR^{19})(OH)$ and —$OP(O)(OR^{19})(OH)$;
$R^{19}$ is selected from the group consisting of alkyl, substituted alkyl, aryl and substituted aryl;
s is 1;
r is 0, 1 or 2;
k is 0, 1, 2, 3 or 4;
q is 1, 2, 3 or 4;
l is 0 or 1;
$R^{21}$ and $R^{22}$ are independently hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{21}$ and $R^{22}$ together with the atoms to which they are attached form a cycloalkyl, substituted cycloalkyl, heterocyclyl or substituted heterocyclyl ring.

8. A pharmaceutical composition comprising a pharmaceutically acceptable excipient and a compound according to any of claims 4 or 5.

9. A method for treating a disease condition in a mammal, wherein said disease condition is selected from epilepsy, faintness attacks, hypokinesia, cranial disorders, neurodegenerative disorders, depression, anxiety, panic, pain, neuropathic pain, neuropathological disorders, gastrointestinal damage, inflammation and irritable bowel disease, which method comprises administering to said mammal a pharmaceutical composition according to claim 8.

* * * * *